US011682487B2

(12) United States Patent
Shelton, IV et al.

(10) Patent No.: US 11,682,487 B2
(45) Date of Patent: Jun. 20, 2023

(54) ACTIVE RECOGNITION AND PAIRING SENSING SYSTEMS

(71) Applicant: Cilag GmbH International, Zug (CH)

(72) Inventors: Frederick E. Shelton, IV, Hillsboro, OH (US); Jason L. Harris, Lebanon, OH (US); Chad E. Eckert, Terrace Park, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/156,324

(22) Filed: Jan. 22, 2021

(65) Prior Publication Data

US 2022/0238209 A1   Jul. 28, 2022

(51) Int. Cl.
*H04B 1/38* (2015.01)
*G16H 40/20* (2018.01)
(Continued)

(52) U.S. Cl.
CPC ............ *G16H 40/20* (2018.01); *A61B 90/36* (2016.02); *G16H 40/60* (2018.01); *A61B 2090/365* (2016.02)

(58) Field of Classification Search
CPC ........ G16H 40/20; G16H 40/60; A61B 90/36; A61B 2090/365
See application file for complete search history.

(56) References Cited

U.S. PATENT DOCUMENTS 8,696,616 B2   4/2014   Baynham et al.
8,864,009 B2   10/2014  Shelton et al.
(Continued)

FOREIGN PATENT DOCUMENTS

CN   111616803 A       9/2020
CN   112220562   *   1/2021   ....... A61B 1/000096
(Continued)

OTHER PUBLICATIONS

Carroll, et al., "Multi-Sensor Esophageal Temperature Probe Used During Radiofrequency Ablation for Atrial Fibrillation is Associated with Increased Intraluminal Temperature Detection and Increased Risk of Esophageal Injury Compared to Single-Sensor Probe", Journal of Cardiovascular Electrophysiology vol. 24, No. 9, Sep. 2013, 8 pages.

(Continued)

*Primary Examiner* — Hongmin Fan
(74) *Attorney, Agent, or Firm* — Condo Roccia Koptiw LLP

(57) ABSTRACT

A surgical computing system may scan for a sensing system located in an operating room. Upon detecting a sensing system in the operating room, the surgical computing system may establish a link with the sensing system. The surgical computing system may receive user role identification data from the sensing system using the established link. The surgical computing system may identify a user role for a user in the operating room based on the received user role identification data. The user role of a user may be or may include at least one of a surgeon, a nurse, a patient, a hospital staff, or a health care professional. Based on the identified user role, the surgical computing system may generate and send surgical aid information for the user in the operating room. The surgical aid information may include information associated with a surgical operation relevant to the identified user role.

20 Claims, 24 Drawing Sheets

(51) Int. Cl.
*A61B 90/00* (2016.01)
*G16H 40/60* (2018.01)

(56) References Cited

U.S. PATENT DOCUMENTS

| | | | |
|---|---|---|---|
| 9,072,535 | B2 | 7/2015 | Shelton et al. |
| 9,700,317 | B2 | 7/2017 | Aronhalt et al. |
| 9,974,903 | B1 | 5/2018 | Davis et al. |
| 2005/0021369 | A1* | 1/2005 | Cohen .................. H04L 67/306 455/73 |
| 2011/0152759 | A1 | 6/2011 | Clymer et al. |
| 2012/0116365 | A1 | 5/2012 | Price et al. |
| 2013/0038707 | A1 | 2/2013 | Cunningham et al. |
| 2014/0081659 | A1 | 3/2014 | Nawana et al. |
| 2014/0236159 | A1 | 8/2014 | Haider et al. |
| 2014/0263541 | A1 | 9/2014 | Leimbach et al. |
| 2014/0263551 | A1 | 9/2014 | Hall et al. |
| 2014/0263552 | A1 | 9/2014 | Hall et al. |
| 2016/0030240 | A1 | 2/2016 | Gonenc et al. |
| 2017/0119300 | A1 | 5/2017 | Conner |
| 2017/0258408 | A1 | 9/2017 | Stapelfeldt |
| 2017/0296213 | A1 | 10/2017 | Swensgard et al. |
| 2018/0028088 | A1 | 2/2018 | Garbey et al. |
| 2018/0168579 | A1 | 6/2018 | Aronhalt et al. |
| 2018/0286521 | A1 | 10/2018 | Fong |
| 2018/0360452 | A1 | 12/2018 | Shelton et al. |
| 2019/0013099 | A1 | 1/2019 | Esterberg et al. |
| 2019/0059932 | A1 | 2/2019 | Isosaki et al. |
| 2019/0104919 | A1 | 4/2019 | Shelton, IV et al. |
| 2019/0200844 | A1 | 7/2019 | Shelton et al. |
| 2019/0200981 | A1 | 7/2019 | Harris et al. |
| 2019/0201033 | A1 | 7/2019 | Yates et al. |
| 2019/0201043 | A1 | 7/2019 | Shelton et al. |
| 2019/0201102 | A1 | 7/2019 | Shelton, IV et al. |
| 2019/0201104 | A1 | 7/2019 | Shelton, IV et al. |
| 2019/0201129 | A1 | 7/2019 | Shelton, IV et al. |
| 2019/0201136 | A1 | 7/2019 | Shelton et al. |
| 2019/0201137 | A1 | 7/2019 | Shelton et al. |
| 2019/0201140 | A1 | 7/2019 | Yates et al. |
| 2019/0204201 | A1 | 7/2019 | Shelton, IV et al. |
| 2019/0206050 | A1 | 7/2019 | Yates et al. |
| 2019/0206562 | A1 | 7/2019 | Shelton, IV et al. |
| 2019/0206563 | A1 | 7/2019 | Shelton et al. |
| 2019/0206569 | A1 | 7/2019 | Shelton et al. |
| 2019/0216452 | A1 | 7/2019 | Nawana et al. |
| 2020/0168334 | A1 | 5/2020 | Mowery |
| 2020/0246081 | A1 | 8/2020 | Johnson et al. |
| 2020/0273575 | A1* | 8/2020 | Wolf ...................... A61B 34/30 |
| 2020/0315734 | A1 | 10/2020 | El Amm |
| 2020/0397515 | A1 | 12/2020 | Frimer et al. |
| 2021/0158955 | A1* | 5/2021 | Azizian .................. G16H 40/60 |
| 2021/0196384 | A1 | 7/2021 | Shelton, IV et al. |
| 2021/0196423 | A1 | 7/2021 | Shelton, IV et al. |
| 2021/0196425 | A1 | 7/2021 | Shelton, IV et al. |
| 2021/0386489 | A1* | 12/2021 | Wright .................. A61B 90/37 |

FOREIGN PATENT DOCUMENTS

| | | |
|---|---|---|
| EP | 3501459 A2 | 6/2019 |
| JP | 2019-525276 A | 9/2019 |
| JP | 2019-177134 A | 10/2019 |
| WO | 2007/096931 A2 | 8/2007 |
| WO | 2017/098503 A1 | 6/2017 |
| WO | 2017/147652 A1 | 9/2017 |
| WO | 2020/092701 A2 | 5/2020 |
| WO | 2020/180917 A1 | 9/2020 |
| WO | 2021/007418 A2 | 1/2021 |
| WO | 2021/126163 A1 | 6/2021 |

OTHER PUBLICATIONS

U.S. Appl. No. 17/156,287, filed Jan. 22, 2021, Shelton, et al.
U.S. Appl. No. 17/156,296, filed Jan. 22, 2021, Shelton, et al.
U.S. Appl. No. 17/156,300, filed Jan. 22, 2021, Shelton, et al.
U.S. Appl. No. 17/156,304, filed Jan. 22, 2021, Shelton, et al.
U.S. Appl. No. 17/156,266, filed Jan. 22, 2021, Shelton, et al.
U.S. Appl. No. 17/156,318, filed Jan. 22, 2021, Shelton, et al.
U.S. Appl. No. 17/156,309, filed Jan. 22, 2021, Shelton, et al.
U.S. Appl. No. 17/156,306, filed Jan. 22, 2021, Shelton, et al.
U.S. Appl. No. 17/156,321, filed Jan. 22, 2021, Shelton, et al.
U.S. Appl. No. 17/156,281, filed Jan. 22, 2021, Shelton, et al.
U.S. Appl. No. 17/156,272, filed Jan. 22, 2021, Shelton, et al.
U.S. Appl. No. 17/156,279, filed Jan. 22, 2021, Shelton, et al.
U.S. Appl. No. 17/156,284, filed Jan. 22, 2021, Shelton, et al.
U.S. Appl. No. 17/156,282, filed Jan. 22, 2021, Shelton, et al.
U.S. Appl. No. 17/156,269, filed Jan. 22, 2021, Shelton, et al.
U.S. Appl. No. 17/156,286, filed Jan. 22, 2021, Shelton, et al.
U.S. Appl. No. 17/156,329, filed Jan. 22, 2021, Shelton, et al.
U.S. Appl. No. 17/156,289, filed Jan. 22, 2021, Shelton, et al.
U.S. Appl. No. 17/156,293, filed Jan. 22, 2021, Shelton, et al.
U.S. Appl. No. 17/156,298, filed Jan. 22, 2021, Shelton, et al.
U.S. Appl. No. 17/156,274, filed Jan. 22, 2021, Shelton, et al.
U.S. Appl. No. 17/156,278, filed Jan. 22, 2021, Shelton, et al.
U.S. Appl. No. 17/062,509, filed Oct. 2, 2020, Shelton, et al.
U.S. Appl. No. 62/611,341, filed Dec. 28, 2017, Shelton, et al.
Aliverti, et al., "Wearable technology: role in respiratory health and disease", Breathe, 2017, 10 pages.
Kazamias, et al., "Blood pressure measurement with Doppler ultrasonic flowmeter", Journal of Applied Physiology vol. 30, No. 4, Apr. 1971, 1 page.
Cerfolio, et a., "Prospective Randomized Trial Compares Suction Versus Water Seal for Air Leaks", General Thoracic, May 1, 2001, 5 pages.
Brunelli, et al., "A Scoring System to Predict the Risk of Prolonged Air Leak After Lobectomy", General Thoracic, 2010, 6 pages.
Jacob, et al., "Clinical applications of magnets on cardiac rhythm management devices", European Society of Cardiology, May 26, 2011, 9 pages.
Carroll,e t al.
Singh, et al., "Esophageal Injury and Temperature Monitoring During Atrial Fibrillation Ablation", American Heart Association, Circulation: Arrhythmia and Electrophysiology, vol. 1, issue 3, Aug. 1, 2008, 7 pages.
Nair, et al., "Atrioesophageal Fistula: A Review", Journal of Atrial Fibrillation vol. 8, Issue 3, Oct. Nov. 2015, 6 pages.
Drewry, et al., "Body temperature patterns as a predictor of hospital-acquired sepsis in afebrile adult intensive care unit patients: a case-control study", Critical Care 2013, 11 pages.
Diduch, et al., "Synchronization of Data Streams in Distributed Realtime Multimodal Signal Processing Environments Using Commodity Hardware", 4 pages.
Kwon, et al., "Electrocardiogram Sampling Frequency Range Acceptable for Heart Rate Variability Analysis", The Korean Society of Medical Informatics, 2018, 9 pages.
Pouchard, et al., "Open Standards for Sensor Information Processing", Oak Ridge National Laboratory, Jul. 2009, 49 pages.
Appelboom et al., "The Promise of Wearable Activity Sensors to Define Patient Recovery", Journal of Clinical Neuroscience, vol. 21, Jul. 1, 2014, pp. 1089-1093.
Chen et al., "Type of Pelvic Disease as a Risk Factor for Surgical Site Infection in Women Undergoing Hysterectomy", Journal of Minimally Invasive Gynecology, vol. 26, No. 6, Sep. 1, 2019, pp. 1149-1156.
Erowele et al., "Treatment Options for Postoperative Ileus", US Pharmacist, vol. 35, 2010.
Sugino et al., "Surgical Task Analysis of Simulated Laparoscopic Cholecystectomy with a Navigation System", International Journal of Computer Assisted Radiology and Surgery, vol. 9, Jan. 14, 2014, pp. 825-836.
Li Songpo et al: "Attention-aware robotic laparoscope for human-robot cooperative surgery", 2013 IEEE International Conference on Robotics and Biomimetics (ROBIO), IEEE, Dec. 12, 2013.
Jinbin, "Feedback—Friend or Foe?", Oct. 19, 2020.

* cited by examiner

ACTIVE RECOGNITION AND PAIRING SENSING SYSTEMS

CROSS-REFERENCE TO RELATED APPLICATIONS

This application is related to the following, filed contemporaneously, the contents of each of which are incorporated by reference herein:
Ser. No. 17/156,287, titled METHOD OF A ADJUSTING A SURGICAL PARAMETER BASED ON BIOMARKER MEASUREMENTS.

BACKGROUND

Surgical procedures are typically performed in surgical operating theaters or rooms in a healthcare facility such as a hospital. Various surgical devices and systems and/or sensing systems are utilized in performance of a surgical procedure. In the digital and information age and to improve patient practices, it would be desirable to find ways to help recognize and pair the various surgical devices, surgical systems, and/or sensing systems.

SUMMARY

A surgical computing system may scan for and detect a sensing system located in an operating room (OR). Based on the detection, the surgical computing system may establish a link with the sensing system. Using the established link between the surgical computing system and the sensing system, the surgical computing system may receive user role identification data from the sensing system. The user role identification data may be or may include information to identify a user role. The surgical computing system may identify a user role for a user in the OR based on the received user role identification data. The user role of a user in the OR may be or may include at least one of a surgeon, a nurse, a patient, a hospital staff, or a health care professional (HCP). Based on the identified user role, the surgical computing system may generate surgical aid information for the user in the OR. The surgical aid information may be or may include information associated with a surgical operation that is relevant to the identified user role. The surgical computing system described herein may be or may include a surgical hub.

The surgical computing system may receive different user role identification data from different sensing systems associated with multiple users in the OR. The computing system may identify various user roles and/or users based on the user role identification data received from the various sensing systems and provide different surgical aid information to the users based on their respective identified user role.

For example, the surgical computing system may receive user role identification, data from a first sensing system associated with a first user and may receive user role identification data from a second sensing system associated with a second user. The surgical computing system may identify a user role for the first user and a user role for the second user. The surgical computing system may determine, generate, and/or send surgical aid information to the users (e.g., to the first user or to the second user) based on the corresponding user roles.

For example, the user role identification data may be or may include one or more of tee following: a proximity of a user to a surgical instrument, locations and/or location tracking information of the users in the OR, interactions between the user and at least one healthcare professional, one or more surgical procedural activities, or visual data of the user in the OR. For example, the sensing system may be worn by the user such as a surgeon. The sensing system may monitor and/or store information about the proximity of the sensing system to a surgical instrument. The sensing system may store location tracking information of the surgeon during a surgical procedure. The sensing system may detect and/or store a surgical procedural activity of the surgeon. The sensing system may send such user role identification data to the surgical computing system.

For example, the surgical computing system may generate augmented reality (AR) content for a user based on the identified user role. Different AR content may be generated for different users based on their respective user roles identified via the sensing systems. The AR content may be or may include instructions on how to use a surgical instrument and/or an operation manual of the surgical instrument associated with the identified user role. The surgical computing system may send the generated AR content to the identified user. For example, the surgical computing system may send the AR content to an AR device associated with the user.

The surgical computing system may obtain surgical contextual data. The surgical computing system may identify a surgical instrument associated with the user based on the surgical contextual data and the identified user role. The surgical computing system may obtain an instruction on how to use the surgical instrument for inclusion in the surgical aid information.

For example, me surgical computing system may receive measurement data from a sensing system. The measurement data may include a stress level associated with a user and/or a fatigue level associated with the user. The surgical computing system may determine an elevated stress level and/or fatigue level associated with the user. The surgical computing system may generate and/or send the surgical aid information to the identified user that includes an instruction on how to use the surgical instrument if the surgical computing system detects an elevated stress level associated with the user. The surgical computing system may send an indication of fatigue control to the surgical instrument if the surgical computing system detects an elevated fatigue level associated with the user.

A computing system may scan for a sensing system located in an OR. The sensing system may include measurement data for a user. The computing system may determine whether the sensing system is compatible to establish a link with the computing system. Upon determining that the sensing system is compatible to establish a link, with the computing system, the computing system may establish a link and receive the measurement data using the link with the sensing system.

Upon determining that the sensing system is incompatible to establish a link with the computing system, the computing system may generate a virtual computing system that is compatible, to establish the link with the sensing system. The computing system may establish the link with the sensing system using the generated virtual computing system. The computing system may receive the measurement data using the link with the sensing system.

The computing system may establish an initial link with the sensing system before establishing a communication link with the sensing system. The computing system may send an initial link indication to a surgical computing system (e.g., a primary computing system). The initial link indication may request a user input to establish the link with the sensing system. The computing system may receive the user input from the surgical computing system. The computing system may establish the link with the sensing system.

The computing system may determine to generate AR content based on at least one of: the received measured data, locations of the sensing system in the OR, or surgical procedural activities of a surgical operation. The AR content may include display information associated with the measurement data. The computing system may send the generated AR content to an AR device associated with the user.

The computing system may detect one or more devices in the OR. For example, in the OR, there may be one or more surgeon sensing systems, patient sensing systems, computers, telephones, monitor screens, and/or other devices. The computing system may identify one or more sensing systems in the OR (e.g., to be paired with the computing system) from the detected devices in the OR. The computing system may establish a link with the identified sensing system.

DETAILED DESCRIPTION

Applicant of the present application owns the following U.S. Patent Applications, filed contemporaneously, each of which is herein incorporated by reference in its entirety:

U.S. patent application Ser. No. 16/209,416, entitled "METHOD OF HUB COMMUNICATION, PROCESSING, DISPLAY, AND CLOUD ANALYTICS," filed Dec. 4, 2018;

U.S. patent application Ser. No. 15/940,671, entitled "SURGICAL HUB SPATIAL AWARENESS TO DETERMINE DEVICES IN OPERATING THEATER," filed Mar. 29, 2018;

U.S. patent application Ser. No. 16/182,269 entitled "IMAGE CAPTURING OF THE AREAS OUTSIDE THE ABDOMEN TO IMPROVE PLACEMENT AND CONTROL OF A SURGICAL DEVICE IN USE," filed Nov. 6, 2018;

U.S. patent application Ser. No. 16/729,747 entitled "DYNAMIC SURGICAL VISUALIZATION SYSTEMS," filed Dec. 31, 2019;

U.S. patent application Ser. No. 16/729,778 entitled "SYSTEM AND METHOD FOR DETERMINING, ADJUSTING, AND MANAGING RESECTION MARGIN ABOUT A SUBJECT TISSUE," filed Dec. 31, 2019;

U.S. patent application Ser. No. 16/729,807 entitled METHOD OF USING IMAGING DEVICES IN SURGERY, filed Dec. 31, 2019;

U.S. patent application Ser. No. 15/940,654, entitled SURGICAL HUB SITUATIONAL AWARENESS, filed Mar. 29, 2018;

U.S. patent application Ser. No. 15/940,671, titled SURGICAL HUB SPATIAL AWARENESS TO DETERMINE DEVICES IN OPERATING THEATER, which was filed on Mar. 29, 2018;

U.S. patent application Ser. No. 15/940,704, titled USE OF LASER LIGHT AND RED-GREEN-BLUE COLORATION TO DETERMINE PROPERTIES OF BACK SCATTERED LIGHT, which was filed on Mar. 29, 2018;

U.S. patent application Ser. No. 16/182,290, entitled "SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION," filed Nov. 6, 2018;

U.S. Pat. No. 9,011,427, entitled SURGICAL, INSTRUMENT WITH SAFETY GLASSES, issued on Apr. 21, 2015;

U.S. Pat. No. 9,123,155, titled APPARATUS AND METHOD FOR USING AUGMENTED REALITY VISION SYSTEM IN SURGICAL PROCEDURES, which issued on Sep. 1, 2015;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018; and U.S. patent application Ser. No. 16/182,246, titled ADJUSTMENTS BASED ON AIRBORNE PARTICLE PROPERTIES, filed Nov. 6, 2018.

Figure 1A:
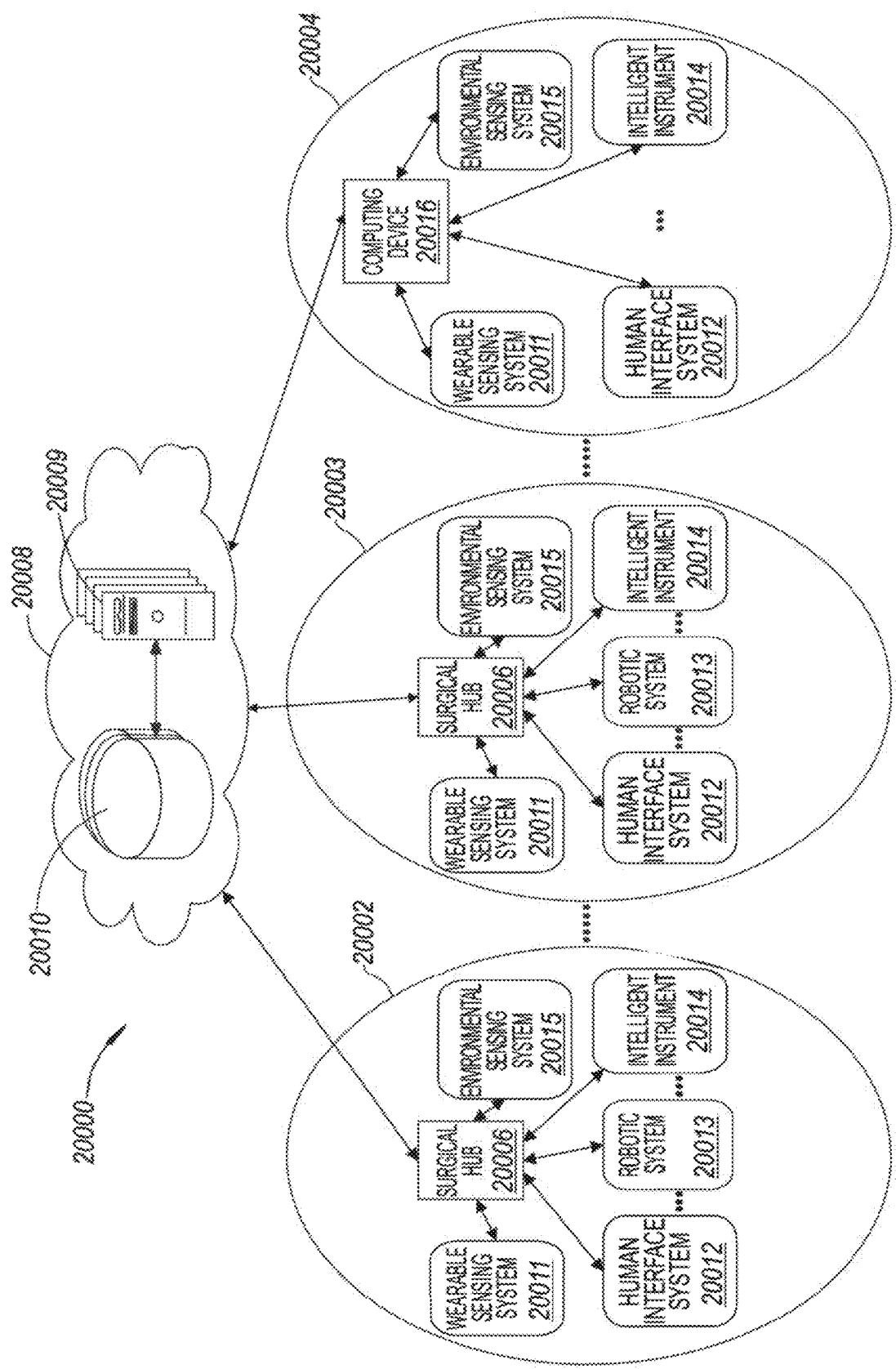
FIG. 1 is a block diagram of a computer-implemented patient and surgeon monitoring system.

FIG. 1A is a block diagram of a computer-implemented patient and surgeon monitoring system 20000. The patient and surgeon monitoring system 20000 may include one or inure surgeon monitoring systems 20002 and a one or more patient monitoring systems (e.g., one or more controlled patient monitoring systems 20003 and one or more uncontrolled patient monitoring systems 20004). Each surgeon monitoring system 20002 may include a computer-implemented interactive surgical system. Each surgeon monitoring system 20002 may include at least one of the following: a surgical hub 20006 in communication with a cloud computing system 20008, for example, as described in FIG. 2A. Each of the patient monitoring systems may include at least one of the following: a surgical hub 20006 or a computing device 20016 in communication with a could computing system 20008, for example, as further described in FIG. 2B and FIG. 2G. The cloud computing system 20008 may include at least one remote cloud server 20009 and at least one remote cloud storage unit 20010. Each of the surgeon monitoring systems 20002, the controlled patient monitoring systems 20003, or the uncontrolled patient monitoring systems 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more surgeon sensing systems, and/or one or more patient sensing systems. The environmental sensing system 20015 may include one or inure devices, for example, used for measuring one or more environmental attributes, for example, as further described in FIG. 2A. The robotic system 20013 (same as 20034 in FIG. 2A) may include a plurality of devices used for performing a surgical procedure, for example, as further described in FIG. 2A.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 200111. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

Figure 1B:
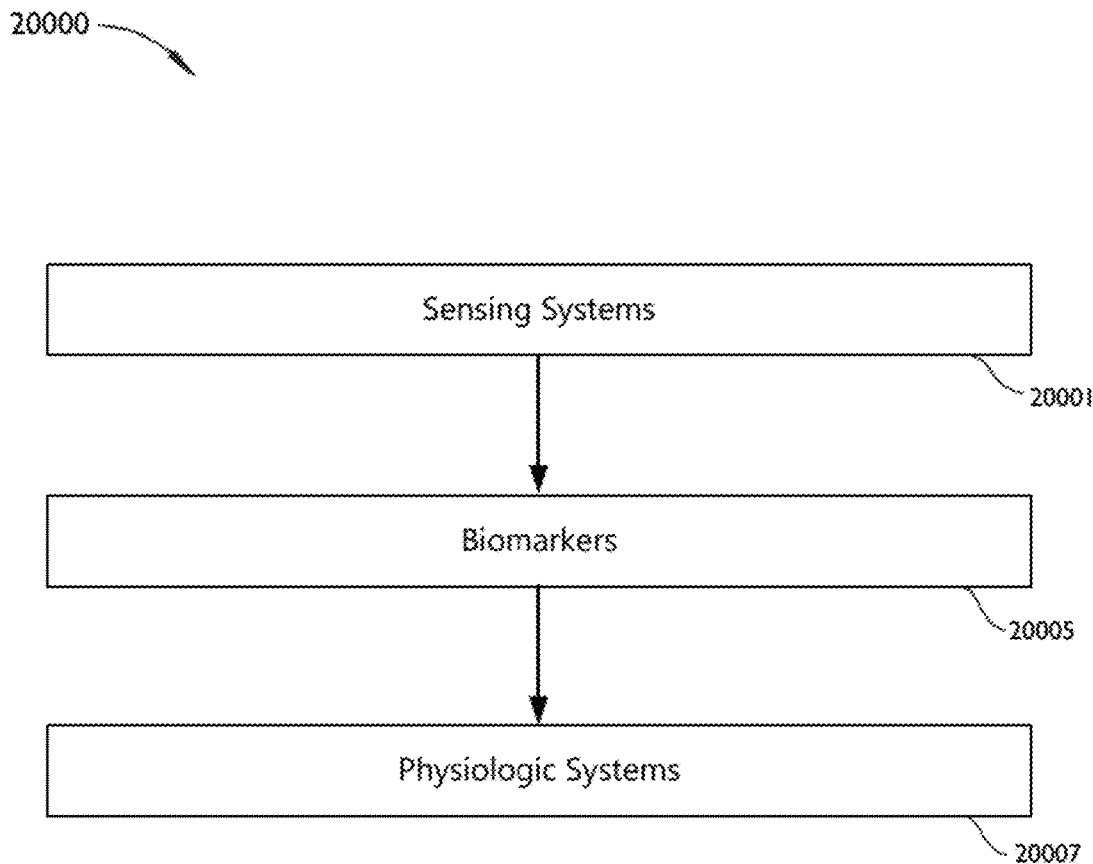

FIG. 1B is a block diagram of an example relationship among sensing systems 20001, biomarkers 20005, and physiologic systems 20007. The relationship may be employed in the computer-implemented patient and surgeon monitoring system 20000 and in the systems, devices, and methods disclosed herein. For example, the sensing systems 20001 may include the wearable sensing system 20011 which may include one or more surgeon sensing systems and one of more patient sensing systems) and the environmental sensing system 20015 as discussed in FIG. 1A. The one or more sensing systems 20001 may measure data relating to various biomarkers 20005. The one or more sensing systems 20001 may measure the biomarkers 20005 using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers 20005 as described herein using one of more of the following sensing technologies: photoplethysmography, electrocardiography, electroencephalography, colorimetry, impedimentary, potentiometry, amperometry, etc.

The biomarkers 20005 measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers 20005 may relate to physiologic systems 20007, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and surgeon monitoring system 20000, for example. The information from the biomarkers may be determined and/or used by the computer-implemented patient and surgeon monitoring system 20000 to improve said systems and/or to improve patient outcomes, for example.

Figure 2A:
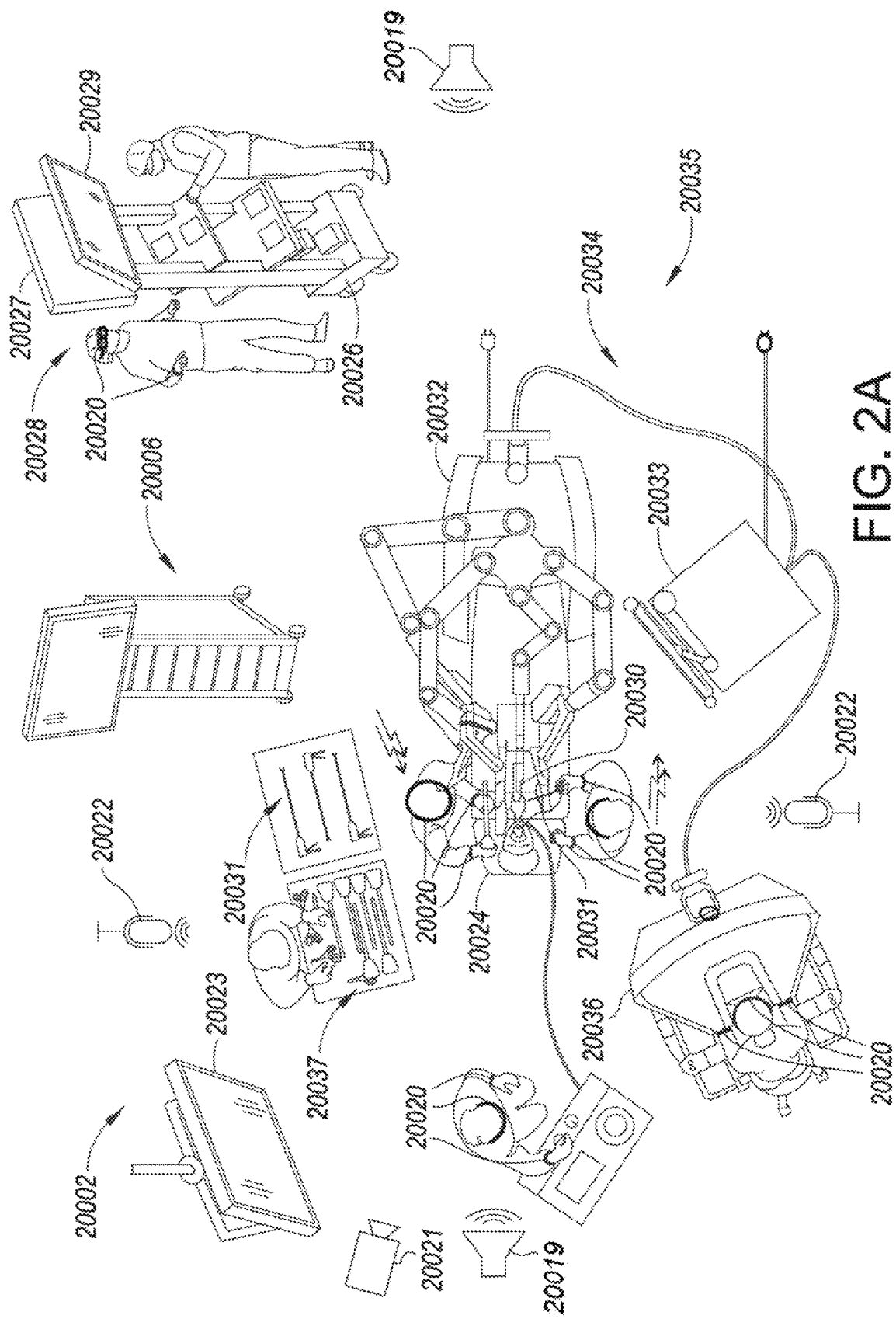
FIG. 2A shows an example of a surgeon monitoring system in a surgical operating room.

FIG. 2A shows an example of a surgeon monitoring system 20002 in a surgical operating room. As illustrated in FIG. 2A, a patient is being operated on by one or more health care professionals (HCPs). The HCPs are being monitored by one or more surgeon sensing systems 20020 worn by the HCPs. The HCPs and the environment surrounding the HCPs may also be monitored by one or more environmental sensing systems including, for example, a set of cameras 20021, a set of microphones 20022, and other sensors, etc. that may be deployed in the operating room. The surgeon sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2A, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2A, a surgical instrument 20031 is being used in the surgical procedure as part of the surgeon monitoring system 20002. The hub 20006 may be configured to coordinate in flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,383), titled METHOD OF HUB COMMUNICATION, PROCESSING, STORAGE AND DISPLAY, filed Dec. 4, 2018, the disclosure of which is herein incorporated by reference in its entirety, for example.

FIG. 2A illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging deice 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared or a surgical procedure. The sterile field may include the scrubbed team members, who are properly attired, and all furniture and fixtures in the area.

Wearable sensing system 20011 illustrated in FIG. 1 may include one or more sensing systems, for example, surgeon sensing systems 20020 as shown in FIG. 2A. The surgeon sensing systems 20020 may include sensing systems to monitor and detect a set of physical states and/or a set of physiological states of a healthcare provider (HCP). An HCP may be a surgeon or one or more healthcare personnel assisting the surgeon or other healthcare service providers in general. In an example, a sensing system 20020 may measure a set of biomarkers to monitor the heart rate of an HCP. In another example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the aye raging delay of a robotic interface, for example, to minimize tremors. In an example, the surgeon sensing systems 20020 may measure one or more surgeon biomarkers associated with an HCP and send the measurement data associated with the surgeon biomarkers to the surgical hub 20006. The surgeon sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN). The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 2B:
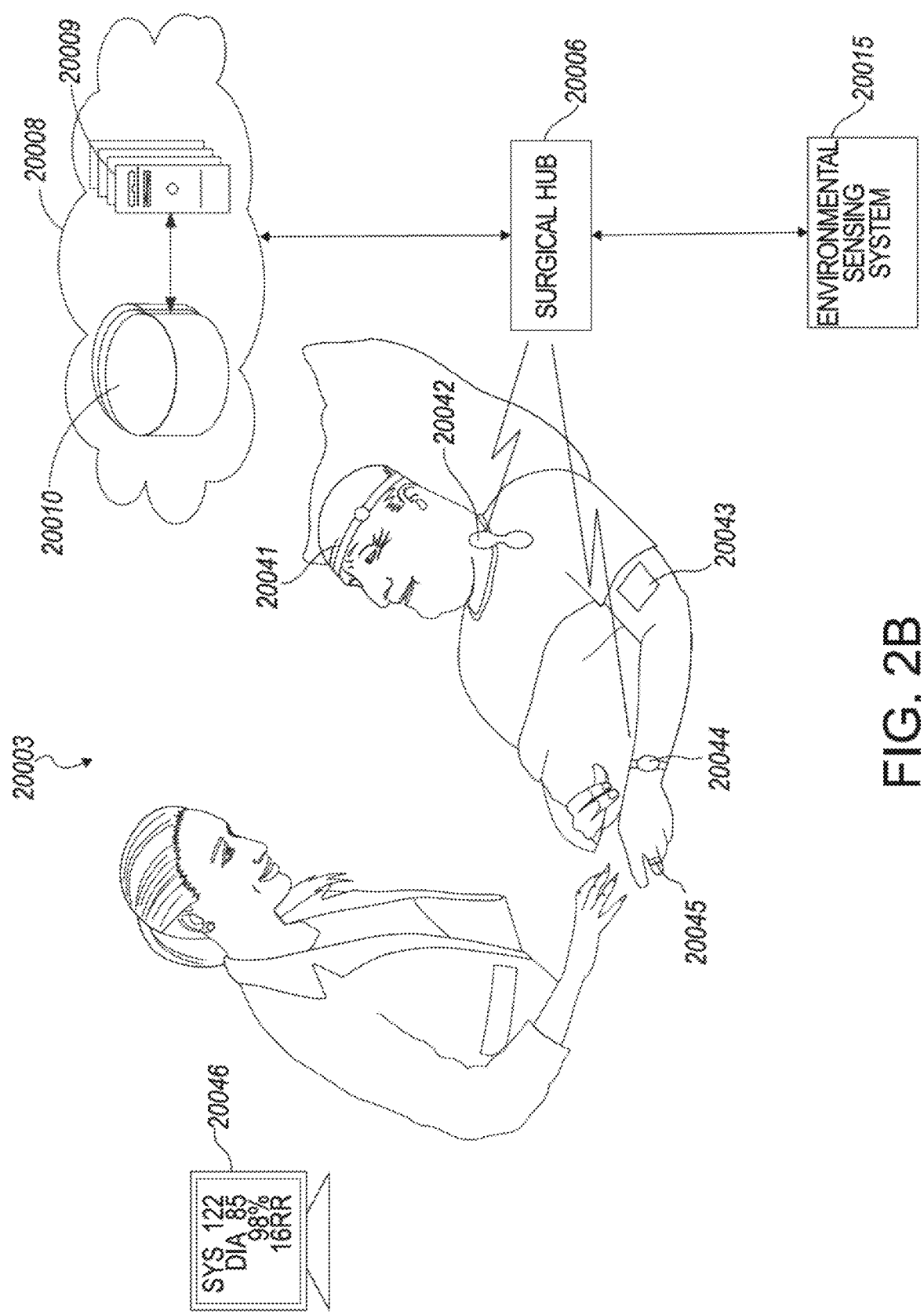
FIG. 2B shows an example of a patient monitoring system (e.g., a controlled patient monitoring system).

FIG. 2B shows an example of a patient monitoring system 20003 (e.g., a controlled patient monitoring system). As illustrated in FIG. 2B, a patient in a controlled environment (e.g., in a hospital recovery room) may be monitored by a plurality of sensing systems (e.g., patient sensing systems 20041). A patient sensing system 20041 (e.g., a head band) may be used to measure an electroencephalogram (EEG) to measure electrical activity of the brain of a patient. A patient sensing system 20042 may be used to measure various biomarkers of the patient including, for example, heart rate, VO2 level, etc. A patient sensing system 20043 (e.g., flexible patch attached to the patient's skin) may be used to measure sweat lactate and/or potassium levels by analyzing small amounts of sweat that is captured from the surface of the skin using microfluidic channels. A patient sensing system 20044 (e.g., a wristband or a watch) may be used to measure blood pressure, heart rate, heart rate variability, VO2 levels, etc. using various techniques, as described herein. A patient sensing system 20045 (e.g., a ring on finger) may be used to measure peripheral temperature, heart rate, heart rate variability, VO2 levels, etc. using various techniques, as described herein. The patient sensing systems 20041-20045 may use a radio frequency (RF) link to be in communication with the surgical hub 20006. The patient sensing systems 20041-20045 may use one or more of the following RE protocols for communication with the surgical hub 20006: Bluetooth, Bluetooth Low-Energy (BLE), Bluetooth Smart, Zigbee, Z-wave, IPv6 Low-power wireless Personal Area Network (6LoWPAN), Thread, etc.

The sensing systems 20041-20045 may be in communication with a surgical hub 20006, which in turn may be in communication with a remote server 20009 of the remote cloud computing system 20008. The surgical hub 20006 is also in communication with an HID 20046. The HID 20046 may display measured data associated with one or more patient biomarkers. For example, the HID 20046 may display blood pressure, Oxygen saturation level, respiratory rate, etc. The HID 20046 may display notifications for the patient or an HCP providing information about the patient, for example, information about a recovery milestone or a complication. In an example, the information about a recovery milestone or a complication may be associated with a surgical procedure the patient may have undergone. In an example, the HID 20046 may display instructions for the patient to perform an activity. For example, the HID 20046 may display inhaling and exhaling instructions. In an example the HID 20046 may be part of a sensing system.

As illustrated in FIG. 2B, the patient and the environment surrounding the patient may be monitored by one or more environmental sensing systems 20015 including, for example, a microphone (e.g., for detecting ambient noise associated with or around a patient), a temperature/humidity sensor, a camera for detecting breathing patterns of the patient, etc. The environmental sensing systems 20015 may be in communication with the surgical hub 20006, which in turn is in communication a remote server 20009 of the remote cloud computing system 20008.

In an example, a patient sensing system 20044 may receive a notification information from the surgical hub 20006 for displaying on a display unit or an HID of the patient sensing system 20044. The notification information may include a notification about a recovery milestone or a notification about a complication, for example, in case of post-surgical recovery. In an example, the notification information may include an actionable severity level associated with the notification. The patient sensing system 20044 may display the notification and the actionable severity level to the patient. The patient sensing system may alert the patient using a haptic feedback. The visual notification and/or the haptic notification may be accompanied by an audible notification prompting the patient to pay attention to the visual notification provided on the display unit of the sensing system.

Figure 2C:
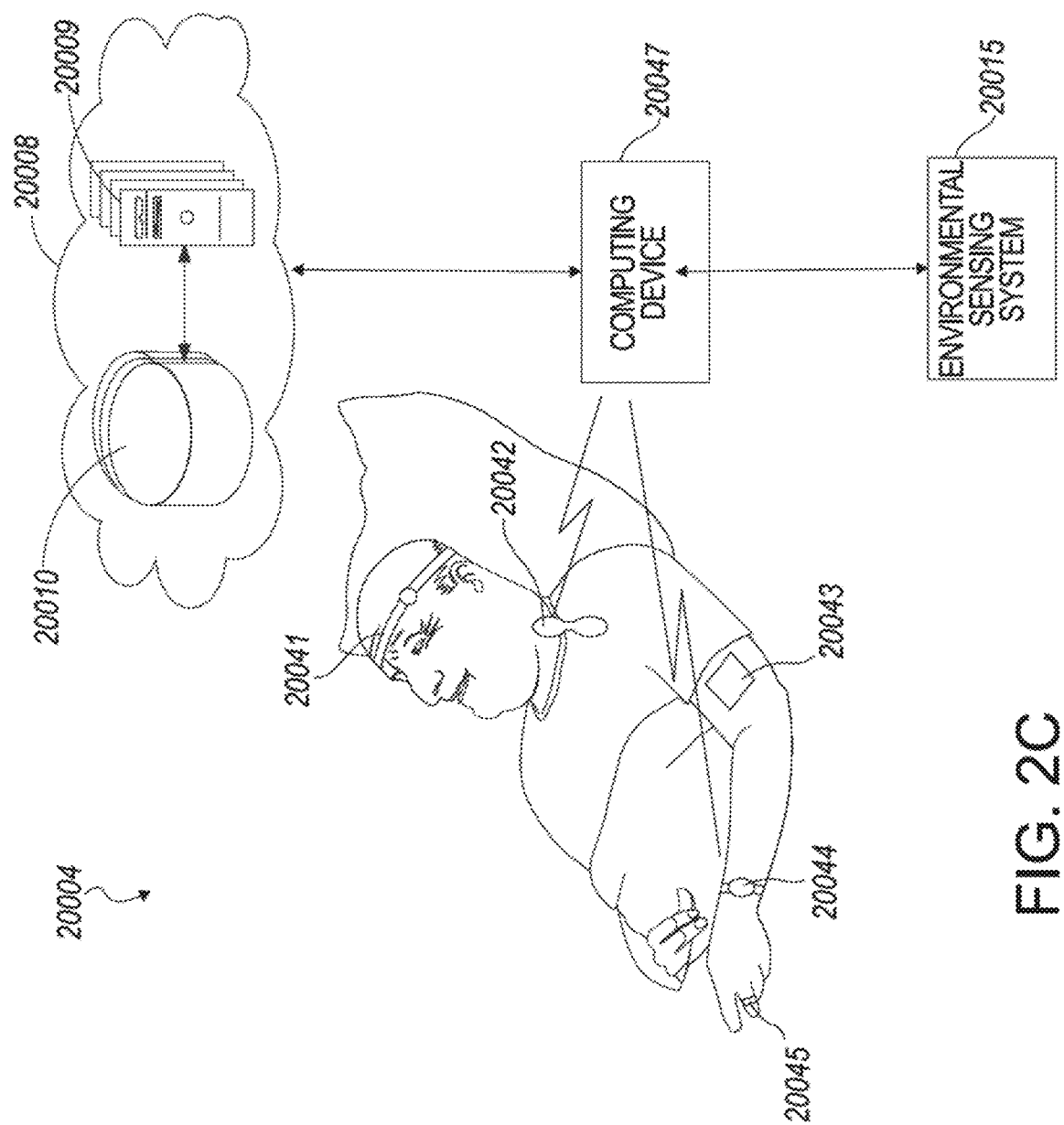
FIG. 2C shows an example of a patient monitoring system (e.g., an uncontrolled patient monitoring system).

FIG. 2C shows an example of a patient monitoring system (e.g., an uncontrolled monitoring system 20004). As illustrated in FIG. 2C, a patient in an uncontrolled environment (e.g., a patient's residence) is being monitored by a plurality of patient sensing systems 20041-20045. The patient sensing systems 20041-20045 may measure and/or monitor measurement data associated with one or more patient biomarkers. For example, a patient sensing system 20041, a head band, may be used to measure an electroencephalogram (EEG). Other patient sensing systems 20042, 20043, 20044, and 20045 are examples where various patient biomarkers are monitored, measured, and/or reported, as described in FIG. 2B. One or more of the patient sensing systems 20041-20045 may be send the measured data associated with the patient biomarkers being monitored to the computing device 20047, which in turn may be in communication with a remote server 20009 of the remote cloud computing system 20008. The patient sensing systems 20041-20045 may use a radio frequency (RF) link to be in communication with a computing device 20047 (e.g., a smart phone, a tablet, etc.). The patient sensing systems 20041-20045 may use one or more of the following RF protocols for communication with the computing device 20047: Bluetooth, Bluetooth Low-Energy (BLE), Bluetooth Smart, Zigbee, Z-wave, IPv6 Low-power wireless Personal Area Network (6LoWPAN), Thread, etc. In an example, the patient sensing systems 20041-20045 may be connected to the computing device 20047 via a wireless router, a wireless hub, or a wireless bridge.

The computing device 20047 may be in communication with a remote server 20009 that is part of a cloud computing system 20008. In an example, the computing device 20047 may be in communication with a remote server 20009 via an internet service provider's cable/FIOS networking node. In an example, a patient sensing system may be in direct communication with a remote server 20009. The computing device 20047 or the sensing system may communicate with the remote servers 20009 via a cellular transmission/reception point (TRP) or a base station using one or more of the following cellular protocols: GSM/G-PRS/EDGE (2G), UMTS/HSPA (3G), long term evolution (LTE) or 4G, LTE-Advanced (LTE-A), new radio (NR) or 5G.

In an example, a computing device 20047 may display information associated with a patient biomarker. For example, a computing device 20047 may display blood pressure, Oxygen saturation level, respiratory rate, etc. A computing device 20047 may display notifications for the patient or an HCP providing information about the patient, for example, information about a recovery milestone or a complication.

In an example, the computing device 20047 and/or the patient sensing system 20044 may receive a notification information from the surgical hub 20006 for displaying on a display unit of the computing device 20047 and/or the patient sensing system 20044. The notification information may include a notification about a recovery milestone or a notification about a complication, for example, in case of post-surgical recovery. The notification information may also include an actionable seventy level associated with the notification. The computing device 20047 and/or the sensing system 20044 may display the notification and the actionable severity level to the patient. The patient sensing system may also alert the patient using a haptic feedback. The visual notification and/or the haptic notification may be accompanies by an audible notification prompting the patient to pay attention to the visual notification provided on the display unit of the sensing system.

Figure 3:
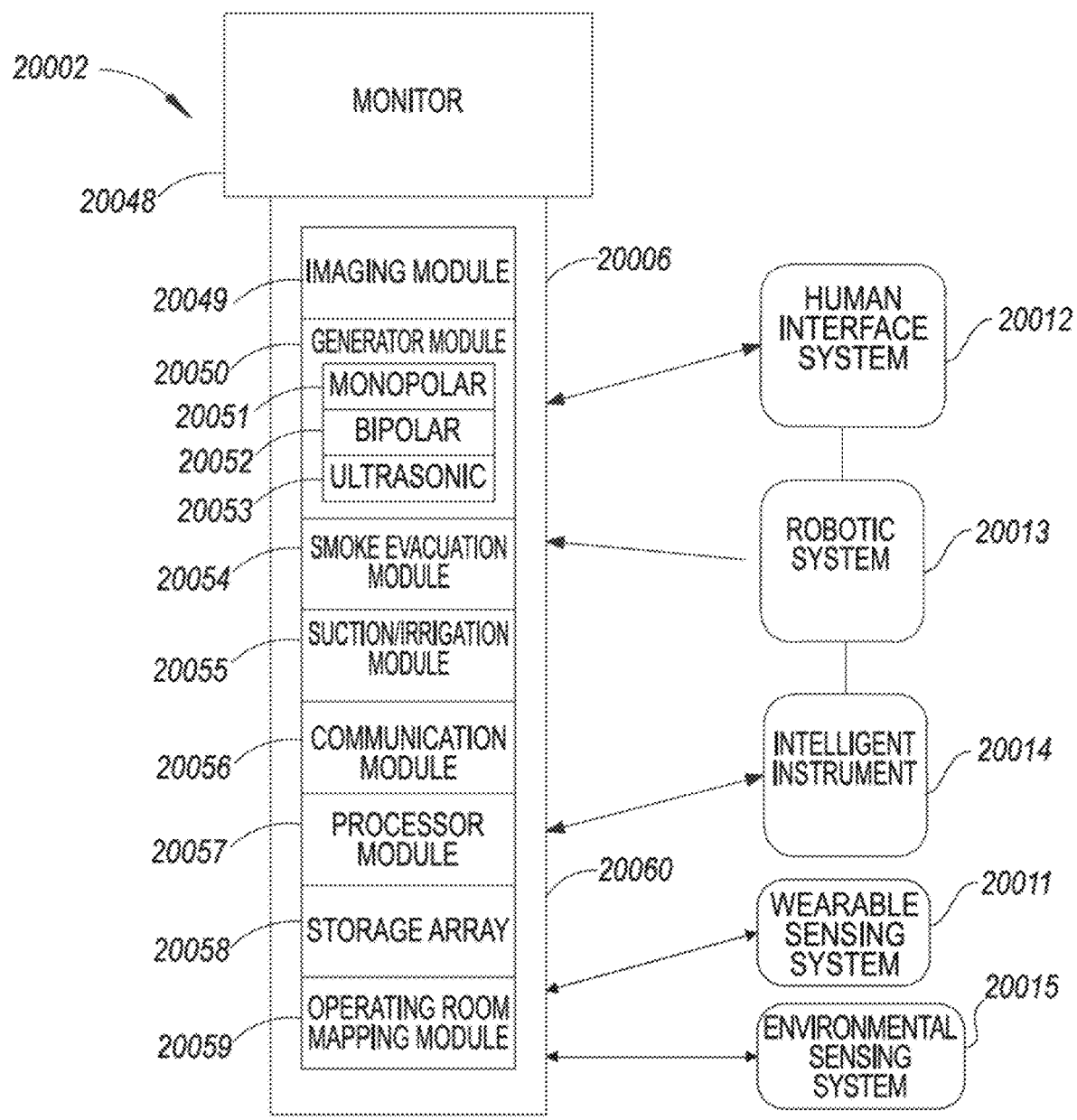
FIG. 3 illustrates an example surgical hub paired with various systems.

FIG. 3 shows an example surgeon monitoring system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy-generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the (issue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slid ably movable out of the electrical engagement with the second power and data contacts. In addition, the modular surgical enclosure also includes a communication bus between the first docking port and the second docking port, configured to facilitate communication between the first energy generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The huh modular enclosure 20060 further facilitates interactive communication between the modules 20059, 20054, and 20055. The generator module 20050 can be a generator module 20050 with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
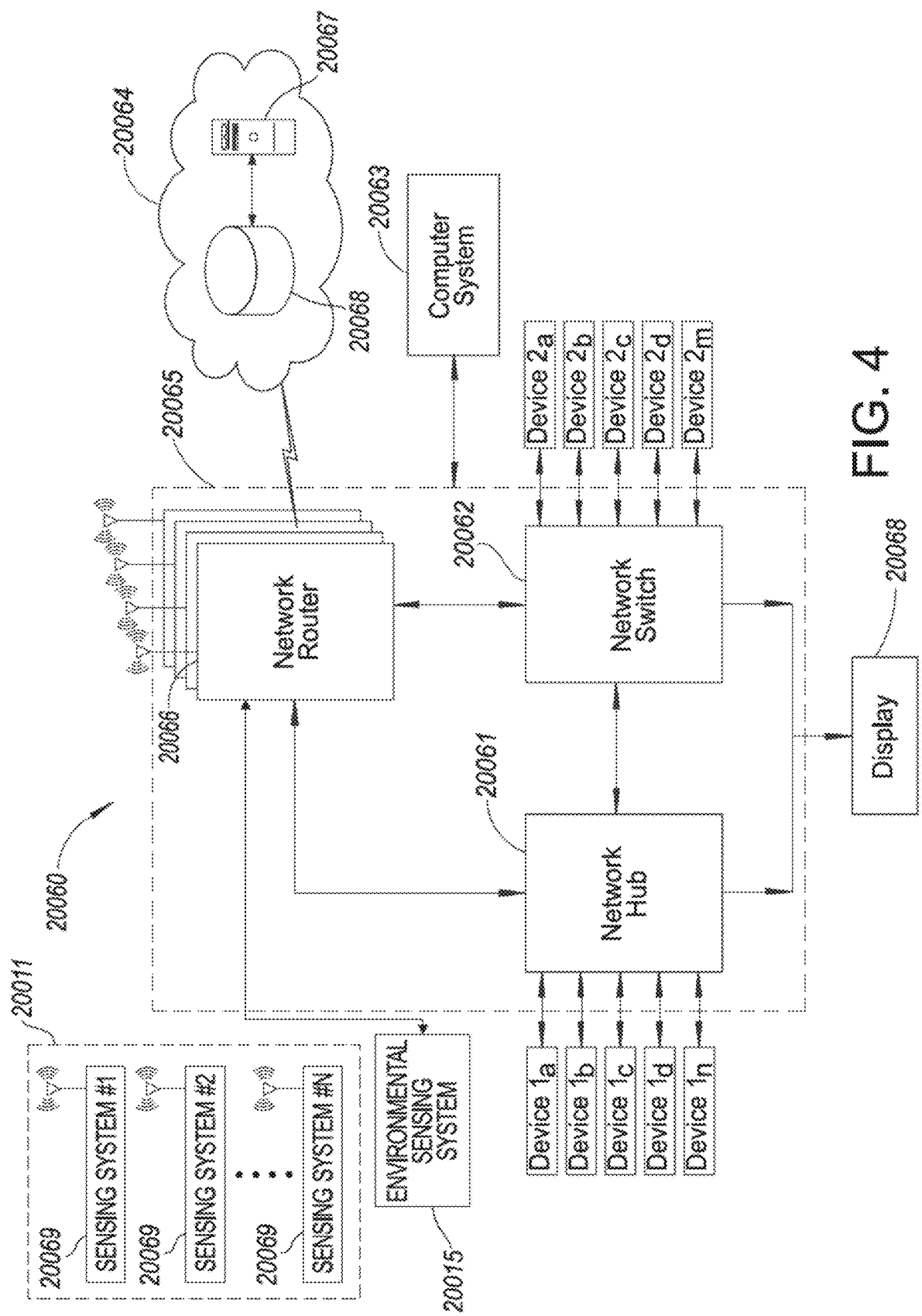
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, an environment sensing system, and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation. Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network muter 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include a surgeon sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data or measurement data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data, collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, notify a patient of a complication dining post-surgical period.

The operating theater devices 1a-113 may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the deices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connections the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and budding personal area networks (PANS). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-tetra evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
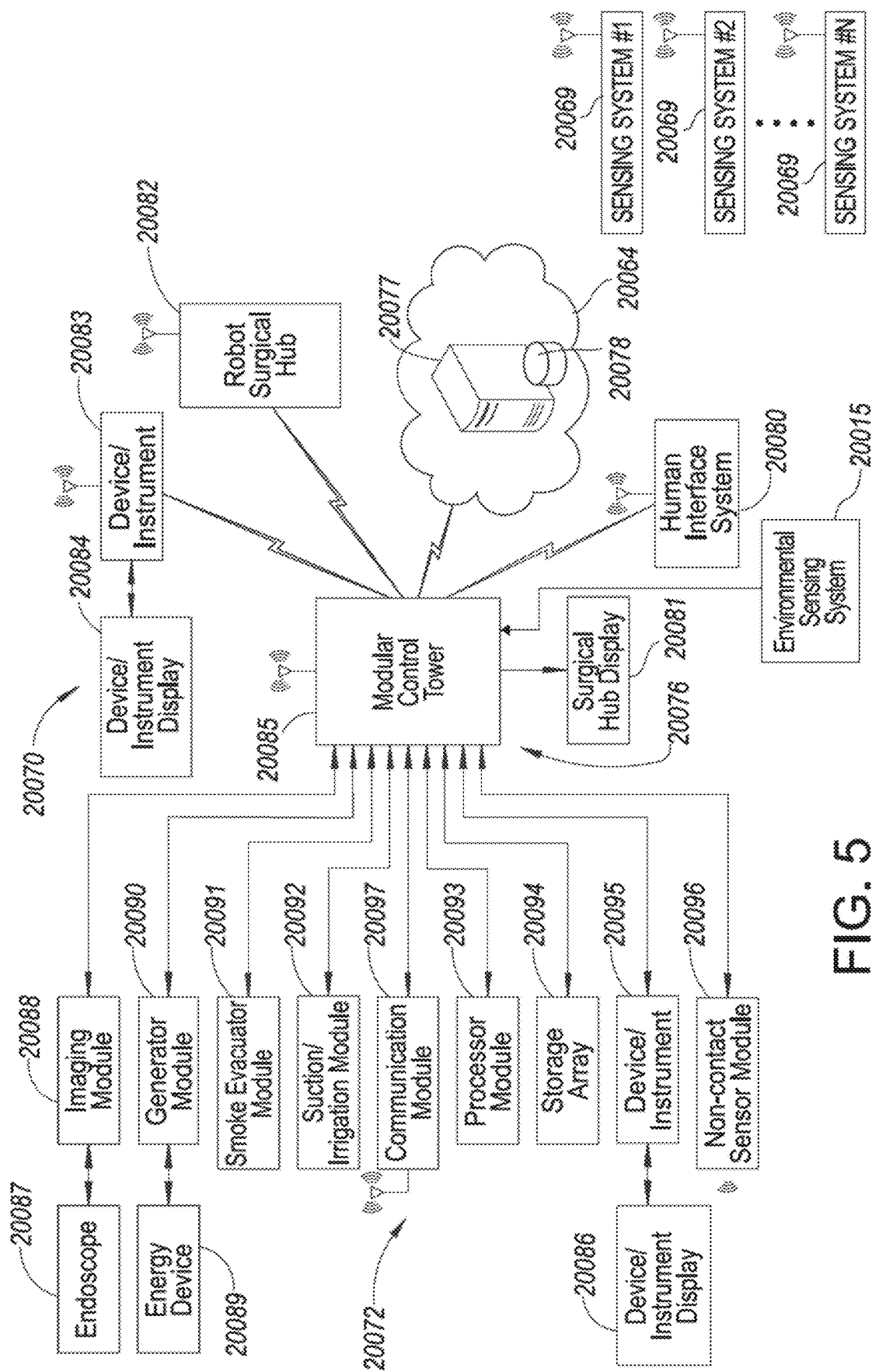
FIG. 5 illustrates an example computer-implemented interactive surgical system that may be part of a surgeon monitoring system.
Figure 6A:
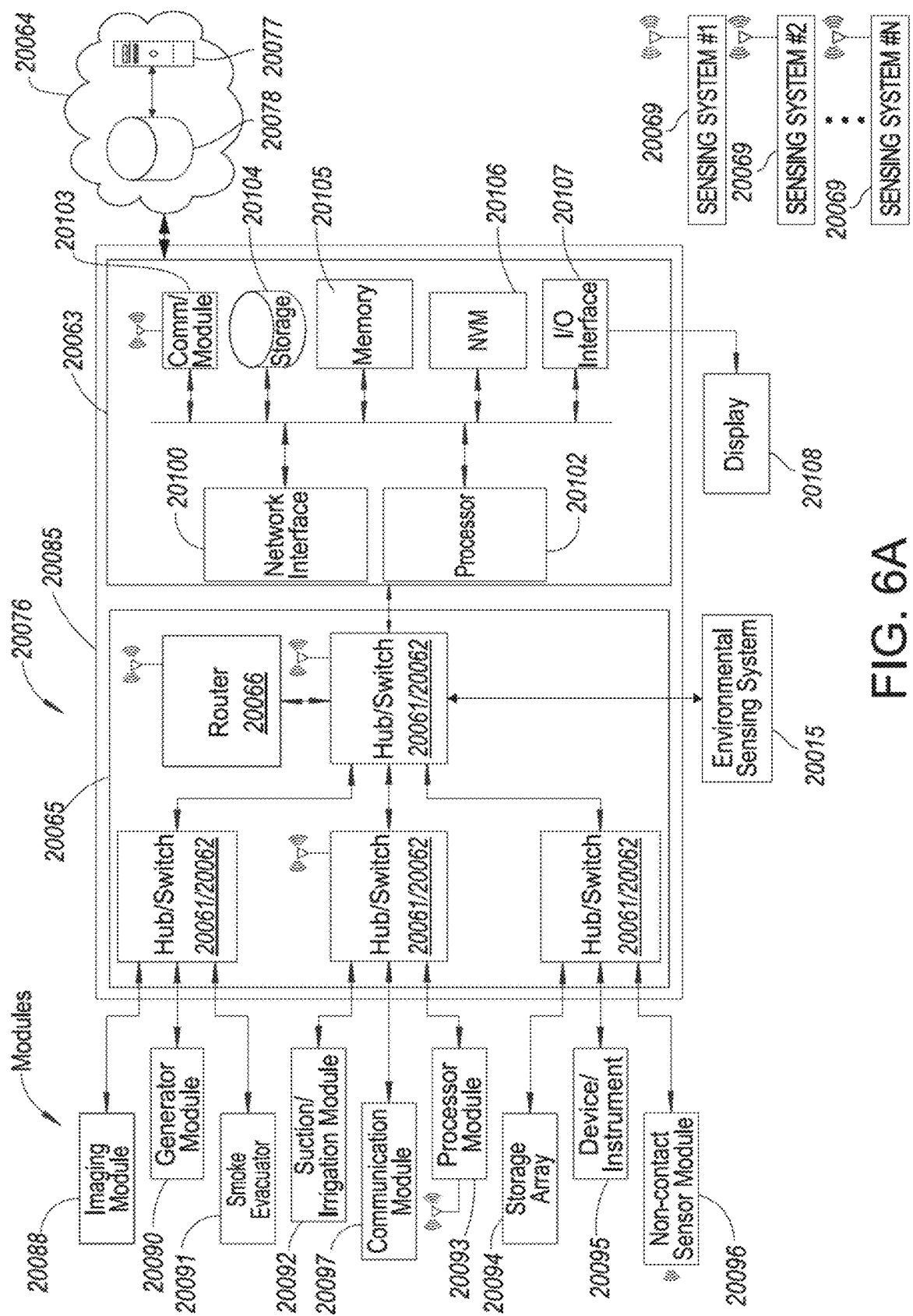
FIG. 6A illustrates a surgical hub comprising: a plurality of modules coupled to a modular control tower.

FIG. 5 illustrates a computer-implemented interactive surgical system 20070 that may be a part of the surgeon monitoring system 20002. The computer-implemented interactive surgical system 20070 is similar in many respects to the surgeon sensing system 20002. For example, the computer-implemented interactive surgical system 20070 may include one or more surgical sub-systems 20072, which are similar in many respects to the surgeon monitoring systems 20002. Each sub-surgical system 20072 includes at least one surgical hub 20076 in communication with a cloud computing system 20064 that may include a remote server 20077 and a remote storage 20078. In one aspect, the computer-implemented interactive surgical system 20070 may include a modular control tower 20085 connected to multiple operating theater devices such as sensing systems (e.g., surgeon sensing systems 20002 and/or patient sensing system 20003), intelligent surgical instruments, robots, and other computerized devices located in the operating theater. As shown in FIG. 6A, the modular control tower 20085 may include a modular communication hub 20065 coupled to a local computing system 20063.

As illustrated in the example of FIG. 5, the modular control tower 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The modular control tower 20085 may also be in communication with one or more sensing systems 20069 and an environmental sensing system 20015. The sensing systems 20069 may be connected to the modular control tower 20085 either directly via a router or via the communication module 20097. The operating theater devices may be coupled to cloud computing resources and data storage via the modular control tower 20085. A robot surgical hub 20082 also may be connected to the modular control tower 20085 and to the cloud computing resources. The devices/instruments 20095 or 20084, human interface system 20080, among others, may be coupled to the modular control tower 20085 via wired or wireless communication standards or protocols, as described herein. The human interface system 20080 may include a display sub-system and a notification sub-system. The modular control tower 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control tower 20085 in conjunction with images and overlaid images.

FIG. 6A illustrates a surgical hub 20076 comprising a plurality of modules coupled to the modular control tower 20085. As shown in FIG. 6A, the surgical hub 20076 may be connected to a generator module 20090, the smoke evacuator module 20091, suction/irrigation module 20092, and the communication module 20097. The modular control tower 20085 may comprise a modular communication hub 20065, e.g., a network connectivity device, and a computer system 20063 to provide local wireless connectivity with the sensing systems, local processing, complication monitoring, visualization, and imaging, for example. As shown in FIG. 6A, the modular communication hub 20065 may be connected in a configuration (e.g., a tiered configuration) to expand a number of modules (e.g., devices) and a number of sensing systems 20069 that may be connected to the modular communication hub 20065 and transfer data associated with the modules and/or measurement data associated with the sensing systems 20069 to the computer system 20063, cloud computing resources, or both. As shown in FIG. 6A, each of the network hubs/switches 20061/20062 in the modular communication hub 20065 may include three downstream ports and one upstream port. The upstream network hub/switch may be connected to a processor 20102 to provide a communication connection to the cloud computing resources and a local display 20108. At least one of the network/hub switches 20061/20062 in the modular communication hub 20065 may have at least one wireless interface to provided communication connection between the sensing systems 20069 and/or the devices 20095 and the cloud computing system 20064. Communication to the cloud computing system 20064 may be made either through a wired or a wireless communication channel.

The surgical hub 20076 may employ a non-contact sensor module 20096 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 20063 may comprise a processor 20102 and a network interface 20100. The processor 20102 may be coupled to a communication module 20103, storage 20104, memory 20103, non-volatile memory 20106, and input/output (I/O) interface 20107 via a system bus. The system bus can be any of several types of bus structure(s) including the memory bus or memory controller, a peripheral bus or external bus, and or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 20102 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor 20102 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 20063 also may include removable/non-removable, volatile/non-volatile computer storage media, such as for example disk storage. The disk storage can include, but is not limited to, devices like a magnetic disk drive, floppy disk drive, tape drive, Jaz, drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20003 through input device(s) coupled to the I/O interface 20107. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

Figure 6B:
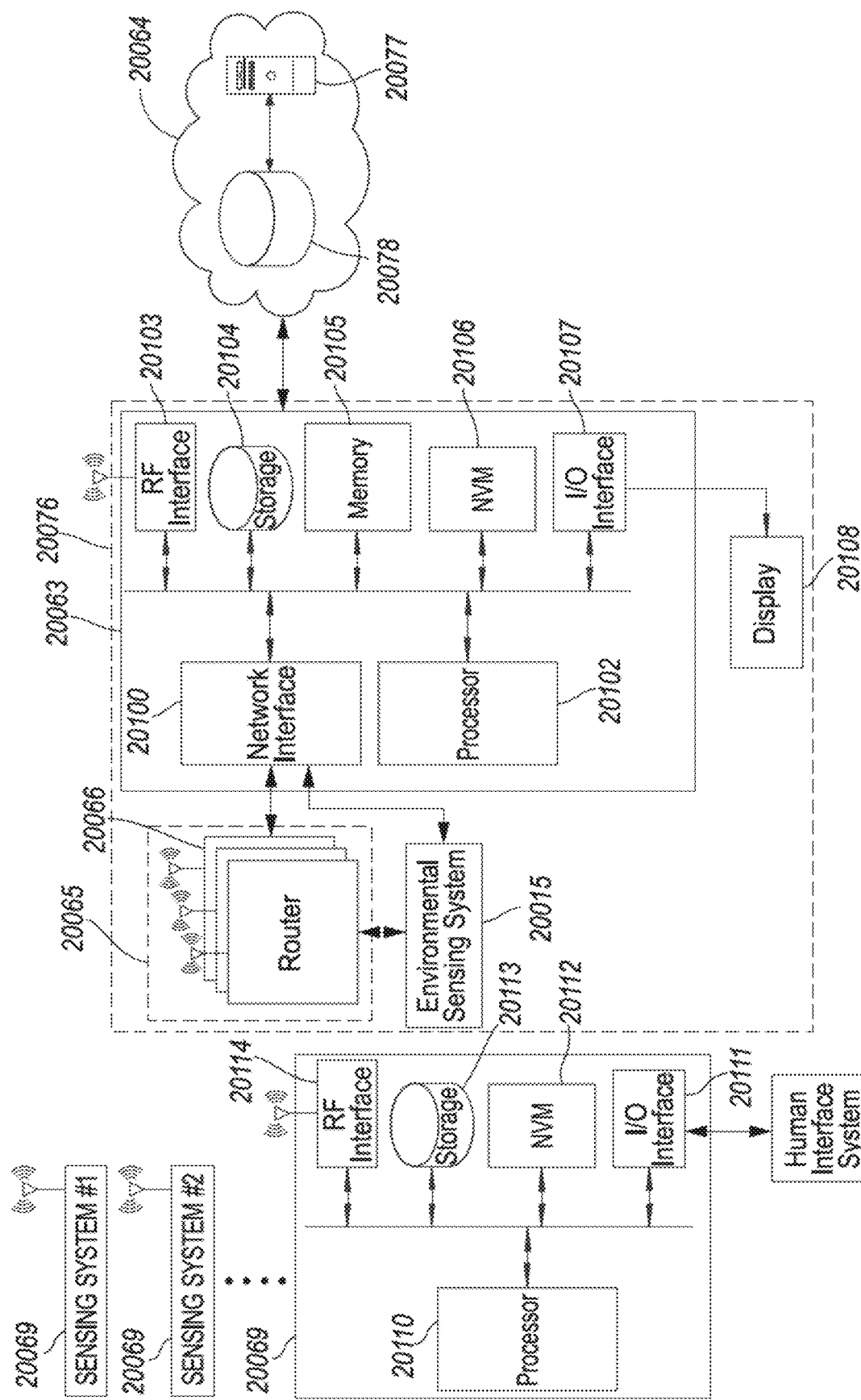
FIG. 6B illustrates an example of a controlled patient monitoring system.

In various examples, the computer system 20063 of FIG. 4, FIG. 6A and FIG. 6B, the imaging module 20088 and/or human interface system 20080, and/or the processor module 20093 of FIG. 5 and FIG. 6A may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an interface.

FIG. 6B illustrates an example of a wearable monitoring system, e.g., a controlled patient monitoring system. A controlled patient monitoring system may be the sensing system used to monitor a set of patient biomarkers when the patient is at a healthcare facility. The controlled patient monitoring system may be deployed for pre-surgical patient monitoring when a patient is being prepared for a surgical procedure, in-surgical monitoring when a patient is being operated on, or in post-surgical monitoring, for example, when a patient is recovering, etc. As illustrated in FIG. 6B, a controlled patient monitoring system may include a surgical hub system 20076, which may include one or more routers 20066 of the modular communication hub 20065 and a computer system 20063. The routers 20065 may include wireless routers, wired switches, wired routers, wired or wireless networking hubs, etc. In an example, the routers 20065 may be part of the infrastructure. The computing system 20063 may provide local processing for monitoring various biomarkers associated with a patient or a surgeon, and a notification mechanism to indicate to the patient and/or a healthcare provided (HCP) that a milestone (e.g., a recovery milestone) is met or a complication is detected. The computing system 20063 of the surgical hub system 20076 may also be used to generate a severity level associated with the notification, for example, a notification that a complication has been detected.

Figure 6C:
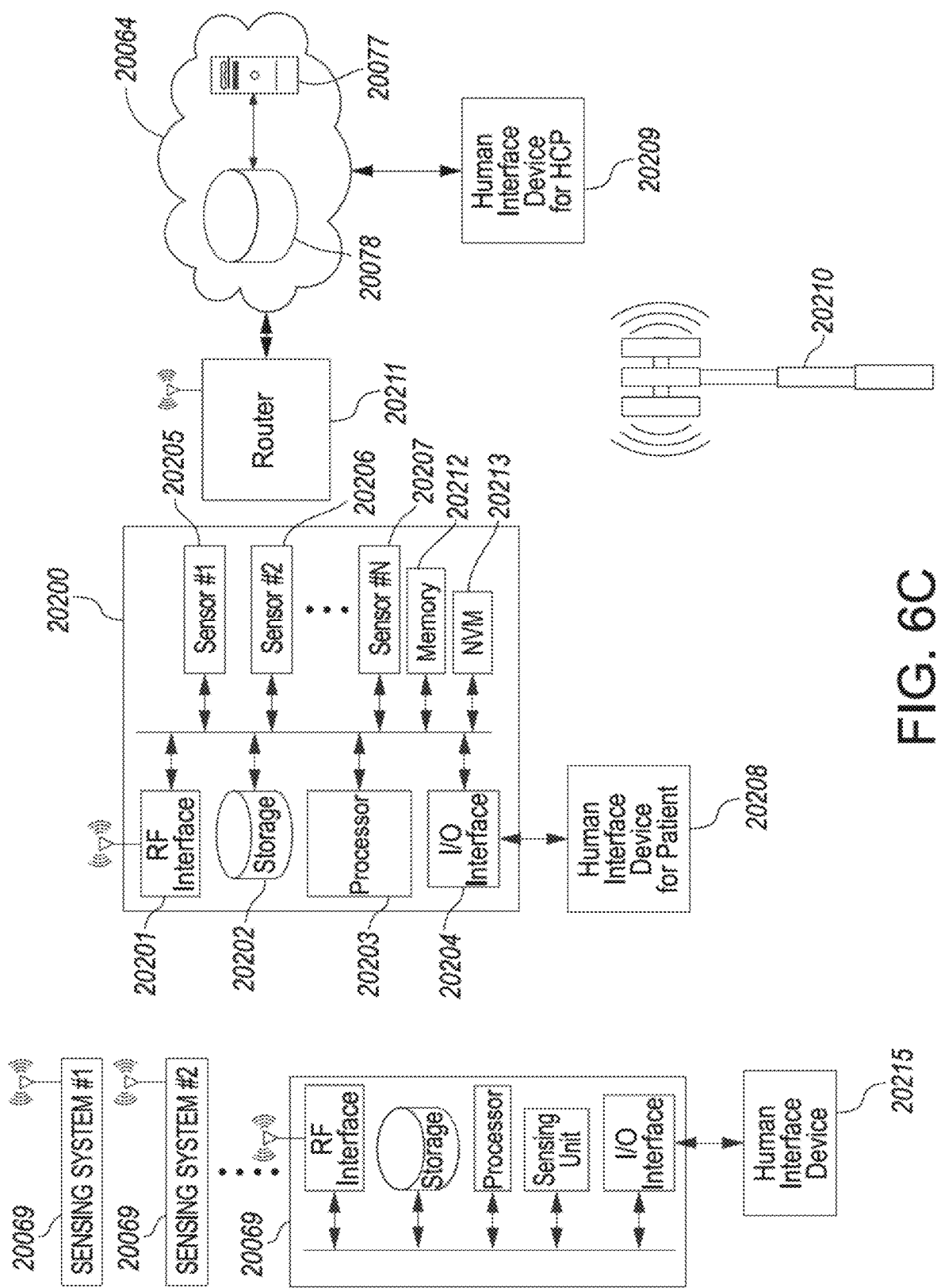
FIG. 6C illustrates an example of an uncontrolled patient monitoring system.
Figure 7A:
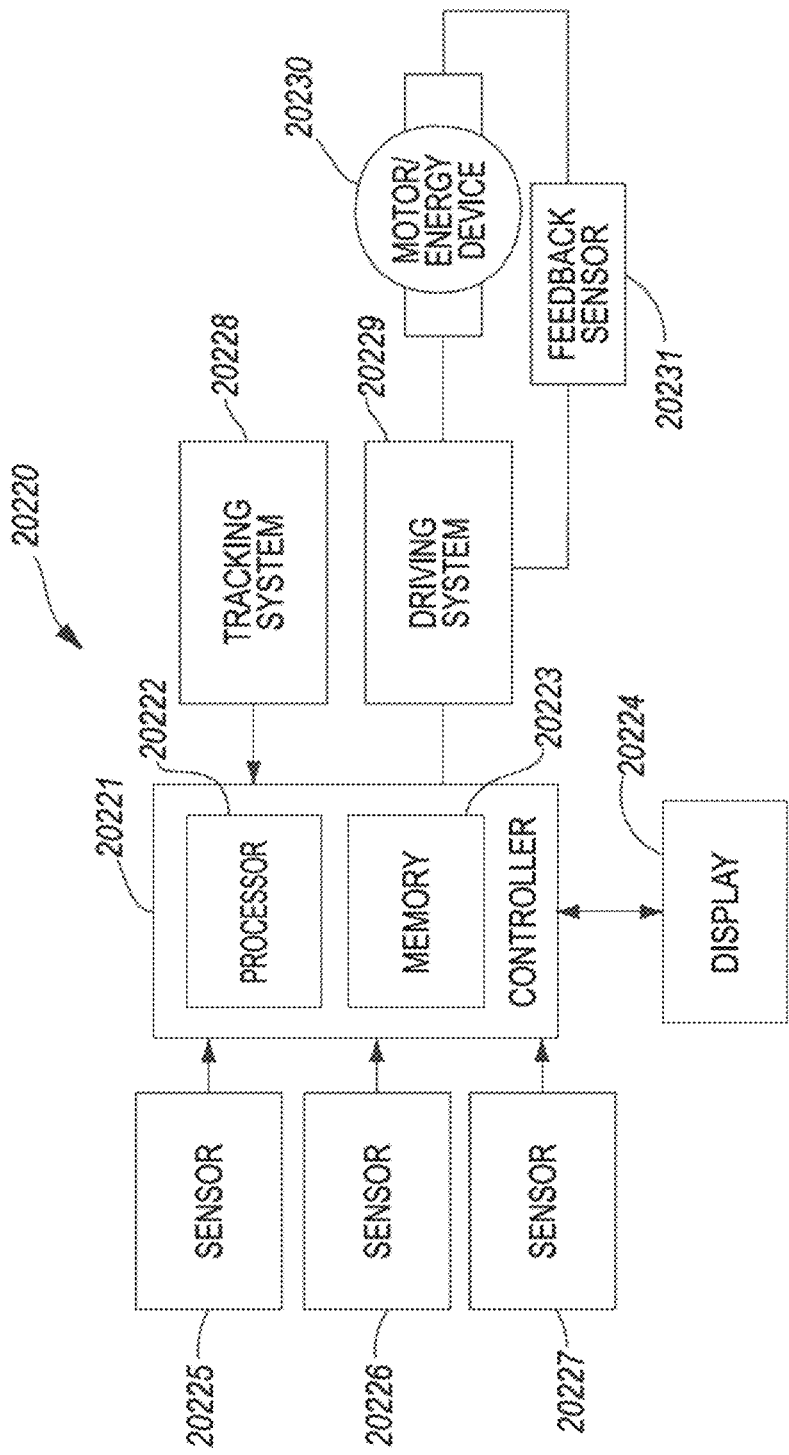
FIG. 7A illustrates a logic diagram of a control system of a surgical instrument or a tool.
Figure 7B:
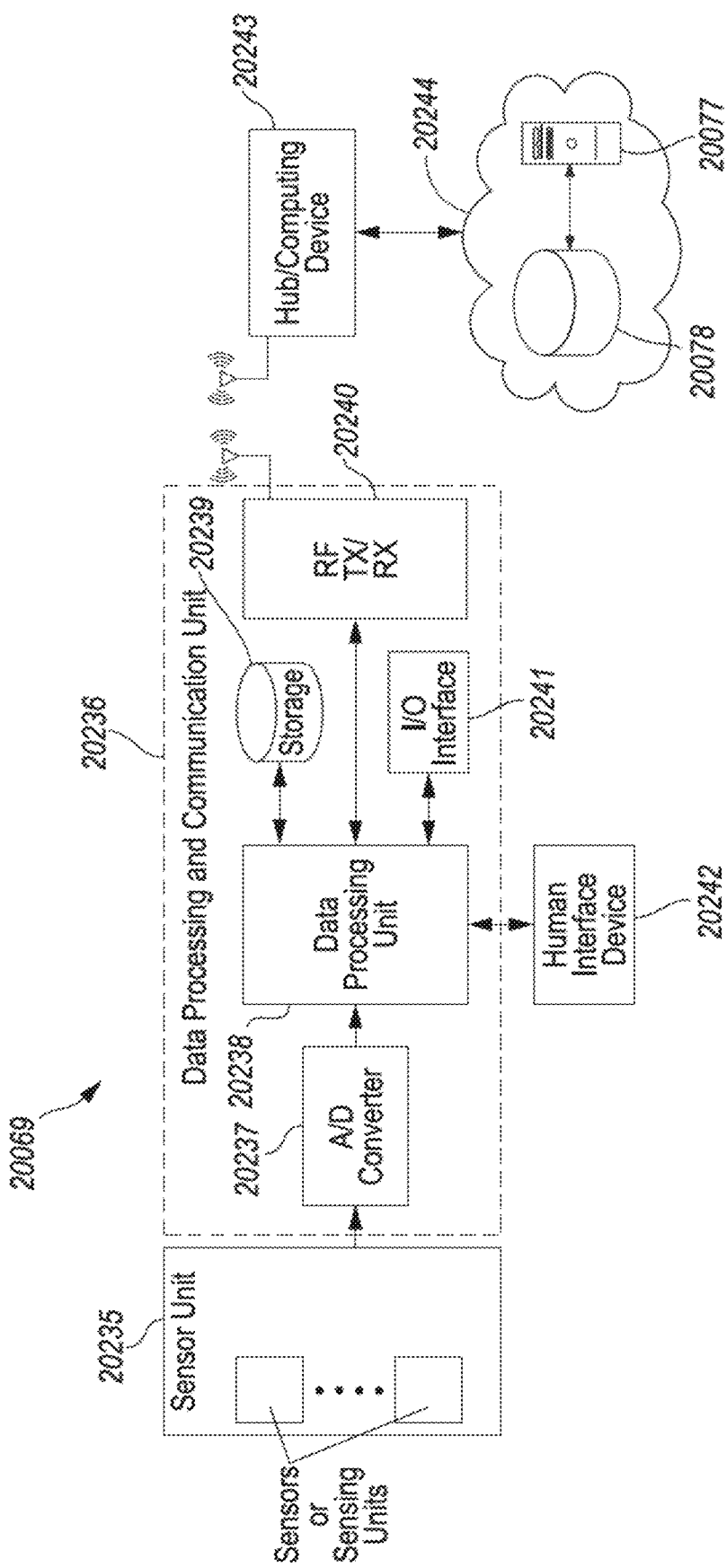
FIG. 7B shows an exemplary sensing system with a sensor unit and a data processing and communication unit.
Figure 7C:
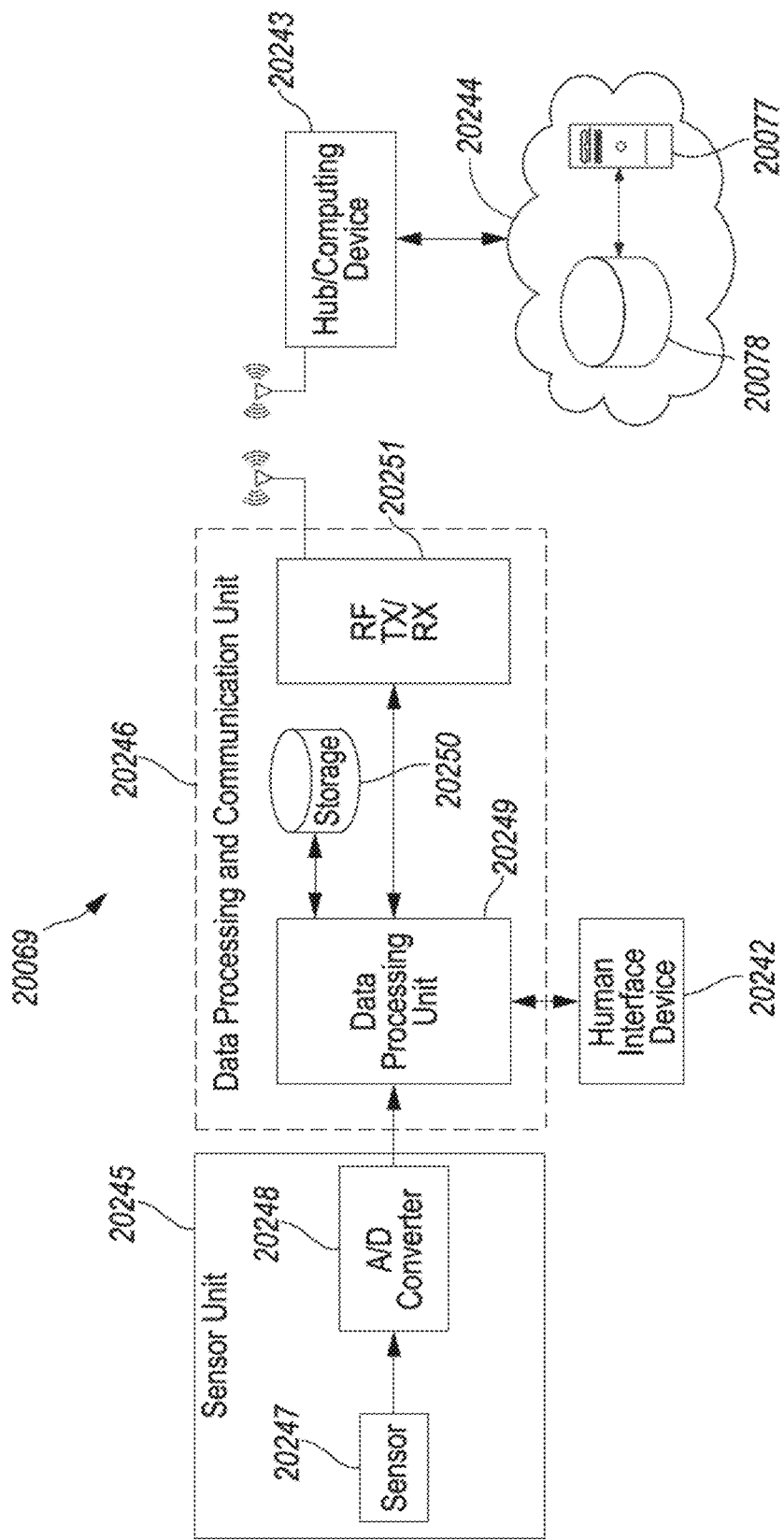
FIG. 7C shows an exemplary sensing system with a sensor unit and a data processing and communication unit.
Figure 7D:
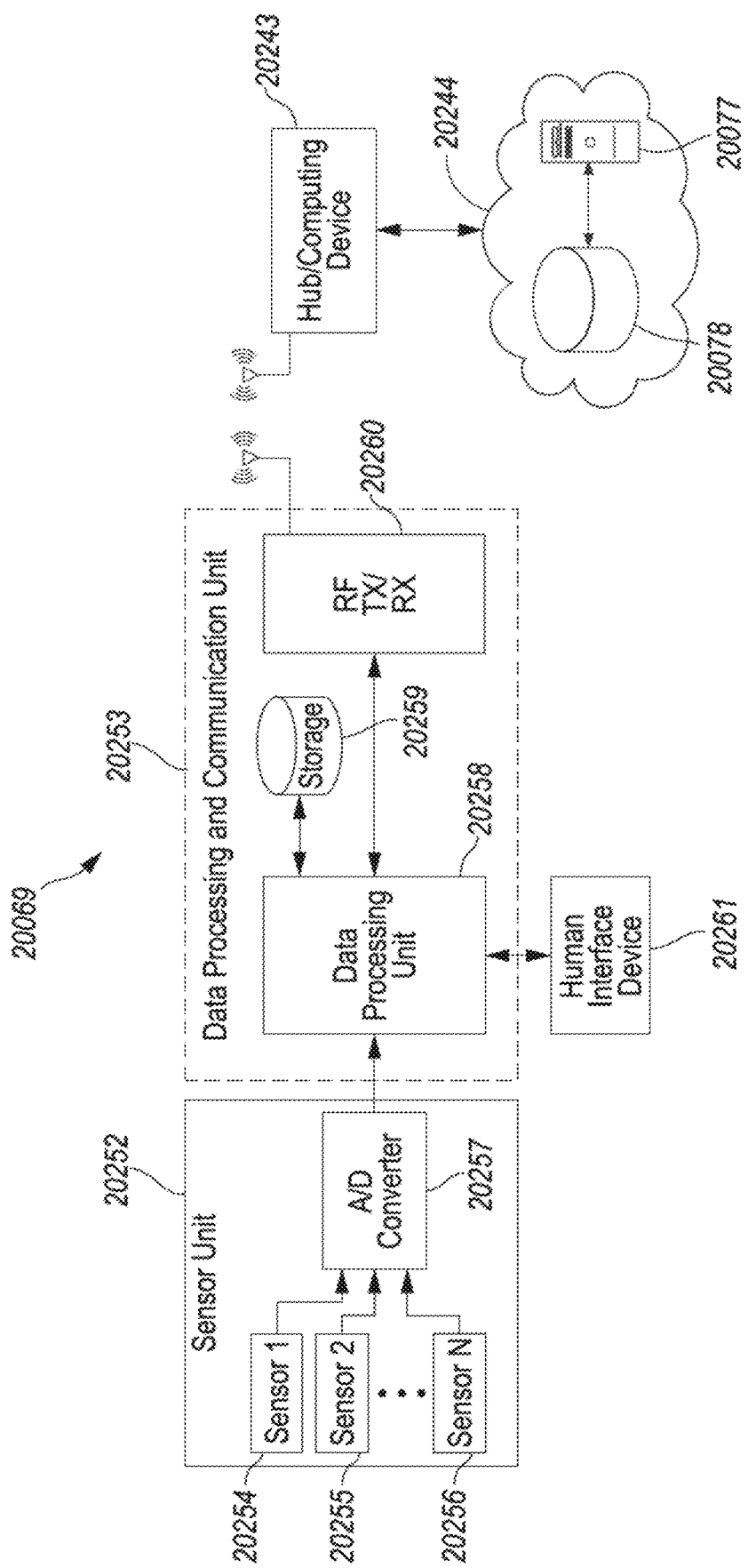
FIG. 7D shows an exemplary sensing system with a sensor unit and a data processing and communication unit.

The computing system 20063 of FIG. 4, FIG. 6B, the computing device 20200 of FIG. 6C, the hub/computing device 20243 of FIG. 7B, FIG. 7C, or FIG. 7D may be a surgical computing system or a hub device, a laptop, a tablet, a smart phone, etc.

As shown in FIG. 6B, a set of sensing systems 20069 and/or an environmental sensing system 20015 (as described in FIG. 2A) may be connected to the surgical hub system 20076 via the routers 20065. The routers 20065 may also provide a direct communication connection between the sensing systems 20069 and the cloud computing system 20064, for ex ample, without involving the local computer system 20063 of the surgical hub system 20076. Communication from the surgical hub system 20076 to the cloud 20064 may be made either through a wired or a wireless communication channel.

As shown in FIG. 6B, the computer system 20063 may include a processor 20102 and a network interface 20100. The processor 20102 may be coupled to a radio frequency (RF) interface or a communication module 20103, storage 20104, memory 20105, non-volatile memory 20106, and input/output interface 20107 via a system bus, as described in FIG. 6A. The computer system 20063 may be connected with a local display unit 20108. In some examples, the display unit 20108 may be replaced by a HID. Details about the hardware and software components of the computer system are provided in FIG. 6A.

As shown in FIG. 6B, a sensing system 20069 may include a processor 20110. The processor 20110 may be coupled to a radio frequency (RF) interface 20114, storage 20113, memory (e.g., a non-volatile memory) 20112, and I/O interface 20111 via a system bus. The system bus can be any of several types of bus structure(s) including the memory bus or memory controller, a peripheral bus or external bus, and/or a local bus, as described herein. The processor 20110 may be any single-core or multicore processor as described herein.

It is to be appreciated that the sensing system 20069 may include software that acts as an intermediary between sensing system users and the computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

The sensing system 20069 may be connected to a human interface system 20115. The human interface system 20115 may be a touch screen display. The human interface system 20115 may include a human interface display for displaying information associated with a surgeon biomarker and/or a patient biomarker, display a prompt for a user action by a patient or a surgeon, or display a notification to a patient or a surgeon indicating information about a recovery millstone or a complication. The human interface system 20115 may be used to receive input from a patient or a surgeon. Other human interface systems may be connected to the sensing system 20069 via the I/O interface 20111. For example, the human interface device 20115 may include devices for providing a haptic feedback as a mechanism for prompting a user to pay attention to a notification that may be displayed on a display unit.

The sensing system 20069 may operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. The remote computer(s) may be logically connected to the computer system through a network interface. The network interface may encompass communication networks such as local area networks (LANs), wide area networks (WANs), and/or mobile networks. LAN technologies may include Fiber Distributed Data Interface (FDDI), Copper Distributed Data Interface (CDDI), Ethernet/IEEE 802.3, Token Ring/IEEE 802.5, Wi-Fi/IEEE 802.11, and the like. WAN technologies may include, but are not limited to, point-to-point links, circuit-switching networks like Integrated Services Digital Networks (ISDN) and variations thereon, packet-switching networks, and Digital Subscriber Lines (DSL). The mobile networks may include communication links based on one or more of the following mobile communication protocols: GSM/GPRS/EDGE (2G), UMTS/HSPA (3G), long term evolution (LTE) or 4G, LTE-Advanced (LTE-A), new radio (ER) or 5G, etc.

FIG. 6C illustrates an exemplary uncontrolled patient monitoring system, for example, when the patient is away from a healthcare facility. The uncontrolled patient monitoring system may be used for pre-surgical patient monitoring when a patient is being prepared for a surgical procedure but is away from a healthcare facility, or in post-surgical monitoring, for example, when a patient is recovering away from a healthcare facility.

As illustrated in FIG. 6C, one or more sensing systems 20069 are in communication with a computing device 20200, for example, a personal computer, a laptop, a tablet, or a smart phone. The computing system 20200 may provide processing for monitoring of various biomarkers associated with a patient, a notification mechanism to indicate that a milestone (e.g., a recovery milestone) is met or a complication is detected. The computing system 20200 may also provide instructions for the user of the sensing system to follow. The communication between the sensing systems 20069 and the computing device 20200 may be established directly using a wireless protocol as described herein or via the wireless router/hub 20211.

As shown in FIG. 6C, the sensing systems 20069 may be connected to the computing device 20200 via router 20211. The router 20211 may include wireless routers, wired switches, wired routers, wired or wireless networking hubs, etc. The router 20211 may provide a direct communication connection between the sensing systems 20069 and the cloud servers 20064, for example, without involving the local computing device 20200. The computing device 20200 may be in communication with the cloud server 20064. For example, the computing device 20200 may be in communication with the cloud 20064 through a wired or a wireless communication channel. In an example, a sensing system 20069 may be in communication with the cloud directly over a cellular network, for example, Via a cellular base station 20210.

As shown in FIG. 6C, the computing device 20200 may include a processor 20203 and a network or an RF interface 20201. The processor 20203 may be coupled to a storage 20202, memory 20212, non-volatile memory 20213, and input/output interface 20204 via a system bus, as described in FIG. 6A and FIG. 6B. Details about the hardware and software components of the computer system are provided in FIG. 6A. The computing device 20200 may include a set of sensors, for example, sensor #1 20205, sensor #2 20206 up to sensor #n 20207. These sensors may be a part of the computing device 20200 and may be used to measure one or more attributes associated with the patient. The attributes may provide a context about a biomarker measurement performed by one of the sensing systems 20069. For example, sensor #1 may be an accelerometer that may be used to measure acceleration forces in order to sense movement or vibrations associated with the patient. In an example, the sensors 20205 to 20207 may include one or more of: a pressure sensor, an altimeter, a thermometer, a lidar, or the like.

As shown n FIG. 6B, a sensing system 20069 may include a processor, a radio frequency interface, a storage, a memory or non-volatile memory, and input/output interface via a system bus, as described in FIG. 6A. The sensing system may include a sensor unit and a processing and communication unit, as described in FIG. 7B through 7D. The system bus can be any of several types of bus structure(s) including the memory bus or memory controller, a peripheral bus or external bus, and/or a local bus, as described herein. The processor may be any single-core or multicore processor, as described herein.

The sensing system 20069 may be in communication with a human interface system 20215. The human interface system 20215 may be a touch screen display. The human interface system 20215 may be used to display information associated with a patient biomarker, display a prompt for a user action by a patient, or display a notification to a patient indicating information about a recovery millstone or a complication. The human interface system 20215 may be used to receive input from a patient. Other human interface systems may be connected to the sensing system 20069 via the I/O interface. For example, the human interface system may include devices for providing a haptic feedback as a mechanism for prompting a user to pay attention to a notification that may be displayed on a display unit. The sensing system 20069 may operate in a networked environment using logical connections to one or more remote computers, such as cloud computer(s), or local computers, as described in FIG. 6B.

FIG. 7A illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

In one aspect, the microcontroller 20221 may be any single-core or multicore processor such as those known under the trade name ARM Cortex by Texas instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a pre fetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 20230 may be controlled by the motor driver 20229 and can be employed by the filing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay moan, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In sortie examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transition (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QIN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a, reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

In one form, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5 and FIG. 6A.

FIG. 7B shows an example sensing system 20069. The sensing system may be a surgeon sensing system or a patient sensing system. The sensing system 20069 may include a sensor unit 20235 and a humans interface system 20242 that are in communication with a data processing and communication unit 20236. The data processing and communication unit 20236 may include an analog-to-digital converted 20237, a data processing unit 20238, a storage unit 20239, and an input/output interface 20241, a transceiver 20240. The sensing system 20069 may be in communication with a surgical hub or a computing device 20243, which in turn is in communication with a cloud computing system 20244. The cloud computing system 20244 may include a cloud storage system 20078 and one or more cloud servers 20077.

The sensor unit 20235 may include one or more ex vivo or in vivo sensors for measuring one or more biomarkers. The biomarkers may include, for example, Blood pH, hydration state, oxygen saturation, core body temperature, heart rate, Heart rate variability, Sweat rate, Skin conductance, Blood pressure, Light exposure, Environmental temperature, Respiratory rate, Coughing and sneezing, Gastrointestinal motility, Gastrointestinal tract imaging, Tissue perfusion pressure, Bacteria in respiratory tract, Alcohol consumption, Lactate (sweat), Peripheral temperature, Positivity and optimism, Adrenaline (sweat), Cortisol (sweat), Edema, Mycotoxins, VO2 max, Pre-operative pain, chemicals in the air, Circulating tumor cells, Stress and anxiety, Confusion and delirium, Physical activity, Autonomic tone, Circadian rhythm, Menstrual cycle, Sleep, etc. These biomarkers may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the biomarkers as described herein using one of more of the following sensing technologies: photoplethysmography, electrocardiography, electroencephalography, colorimetry, impedimentry, potentiometry, amperometry, etc.

As illustrated in FIG. 7B, a sensor in the sensor unit 20235 may measure a physiological signal (e.g., a voltage, a current, a PPG signal, etc.) associated with a biomarker to be measured. The physiological signal to be measured may depend on the sensing technology used, as described herein. The sensor unit 20235 of the sensing system 20069 may be in communication with the data processing and communication unit 20236. In an example, the sensor unit 20235 may communicate with the data processing and communication unit 20236 using a wireless interface. The data processing and communication unit 20236 may include an analog-to-digital converter (ADC) 20237, a data processing unit 20238, a storage 20239, an I/O interface 20241, and an RE transceiver 20240. The data processing unit 20238 may include a processor and a memory unit.

The sensor unit 20235 may transmit the measured physiological signal to the ADC 20237 of the data processing and communication unit 20236. In an example, the measured physiological signal may be passed through one or more filters (e.g., an RC, low-pass filter before being sent to the ADC. The ADC may convert the measured physiological signal into measurement data associated with the biomarker. The ADC may pass measurement data to the data processing unit 20238 for processing, in an example, the data processing unit 20238 may send the measurement data associated with the biomarker to a surgical hub or a computing device 20243, which in turn may send the measurement data to a cloud computing system 20244 for further processing. The data processing unit may send the measurement data to the surgical hub or the computing device 20243 using one of the wireless protocols, as described herein. In an example, the data processing unit 20238 may first process the raw measurement data received from the sensor unit and send the processed measurement data to the surgical hub or a computing device 20243.

In an example, the data processing and communication unit 20236 of the sensing system 20069 may receive a threshold value associated with a biomarker for monitoring from a surgical hub, a computing device 20243, or directly from a cloud server 20077 of the cloud computing system 20244. The data processing unit 20236 may compare the measurement data associated with the biomarker to be monitored with the corresponding threshold value received from the surgical hub, the computing device 20243, or the cloud server 20077. The data processing and communication unit 20236 may send a notification message to the HID 20242 indicating that a measurement data value has crossed the threshold value. The notification message may include the measurement data associated with the monitored biomarker. The data processing and computing unit 20236 may send a notification via a transmission to a surgical hub or a computing device 20243 using one of the following RF protocols: Bluetooth, Bluetooth Low-Energy (BLE), Bluetooth Smart, Zigbee, Z-wave, IPv6 Low-power wireless Personal Area Network (6LoWPAN), The data processing unit 20238 may send a notification (e.g., a notification for an HCP) directly to a cloud server via, a transmission to a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A1, new radio (NE) or 5G. In an example, the sensing unit may be in communication with the hub/computing device via a router, as described in FIG. 6A through FIG. 6C.

FIG. 7C shows an example sensing system 20069 (e.g., a surgeon sensing system or a patient sensing system). The sensing system 20069 may include a sensor unit 20245, a data processing and communication unit 20246, and a human interface device 20242. The sensor unit 20245 may include a sensor 20247 and an analog-to-digital converted (ADC) 20248. The ADC 20248 in the sensor unit 20245 may convert a physiological signal measured by the sensor 20247 into measurement data associated with a biomarker. The sensor unit 20245 may send the measurement data to the data processing and communication unit 20246 for further processing. In an example, the sensor unit 20245 may send the measurement data to the data processing and communication unit 20246 using an inter-integrated circuit (I2C) interface.

The data processing and communication unit 20246 includes a data processing unit 20249, a storage unit 20250, and an RF transceiver 20251. The sensing system may be in communication with a surgical hub or a computing device 20243, which in turn may be in communication with a cloud computing system 20244. The cloud computing system 20244 may include a remote server 20077 and an associated remote storage 20078. The sensor unit 20245 may include one or more ex vivo or in vivo sensors for measuring one or more biomarkers, as described herein.

The data processing and communication unit 20246 after processing the measurement data received from the sensor unit 20245 may further process the measurement data and/or send the measurement data to the smart hub or the computing device 20243, as described in FIG. 7B. In an example, the data, processing and communication unit 20246 may send the measurement data received from the sensor unit 20245 to the remote server 20077 of the cloud computing system 20244 for further processing and/or monitoring.

FIG. 7D shows an example sensing system 20069 (e.g., a surgeon sensing system or a patient sensing system). The sensing system 20069 may include a sensor unit 20252, a data processing and communication unit 20253, and a human interface system 20261. The sensor unit 20252 may include a plurality of sensors 20254, 20255 up to 20256 to measure one or more physiological signals associated with a patient or surgeon's biomarkers and/or one or more physical state signals associated with physical state of a patient or a surgeon. The sensor unit 20252 may also include one or more analog-to-digital converter(s) (ADCs) 20257. A list of biomarkers may include biomarkers such as those biomarkers disclosed herein. The ADC(s) 20257 in the sensor unit 20252 may convert each of the physiological signals and/or physical state signals measured by the sensors 20254-20256 into respective measurement data. The sensor unit 20252 may send the measurement data associated with one or more biomarkers as well as with the physical state of a patient or a surgeon to the data processing and communication unit 20253 for further processing. The sensor unit 20152 may send the measurement data to the data processing and communication unit 20253 individually for each of the sensors Sensor 1 20254 to Sensor N 20256 or combined for all the sensors. In an example, the sensor unit 20252 may send the measurement data to the data processing and communication unit 20253 via an I2C interface.

The data processing and communication unit 20253 may include a data processing unit 20258, a storage unit 20259, and an RE transceiver 20260. The sensing system 20069 may be in communication with a surgical hub or a computing device 20243, which in turn is in communication unit a cloud computing system 20244 comprising at least one remote server 20077 and at least one storage unit 20078. The sensor units 20252 may include one or more ex vivo or in vivo sensors for measuring one or more biomarkers, as described herein.

Figure 8:
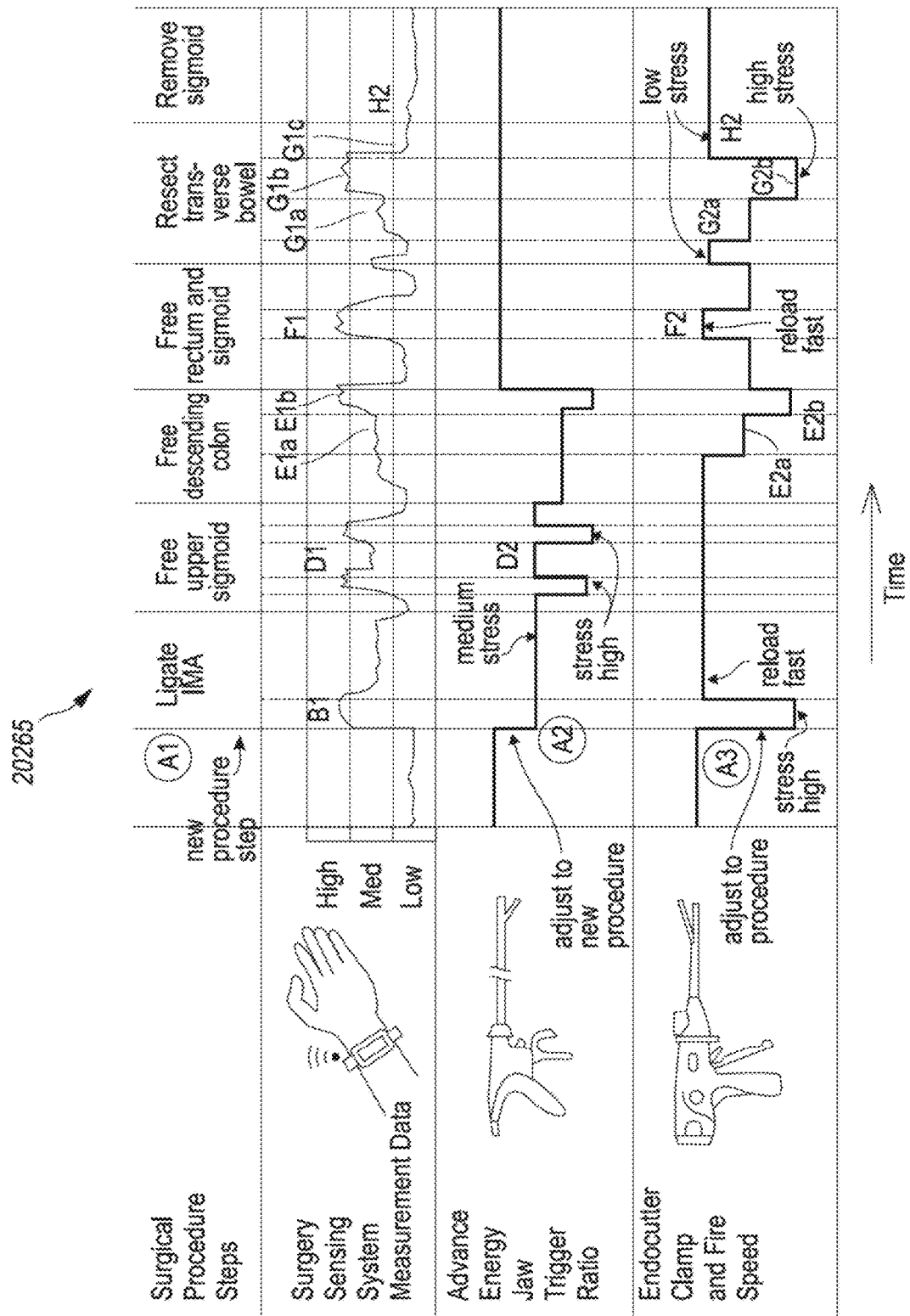
FIG. 8 illustrates an exemplary timeline of an illustrative surgical procedure indicating adjusting operational parameters of a surgical device based on a surgeon biomarker level.

FIG. 8 is an example of using a surgical task situational awareness and measurement data from one or more surgeon sensing systems to adjust surgical instrument controls. FIG. 8 illustrates a timeline 20265 of an illustrative surgical procedure and the contextual information that a surgical hub can derive from data received from one or more surgical devices, one or more surgeon sensing systems, and/or one or more environmental sensing systems at each step in the surgical procedure. The devices that could be controlled by a surgical hub may include advanced energy devices, endocutter clamps, etc. The surgeon sensing systems may include sensing systems for measuring one or more biomarkers associated with the surgeon, for example, heart rate, sweat composition, respiratory rare, etc. The environmental sensing system may include systems for measuring one or more of the environmental attributes, for example, cameras for detecting a surgeon's position/movements/breathing pattern, spatial microphones, for example to measure ambient noise in the surgical theater and/or the tone of voice of a healthcare provider, temperature/humidity of the surroundings, etc.

In the following description of the timeline 20265 illustrated in FIG. 8, reference should also be made to FIG. 5. FIG. 5 provides various components used in a surgical procedure. The timeline 20265 depicts the steps that may be taken individually and/or collectively by the nurses, surgeons, and other medical personnel during the course of an exemplary colorectal surgical procedure. In a colorectal surgical procedure, a situationally aware surgical hub 20076 may receive data from various data sources throughout the course of the surgical procedure, including data generated each time a healthcare provider (HCP) utilizes a modular device/instrument 20095 that is paired with the surgical hub 20076. The surgical hub 20076 may receive this data from the paired modular devices 20095. The surgical hub may receive measurement data from sensing systems 20069. The surgical hub may use the data from the modular device/instruments 20095 and/or measurement data from the sensing systems continually derive inferences (i.e., contextual information) about an HCPs stress level and the ongoing procedure as new data is received, such that the stress level of the surgeon relative to the step of the procedure that is being performed is obtained. The situational awareness system of the surgical hub 20076 may perform one or more of the following: record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the FOV of the medical imaging device, change the energy level of an ultrasonic surgical instrument or RF electrosurgical instrument), or take any other such action described herein. In an example, these steps may be performed by a remote server 20077 of a cloud system 20064 and communicated with the surgical hub 20076.

As a first step (not shown in FIG. 8 for brevity), the hospital staff members may retrieve the patient's EMR from the hospital's EMR database. Based on select patient data in the EMR, the surgical hub 20076 may determine that the procedure to be performed is a colorectal procedure. The staff members may scan the incoming medical supplies for the procedure. The surgical hub 20076 may cross-reference the scanned supplies with a list of supplies that can be utilized in various types of procedures and confirms that the mix of supplies corresponds to a colorectal procedure. The surgical hub 20076 may pair each of the sensing systems 20069 word by different HCPs.

Once each of the devices is ready and pre-surgical preparation is complete, the surgical tears may begin by making incisions and place trocars. The surgical team may perform access and prep by dissecting adhesions, if any, and identifying inferior mesenteric artery (IMA) branches. The surgical hub 20076 can infer that the surgeon is in the process of dissecting adhesions, at least based on the data it may receive from the RF or ultrasonic generator indicating that an energy instrument is being fired. The surgical hub 20076 may cross-reference the received data with the retrieved steps of the surgical procedure to determine that an energy instrument being fired at this point in the process (e.g., after the completion of the previously discussed steps of the procedure) corresponds to the dissection step.

After dissection, the HCP may proceed to the ligation step (e.g., indicated by A1) of the procedure. As illustrated in FIG. 8, the HCP may begin by ligating the IMA. The surgical hub 20076 may infer that the surgeon is ligating arteries and veins because it may receive data from the advanced energy jaw device and/or the endocutter indicating that the instrument is being fired. The surgical hub may also receive measurement data from one of the HCP's sensing systems indicating higher stress level of the HCP (e.g., indicated by B1 mark on the time axis). For example, higher stress level may be indicated by change in the HCP's heart rate from a base value. The surgical hub 20076, like the prior step, may derive this inference by cross-referencing the receipt of data from the surgical stapling and cutting instrument with the retrieved steps in the process (e.g., as indicated by A2 and A3). The surgical hub 20076 may monitor the advance energy jaw trigger ratio and/or the endocutter clamp and firing speed during the high stress time periods. In an example, the surgical hub 20076 may send an assistance control signal to the advanced energy jaw device and/or the endocutter device to control the device in operation. The surgical hub may send the assistance signal based on the stress level of the HCP that is operating the surgical device and/or situational awareness known to the surgical hub. For example, the surgical hub 20076 may send control assistance signals to an advanced energy device or an endocutter clamp, as indicated in FIG. 8 by A2 and A3.

The HCP may proceed to the next step of freeing the upper sigmoid followed by freeing descending colon, rectum, and sigmoid. The surgical hub 20076 may continue to monitor the high stress markers of the HCP (e.g., as indicated by D1, E1a, E1b, F1). The surgical hub 20076 may send assistance signals to the advanced energy jaw device and/or the endocutter device during the high stress time periods, as illustrated in FIG. 8.

After mobilizing the colon, the HCP may proceed with the segmentectomy portion of the procedure. For example, the surgical hub 20076 may infer that the PICT is transecting the bowel and sigmoid removal based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. It should be noted that surgeons regularly switch back and forth between surgical stapling/cutting instruments and surgical energy (e.g., RF or ultrasonic) instruments depending upon the step in the procedure because different instruments are better adapted for particular tasks. Therefore, the sequence in which the stapling/cutting instruments and surgical energy instruments are used can indicate what step of the procedure the surgeon is performing.

The surgical hub may determine and send a control signal to surgical device based on the stress level of the HCP. For example, dining time period G1b, a control signal G2b may be sent to an endocutter clamp. Upon removal of the sigmoid, the incisions are closed, and the post-operative portion of the procedure may begin. The patient's anesthesia can be reversed. The surgical hub 20076 may infer that the patient is emerging from the anesthesia based on one or more sensing systems attached to the patient.

Figure 9:
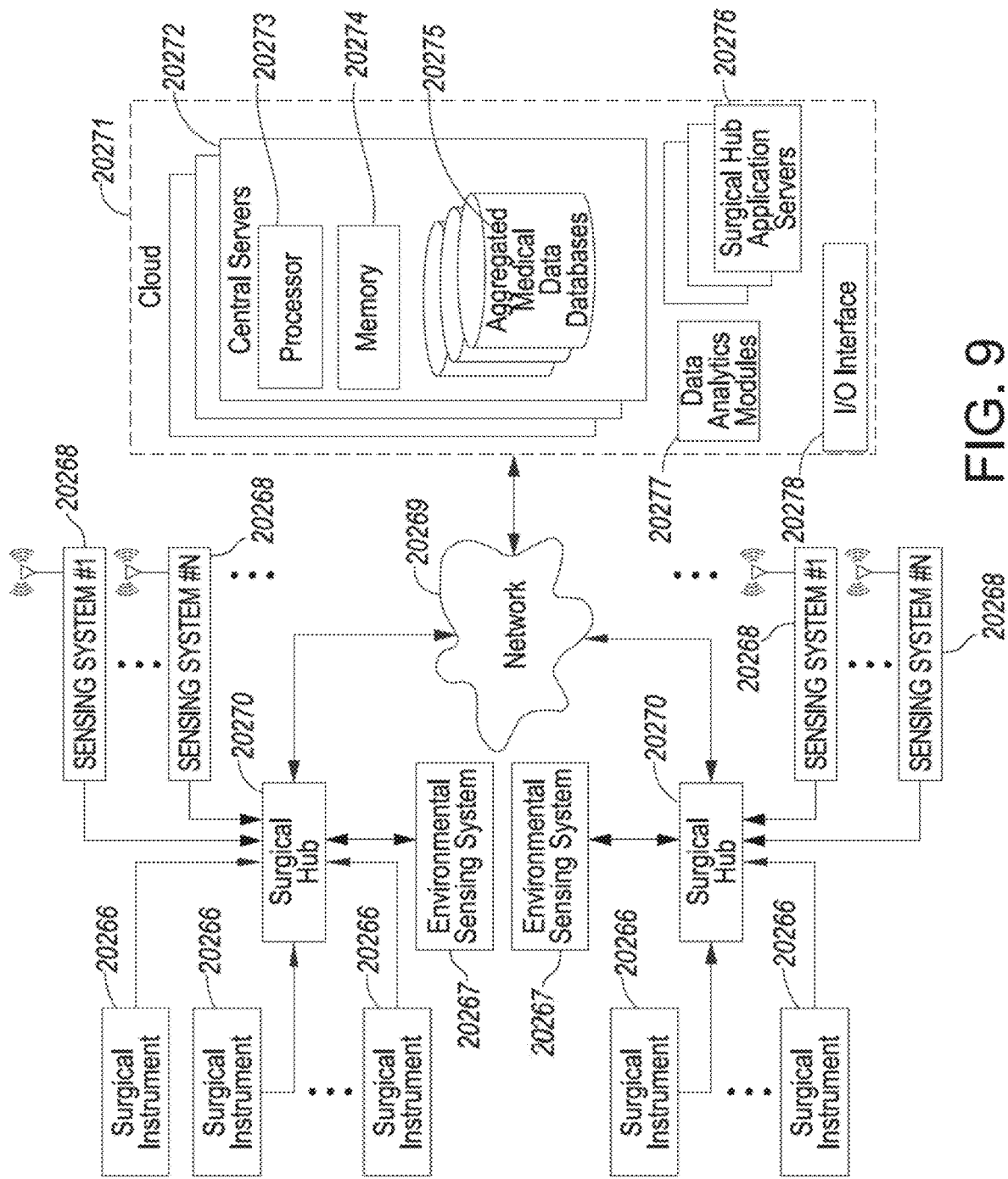
FIG. 9 is a block diagram of the computer-implemented interactive surgeon/patient monitoring system.

FIG. 9 is a block diagram of the computer-implemented interactive surgical system with surgeon/patient monitoring, in accordance with at least one aspect of the present disclosure in one aspect, the computer-implemented interactive surgical system may be configured to monitor surgeon biomarkers and/or patient biomarkers using one or more sensing systems 20069. The surgeon biomarkers and/or the patient biomarkers may be measured before, after, and/or during a surgical procedure. In one aspect, the computer-implemented interactive surgical system may be configured to monitor and analyze data related to the operation of various surgical systems 20069 that include surgical hubs, surgical instruments, robotic devices and operating theaters or healthcare facilities. The computer-implemented interactive surgical system may include a cloud-based analytics system. The cloud-based analytics system may include one or more analytics servers.

As illustrated in FIG. 9, the cloud-based monitoring and analytics system may comprise a plurality of sensing systems 20268 (may be the same or similar to the sensing systems 20069), surgical instruments 20266 (may be the same or similar to instruments 20031), a plurality of surgical hubs 20270 (may be the same or similar to hubs 20006), and a surgical data network 20269 (may be the same or similar to the surgical data network described in FIG. 4) to couple the surgical hubs 20270 to the cloud 20271 (may be the same or similar to cloud computing system 20064). Each of the plurality of surgical hubs 20270 may be communicatively coupled to one or more surgical instruments 20266. Each of the plurality of surgical hubs 20270 may also be communicatively coupled to the one or more sensing systems 20268, and the cloud 20271 of the computer-implemented interactive surgical system via the network 20269. The surgical hubs 20270 and the sensing systems 20268 may be communicatively coupled using wireless protocols as described herein. The cloud system 20271 may be a remote centralized source of hardware and software for storing, processing, manipulating, and communicating measurement data from the sensing systems 20268 and data generated based on the operation of various surgical systems 20268.

As shown in FIG. 9, access to the cloud system 20271 may be achieved via the network 20269, which may be the Internet or some other suitable computer network. Surgical hubs 20270 that may be coupled to the cloud system 20271 can be considered the client side of the cloud computing system (e.g., cloud-based analytics system). Surgical instruments 20266 may be paired with the surgical hubs 20270 for control and implementation of various surgical procedures and/or operations, as described herein. Sensing systems 20268 may be paired with surgical hubs 20270 for in-surgical surgeon monitoring of surgeon related biomarkers, pre-surgical patient monitoring, in-surgical patient monitoring, or post-surgical monitoring of patient biomarkers to track and/or measure various milestones and/or detect various complications. Environmental sensing systems 20267 may be paired with surgical hubs 20270 measuring environmental attributes associated with a surgeon or a patient for surgeon monitoring, pre-surgical patient monitoring, in-surgical patient monitoring, or post-surgical monitoring of patient.

Surgical instruments 20266, environmental sensing systems 20267, and sensing systems 20268 may comprise wired or wireless transceivers for data transmission to and from their corresponding surgical hubs 20270 (which may also comprise transceivers). Combinations of one or more of surgical instruments 20266, sensing systems 20268, or surgical hubs 20270 may indicate particular locations, such as operating theaters, intensive care unit (ICU) rooms, or recovery rooms in healthcare facilities (e.g., hospitals), for providing medical operations, pre-surgical preparation, and/or post-surgical recovery. For example, the memory of a surgical hub 20270 may store location data.

As shown in FIG. 9, the cloud system 20271 may include one or more central servers 20272 (may be same or similar to remote server 20067), surgical hub application servers 20276, data analytics modules 20277, and an input/output ("I/O") interface 20278. The central servers 20272 of the cloud system 20271 may collectively administer the cloud computing system, which includes monitoring requests by client surgical hubs 20270 and managing the processing capacity of the cloud system 20271 for executing the requests. Each of the central servers 20272 may comprise one or more processors 20273 coupled to suitable memory devices 20274 which can include volatile memory such as random-access memory (RAM) and non-volatile memory such as magnetic storage devices. The memory devices 20274 may comprise machine executable instructions that when executed cause the processors 20273 to execute the data analytics modules 20277 for the cloud-based data analysis, real-time monitoring of measurement data received from the sensing systems 20268, operations, recommendations, and other operations as described herein. The processors 20273 can execute the data analytics modules 20277 independently or in conjunction with hub applications independently executed by the hubs 20270. The central servers 20272 also may comprise aggregated medical data databases 20275, which can reside in the memory 20274.

Based on connections to various surgical hubs 20270 via the network 20269, the cloud 20271 can aggregate data from specific data generated by various surgical instruments 20266 and/or monitor real-time data from sensing systems 20268 and the surgical hubs 20270 associated with the surgical instruments 20266 and/or the sensing systems 20268. Such aggregated data from the surgical instruments 20266 and/or measurement data from the sensing systems 20268 may be stored within the aggregated medical databases 20275 of the cloud 20271. In particular, the cloud 20271 may advantageously track real-time measurement data from the sensing systems 20268 and/or perform data analysis and operations on the measurement data and/or the aggregated data to yield insights and/or perform functions that individual hubs 20270 could not achieve on their own. To this end, as shown in FIG. 9, the cloud 20271 and the surgical hubs 20270 are communicatively coupled to transmit and receive information. The I/O interface 20278 is connected to the plurality of surgical hubs 20270 via the network 20269. In this way, the I/O interface 20278 can be configured to transfer information between the surgical hubs 20270 and the aggregated medical data databases 20275.

Accordingly, interface 20278 may facilitate read/write operations of the cloud-based analytics system. Such read/write operations may be executed in response to requests from hubs 20270. These requests could be transmitted to the surgical hubs 20270 through the hub applications. The I/O interface 20278 may include one or more high speed data ports, which may include universal serial bus (USB) ports, IEEE 1394 ports, as well as Wi-Fi and Bluetooth I/O interfaces for connecting the cloud 20271 to surgical hubs 20270. The hub application servers 20276 of the cloud 20271 may be configured to host and supply shared capabilities to software applications (e.g., hub applications) executed by surgical hubs 20270. For example, the hub application servers 20276 may manage requests made by the hub applications through the hubs 20270, control access to the aggregated medical data databases 20275, and perform load balancing.

The cloud computing system configuration described in the present disclosure may be designed to address various issues arising in the context of medical operations (e.g., pre-surgical monitoring, in-surgical monitoring, and post surgical monitoring) and procedures performed using medical devices, such as the surgical instruments 20266, 20031. In particular, the surgical instruments 20266 may be digital surgical devices configured to interact with the cloud 20271 for implementing techniques to improve the performance of surgical operations. The sensing systems 20268 may be systems with one or more, sensors that are configured to measure one or more biomarkers associated with a surgeon perfuming a medical operation and/or a patient on whom a medical operation is planned to be performed, is being performed or has been performed. Various surgical instruments 20266, sensing systems 20268, and/or surgical hubs 20270 may include human interface systems (e.g., having a touch-controlled user interfaces) such that clinicians and/or patients may control aspects of interaction between the surgical instruments 20266 or the sensing system 20268 and the cloud 20271. Other suitable user interfaces for control such as auditory controlled user interfaces may also be used.

The cloud computing system configuration described in the present disclosure may be designed to address various issues arising in the context of monitoring one or more biomarkers associated with a healthcare professional (HCP) or a patient in pre-surgical, in-surgical, and post-surgical procedures using sensing systems 20268. Sensing systems 20268 may be surgeon sensing systems or patient sensing systems configured to interact with the surgical hub 20270 and/or with the cloud system 20271 for implementing techniques to monitor surgeon biomarkers and/or patient biomarkers. Various sensing systems 20268 and/or surgical hubs 20270 may comprise touch-controlled human interface systems such that the HCPs or the patients may control aspects of interaction between the sensing systems 20268 and the surgical hub 20270 and/or the cloud systems 20271. Other suitable user interfaces for control such as auditory controlled user interfaces may also be used.

Figure 10:
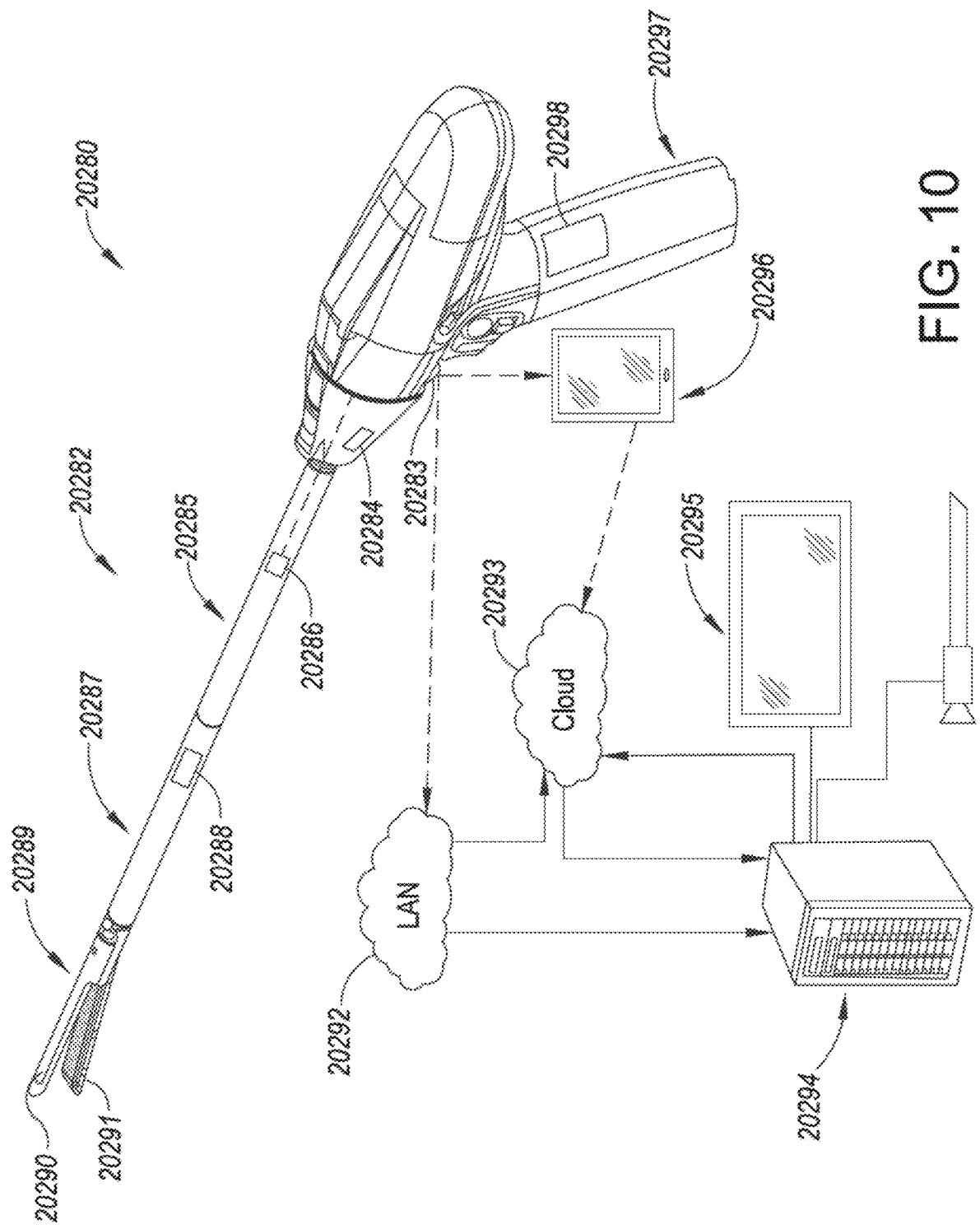
FIG. 10 show n s a example surgical system that includes a handle having a controller and a motor, an adapter releasably coupled to the handle, and a loading unit releasably coupled to the adapter.

FIG. 10 illustrates an example surgical system 20280 in accordance, with the present disclosure and may include a surgical instrument 20282 that can be in communication with a console 20294 or a portable device 20296 through a local area network 20292 or a cloud network 20293 via a wired or wireless connection. In various aspects, the console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive, shafts, the strain of the drive shafts, the temperature within the adapter 20285, a number of firings of the adapter 20285, a peak force of the adapter 20285 during firing, a total amount of force applied to the adapter 20285, a peak retraction force of, the adapter 20285, a number of pauses of the adapter 20285 during firing, etc.).

The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during filing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub 20270, as illustrated in FIG. 9. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 11B:
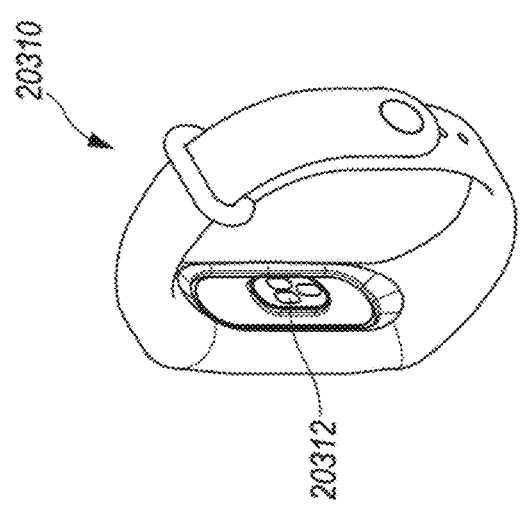
FIGS. 11A-11D illustrate examples of sensing systems that may be used for monitoring surgeon biomarkers or patient biomarkers.
Figure 11D:
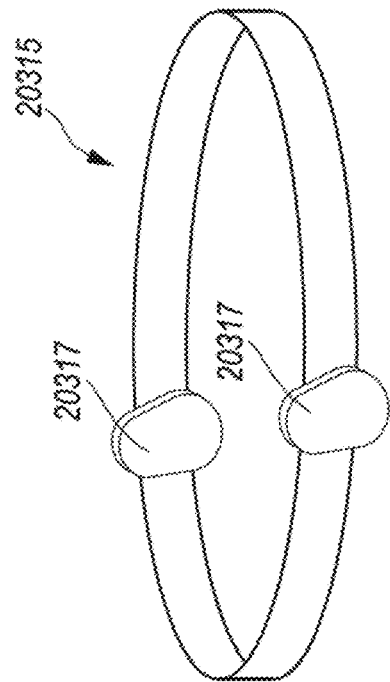
Figure 11A:
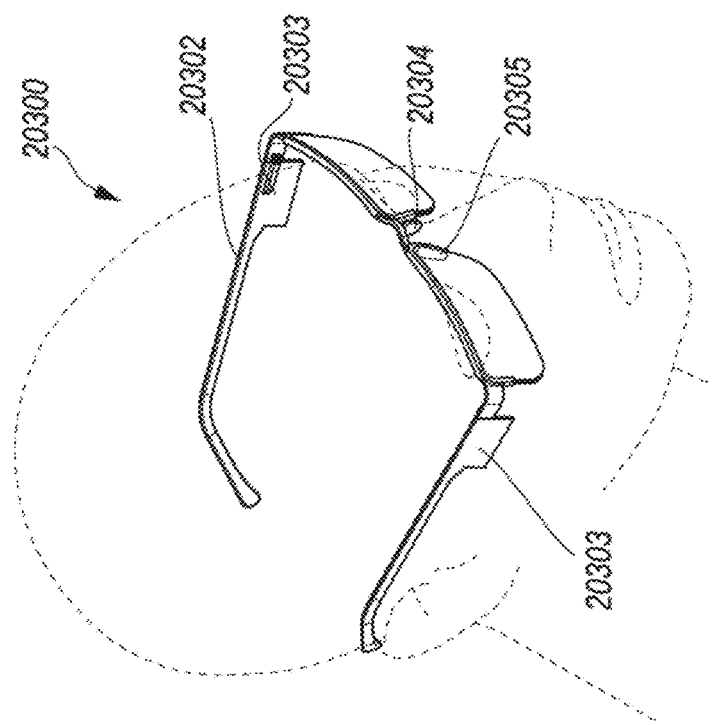

FIG. 11A to FIG. 11D illustrates examples of wearable sensing systems, e.g., surgeon sensing systems or patient sensing systems. FIG. 11A is an example of eyeglasses-based sensing system 20300 that may be based on an electrochemical sensing platform. The sensing system 20300 may be capable of monitoring (e.g., real-time monitoring) of sweat electrolytes and/or metabolites using multiple sensors 20304 and 20305 that are in contact with the surgeon's or patient's skin. For example, the sensing system 20300 may use an amperometry based biosensor 20304 and/or a potentiometry based biosensor 20305 integrated with the nose bridge pads of the eyeglasses 20302 to measure current and/or the voltage.

The amperometric biosensor 20304 may be used to measure sweat lactate levels (e.g., in mmol/L). Lactate that is a product of lactic acidosis that may occur due to decreased tissue oxygenation, which may be caused by sepsis or hemorrhage. A patient's lactate levels (e.g., >2 mmol/L) may be used to monitor the onset of sepsis, for example, during post-surgical monitoring. The potentiometric biosensor 20305 may be used to measure potassium levels in the patient's sweat. A voltage follower circuit with an operational amplifier may be used for measuring the potential signal between the reference and the working electrodes. The output of the voltage follower circuit may be filtered and converted into a digital value using an ADC.

The amperometric sensor 20304 and the potentiometric sensor 20305 may be connected to circuitries 20303 placed on each of the arms of the eyeglasses. The electrochemical sensors may be used for simultaneous real-time monitoring of sweat lactate and potassium levels. The electrochemical sensors may be screen printed on stickers and placed on each side of the glasses nose pads to monitor sweat metabolites and electrolytes. The electronic circuitries 20303 placed on the arms of the glasses frame may include a wireless data transceiver (e.g., a low energy Bluetooth transceiver) that may be used to transmit the lactate and/or potassium measurement data to a surgical hub or an intermediary device that may then forward the measurement data to the surgical hub. The eyeglasses-based sensing system 20300 may use signal conditioning unit to filter and amplify the electrical signal generated from the electrochemical sensors 20305 or 20304, a microcontroller to digitize the analog signal, and a wireless (e.g., a low energy Bluetooth) module to transfer the data to a surgical hub or a computing device, for example, as described in FIGS. 7B through 7D.

FIG. 11B is an example of a wristband-type sensing system 20310 comprising a sensor assembly 20312 (e.g., Photoplethysmography (PPG)-based sensor assembly or Electrocardiogram (ECG) based-sensor assembly). For example, in the sensing system 20310, the sensor assembly 20312 may collect and analyze arterial pulse in the wrist. The sensor assembly 20312 may be used to measure one or more biomarkers (e.g., heart rate, heart rate variability (HRV), etc.). In case of a sensing system with a PPG-based sensor assembly 20312, light (e.g., green light) may be passed through the skirt. A percentage of the green light may be absorbed by the blood vessels and some of the green light may be reflected and detected by a photodetector. These differences or reflections are associated with the variations in the blood perfusion of the tissue and the variations may be used in detecting the heart related information of the cardiovascular system (e.g., heart rate). For example, the amount of absorption may vary depending on the blood volume. The sensing system 20310 may determine the heart rate by measuring light reflectance as a function of time. HRV may be determined as the time period variation (e.g., standard deviation) between the steepest signal gradient prior to a peak, known as inter-beat intervals (IBIs).

In the case of a sensing system with an ECG-based sensor assembly 20312, a set of electrodes may be placed in contact with skin. The sensing system 20310 may measure voltages across the set of electrodes placed on the skin to determine heart rate. HRV in this case may be measured as the time period variation (e.g., standard deviation) between R peaks in the QRS complex, known as R-R intervals.

The sensing system 20310 may use a signal conditioning unit to filter and amplify the analog PPG signal, a microcontroller to digitize the analog PPG signal, and a wireless (e.g., a Bluetooth) module to transfer the data to a surgical hub or a computing device, for example, as described in FIGS. 7B through 7D.

Figure 11C:
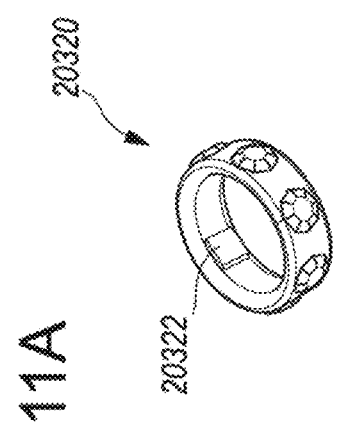

FIG. 11C is an example ring sensing system 20320. The ring sensing system 20320 may include a sensor assembly (e.g., a heart rate sensor assembly) 20322. The sensor assembly 20322 may include a light source (e.g., red or green light emitting diodes (LEDs)), and photodiodes to detect reflected and/or absorbed light. The LEDs in the sensor assembly 20322 may shine light through a finger and the photodiode in the sensor assembly 20322 may measure heart rate and/or oxygen level in the blood by detecting blood volume change. The ring sensing system 20320 may include other sensor assemblies to measure other biomarkers, for example, a thermistor or an infrared thermometer to measure the surface body temperature. The ring sensing system 20320 may use a signal conditioning unit to filter and amplify the analog LOG signal, a microcontroller to digitize the analog PPG signal, and a wireless (e.g., a low energy Bluetooth) module to transfer the data to a surgical hub or a computing device, for example, as described in FIGS. 7B through 7D.

FIG. 11D is an example of an electroencephalogram (EEG) sensing system 20315. As illustrated in FIG. 11D, the sensing system 20315 may include one or more. EEG sensor units 20317. The EEG sensor units 20317 may include a plurality of conductive electrodes placed in contact with the scalp. The conductive electrodes may be used to measure small electrical potentials that may arise outside of the head due to neuronal action within the brain. The EEG sensing system 20315 may measure a biomarker, for example, delirium by identifying certain brain patterns, for example, a slowing or dropout of the posterior dominant rhythm and loss of reactivity to eyes opening and closing. The ring sensing system 20315 may have a signal conditioning unit for filtering and amplifying the electrical potentials, a microcontroller to digitize the electrical signals, and a wireless (e.g., a low energy Bluetooth) module to transfer the data to a smart device, for example, as described in FIGS. 7B through 717.

Figure 12:
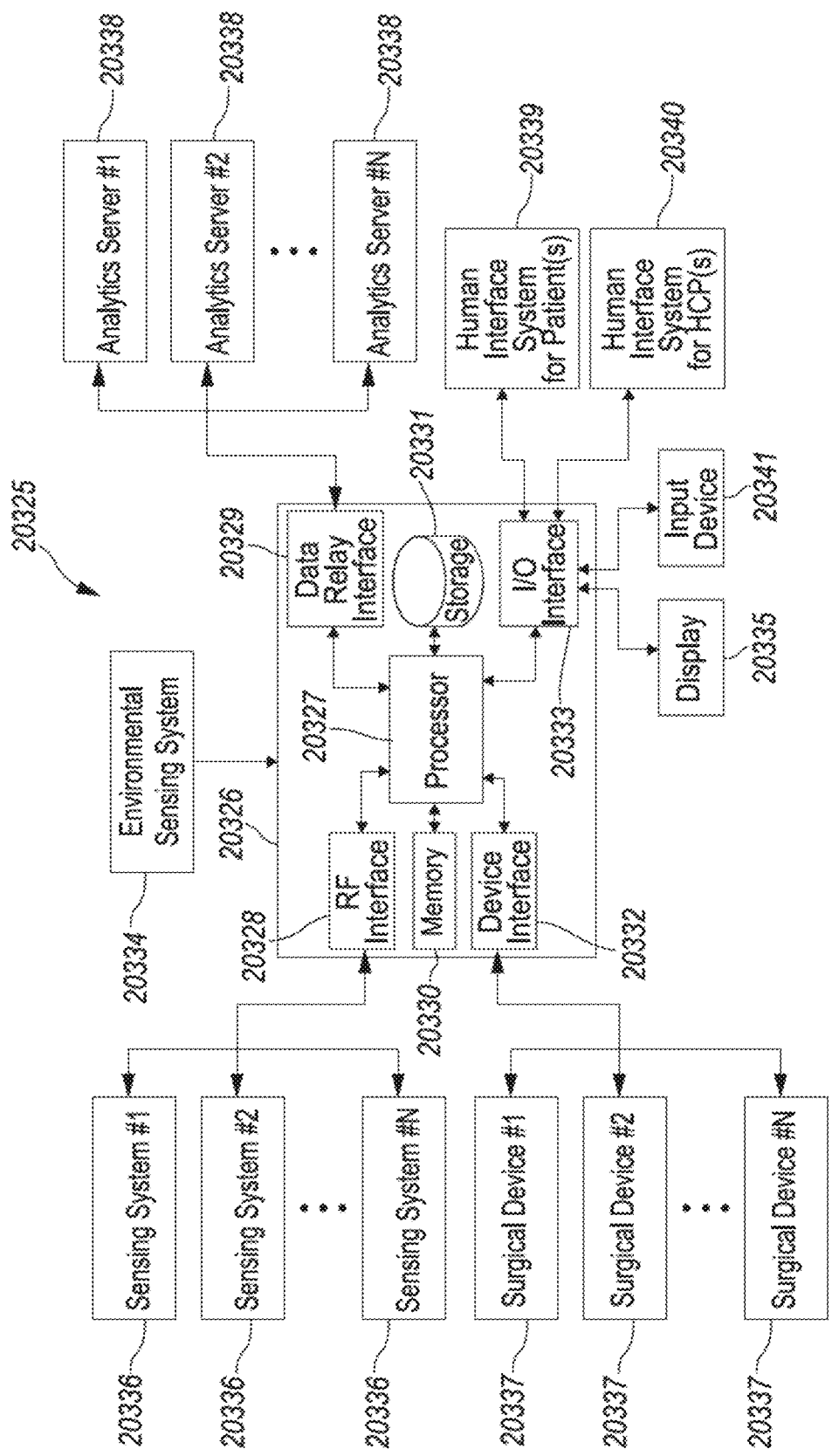
FIG. 12 is a block diagram of a patient monitoring system or a surgeon monitoring system.

FIG. 12 illustrates a block diagram of a computer-implemented patient/surgeon monitoring system 20325 for monitoring one of more patient or surgeon biomarkers prior to, during, and/or after a surgical procedure. As illustrated in FIG. 12, one or more sensing systems 20336 may be used to measure and monitor the patient biomarkers, for example, to facilitate patient preparedness before a surgical procedure, and recovery after a surgical procedure. Sensing systems 20336 may be used to measure and monitor the surgeon biomarkers in real-time, for example, to assist surgical tasks by communicating relevant biomarkers (e.g., surgeon biomarkers) to a surgical hub 20326 and/or the surgical devices 20337 to adjust their function. The surgical device functions that may be adjusted may include power levels, advancement speeds, closure speed, loads, wait times, or other tissue dependent operational parameters. The sensing systems 20336 may also measure one or more physical attributes associated with a surgeon or a patient. The patient biomarkers and/or the physical attributes may be measured in real lime.

The computer-implemented wearable patient/surgeon wearable sensing system 20325 may include a surgical hub 20326, one or more sensing systems 20336, and one or more surgical devices 20337. The sensing systems and the surgical devices may be communicably coupled to the surgical hub 20326. One or more analytics servers 20338, for example part of an analytics system, may also be communicably coupled to the surgical hub 20326. Although a single surgical hub 20326 is depicted, it should be noted that the wearable patient/surgeon wearable sensing system 20325 may include any number of surgical hubs 20326, which can be connected to form a network of surgical hubs 20326 that are communicably coupled to one or more analytics servers 20338, as described herein.

In an example, the surgical hub 20326 may be a computing device. The computing device may be a personal computer, a laptop, a tablet, a smart mobile device, etc. In an example, the computing device may be a client computing device of a cloud-based computing system. The client computing device may be a thin client.

In an example, the surgical hub 20326 may include a processor 20327 coupled to a memory 20330 for executing instructions stored thereon, a storage 20331 to store one or more databases such as an EMR database, and a data relay interface 20329 through which data is transmitted to the analytics servers 20338. In an example, the surgical hub 20326 further may include an I/O interface 20333 having an input device 20341 (e.g., a capacitive touchscreen or a keyboard) for receiving inputs from a user and an output device 20335 (e.g., a display screen) for providing outputs to a user. In an example, the input device and the output device may be a single device. Outputs may include data from a query input by the user, suggestions for products or a combination of products to use in a given procedure, and/or instructions for actions to be carried out before, during, and/or after a surgical procedure. The surgical hub 20326 may include a device interface 20332 for communicably coupling the surgical devices 20337 to the surgical hub 20326. In one aspect, the device interface 20332 may include a transceiver that may enable one or more surgical devices 20337 to connect with the surgical hub 20326 via a wired interface or a wireless interface using one of the wired or wireless communication protocols described herein. The surgical devices 20337 may include, for example, powered staplers, energy devices or their generators, imaging systems, or other linked systems, for example, smoke evacuators, suction-irrigation devices, insufflation systems, etc.

In an example, the surgical hub 20326 may be communicably coupled to one or more surgeon and/or patient sensing systems 20336. The sensing systems 20336 may be used to measure and/or monitor, in real-time, various biomarkers associated with a surgeon performing a surgical procedure or a patient on whom a surgical procedure is being performed. A list of the patient/surgeon biomarkers measured by the sensing systems 20336 is provided herein. In an example, the surgical hub 20326 may be communicably coupled to an environmental sensing system 20334. The environmental sensing systems 20334 may be used to measure and/or monitor, in real-time, environmental attributes, for example, temperature/humidity in the surgical theater, surgeon movements, ambient noise in the surgical theater caused by the surgeon's and/or the patient's breathing pattern, etc.

When sensing systems 20336 and the surgical devices 20337 are connected to the surgical hub 20326, the surgical hub 20326 may receive measurement data associated with one or more patient biomarkers, physical state associated with a patient, measurement data associated with surgeon biomarkers, and/or physical state associated with the surgeon from the sensing systems 20336, for example, as illustrated in FIG. 7B through 7D. The surgical hub 20326 may associate the measurement data, e.g., related to a surgeon, with other relevant pre-surgical data and/or data from situational awareness system to generate control signals for controlling the surgical devices 20337, for example, as illustrated in FIG. 8.

In an example, the surgical hub 20326 may compare the measurement data from the sensing systems 20336 with one or more thresholds defined based on baseline values, pre-surgical measurement data, and/or in surgical measurement data. The surgical hub 20326 may compare the measurement data from the sensing systems 20336 with one or more thresholds in real-time. The surgical hub 20326 may generate a notification for displaying. The surgical hub 20326 may send the notification for delivery to a human interface system for patient 20339 and/or the human interface system for a surgeon or an HCP 20340, for example, if the measurement data crosses (e.g., is greater than or lower than) the defined threshold value. The determination whether the notification would be sent to one or more of the to the human interface system for patient 20339 and/or the human interface system for an HCP 2340 may be based on a severity level associated with the notification. The surgical hub 20326 may also generate a severity level associated with the notification for displaying. The severity level generated may be displayed to the patient and/or the surgeon or the HCP. In an example, the patient biomarkers to be measured and/or monitored (e.g., measured and/or monitored in real-time) may be associated with a surgical procedural step. For example, the biomarkers to be measured and monitored for transection of veins and arteries step of a thoracic surgical procedure may include blood pressure, tissue perfusion pressure, edema, arterial stiffness, collagen content, thickness of connective tissue, etc., whereas the biomarkers to be measured and monitored for lymph node dissection step of the surgical procedure may include monitoring blood pressure of the patient. In an example, data regarding postoperative complications could be retrieved from an EMR database in the storage 20331 and data regarding staple or incision line leakages could be directly detected or inferred by a situational awareness system. The surgical procedural outcome data can be inferred by a situational awareness system from data received from a variety of data sources, including the surgical devices 20337, the sensing systems 20336, and the databases in the storage 20331 to which the surgical hub 20326 is connected.

The surgical hub 20326 may transmit the measurement data and physical state data it received from the sensing systems 20336 and/or data associated with the surgical devices 20337 to analytics servers 20338 for processing thereon. Each of the analytics servers 20338 may include a memory and a processor coupled to the memory that may execute instructions stored thereon to analyze the received data. The analytics servers 20338 may be connected in a distributed computing architecture and/or utilize a cloud computing architecture. Based on this paired data, the analytics system 20338 may determine optimal and/or preferred operating parameters for the various types of modular devices, generate adjustments to the control programs for the surgical devices 20337, and transmit (or "push") the updates or control programs to the one or more surgical devices 20337. For example, an analytics system 20338 may correlate the perioperative data it received from the surgical hub 20236 with the measurement data associated with a physiological state of a surgeon or an HCP and/or a physiological state of the patient. The analytics system 20338 may determine when the surgical devices 20337 should be controlled and send an update to the surgical hub 20326. The surgical hub 20326 may then forward the control program to the relevant surgical device 20337.

Additional detail regarding the computer-implemented wearable patient/surgeon wearable sensing system 20325, including the surgical hub 30326, one or more sensing systems 20336 and various surgical devices 20337 connectable thereto, are described in connection with FIG. 5 through FIG. 7D.

A computing system, such as a surgical computing system or a surgical hub described herein, for example with reference to FIGS. 1A, 2A, B, 3, 4, 5, 6A-B, 7B-D, 9, and 12, may scan for a sensing system in an operating room, such as the sensing systems described herein with reference to FIGS. 2A-C, 3, 4, 5, 6A-C, 7B-D, 9, 11A-D, and 12. The computing system may establish a connection with the sensing system in the operating room. The computing system may receive data about one or more users in the operating room. The received data may be or may include user role identification data and/or data to identify a user role associated with a user in the operating room. Based on the received data, the computing system may identify the one or more users in the operating room. For example, the computing system may identify the users based on one or more of: proximities of the users to a surgical instrument, location tracking information of the users in the operating room, interactions between the users, one or more procedural activities, or visual data of the users in the operating room. A user in the operating room may be identified as a patient, a surgeon, a nurse, a staff, and/or a healthcare professional (HCP). The computing system may identify a user role associated with a user (e.g., each user) in the operating room. For example, the computing system may differentiate the users based on the received data. If the computing system identifies a user role of a user in the operating room, the computing system may generate surgical aid information. The generated surgical aid information may be relevant to (e.g., specific to) the identified user and/or the identified user role.

In examples, the computing system may receive measurement data from a sensing system. The computing device may receive the measurement data from the sensing system using the established link. The computing system may determine an elevated stress level associated with the identified user. The computing system may obtain surgical contextual data. For example, the computing system may obtain surgical contextual data from a surgical instrument (e.g., usage data) and/or a sensing system associated with the user. The computing system may identify a surgical instrument that a user may be using. The computing system may determine whether the identified user is operating a surgical instrument. For example, the computing system may determine whether the identified user is operating and/or using the surgical instrument. Based on a determination that the identified user is not operating the surgical instrument and based on the measurement data that the identified user has an elevated stress level, the computing system may send surgical aid information to the identified user. The surgical aid information may be or may include an operating manual of the surgical instrument and/or an in on how to use the surgical instrument. Determination of a stress level is further described in Ser. No. 17/156,296 titled ADAPTABLE SURGICAL INSTRUMENT CONTROL, filed contemporaneously, which is incorporated by reference herein in its entirety.

For example, the computing system may receive measurement data from one of the sensing systems associated with the users in the operating room (e.g., sensing system associated with a surgeon). The computing system may also receive measurement data from one of the sensing systems associated with the users in the operating room indicating higher stress level of the users. For example, higher stress level may be indicated by change in the users' heart rate from a base value. The computing system may derive this inference by cross-referencing the receipt of data from the corresponding sensing systems. The computing system may send surgical aid information to the identified user as described herein.

In examples, the computing system may receive measurement data from a sensing system. The computing system may receive the measurement data from the sensing system using the established link. The computing system may determine an elevated fatigue level associated with the identified user. The computing system may obtain surgical contextual data. For example, the computing system may obtain surgical contextual data from a surgical instrument (e.g., usage data) and/or a sensing system associated with a user. The computing system may identify a surgical instrument that a user may be using. The computing system may determine whether the identified user is operating a surgical instrument. As described herein, the computing system may determine whether the identified user is operating the surgical instrument based on contextual data. Based on the contextual data, the computing system may determine whether the identified user is using the surgical instrument or not. Based on a determination that the identified user is operating the surgical instrument and based on the measurement data that the identified user has the elevated fatigue level, the computing system may send surgical aid information to the identified user. The surgical aid information may be or may include an indication of fatigue control for the surgical instrument. Determination of a fatigue level is further described in Ser. No. 17/156,296 titled ADAPTABLE SURGICAL INSTRUMENT CONTROL, filed contemporaneously, which is incorporated by reference herein in its entirety.

For example, the computing system may receive measurement data from one of the sensing systems associated with twee users in twee operating room (e.g., sensing system associated with a surgeon). The measurement data may indicate the users, such as a surgeon, make too large of a change in input, which may be referred to as over-correction, for a perceived mistake. The computing system may interpret repeated correction, over-correction, or oscillating reaction as an indicator of fatigue and/or elevated fatigue level associated with the identified user.

The computing system may be configured to analyze usage data and/or measurement data to determine whether a user working in the operating room is experiencing fatigue and, if so, to modify operation of the surgical instrument and/or to provide notifications associated with the fatigue levels. For example, the computing system may monitor user inputs to a surgical instrument (e.g., from the surgical instrument and/or from sensing systems). The user inputs to the surgical instrument may include inputs that result in shaking of the surgical instrument. Shaking, whether done intentionally or otherwise, may be detected by one or more sensing systems (e.g., acceleration sensors) which provide data regarding the movement and orientation of the surgical instrument. The detected data may indicate magnitude and frequency of any tremors. The surgical instrument may generate usage data associated with the monitored user inputs. The usage data may indicate the inputs to the surgical instrument, e.g., including movements of all or a portion of the surgical instrument including shaking. The usage data may be communicated to the computing system.

Data may be collected from sensing systems that may be applied to the users of the surgical instrument as well as other healthcare professionals who may assist in the operating room. Accelerometers may be applied to the users hands, wrists, and/or arms. Accelerometers may also be applied to users' torsos to gather data associated with the body movements including swaying and body tremors. The accelerometers may generate data regarding motion and orientation of the users' hands and/or arms. The data may indicate magnitude and frequency of movements including shaking. Sensing systems (e.g., that may be or may include accelerometers) may collect biomarker data from the users including data associated with heartbeat, respiration, temperature, etc. The sensing systems may collect data associated with the hydration/dehydration of the corresponding users operating the surgical instrument as well as the other users assisting in the operating room. The gathered data may be communicated to the computing system.

The computing system may receive usage data from the surgical instrument and may receive sensor data from the sensing systems corresponding to the users in the operating room. The computing system may identify and/or store the received data in association with time stamp data indicating time the data was collected corresponding to the user.

The computing system may determine, based on the received usage data and/or sensor data, fatigue levels for the users operating the surgical instrument and assisting in the operating room. The computing system may determine, based on the received usage data and sensor data, time periods associated with the surgical procedure. The computing system may determine, for each users, values associated with time in the operating room, time spent standing in the operating room, nine spent physically exerting themselves. The computing system may determine fatigue levels for the users based on the time spent in surgery.

The computing system may determine, based on the received usage data and/or sensor data, physical indications of fatigue. The computing system may determine, if the received data indicates a user is swaying or unsteady, that the user is fatigued. The computing system may determine, if the received data indicates tremors are exhibited by a user, that the user is fatigued.

The computing system may determine, based on the received usage data and sensor data, values associated with hydration/dehydration of the users in the operating room. Dehydration may impact energy levels and make a person feel tired and fatigued. Less body fluid tends to increase heart rate. The computing system may analyze heartbeat data in the context of hydration levels and differentiate between stress and other heart elevation events from hydration. The computing system may employ a baseline measure to differentiate acute events from ongoing chronic events and to differentiate between fatigue and dehydration associated with each users in the operating room.

The computing system may calculate a weighted measure of fatigue for the user operating the surgical instrument as well as others in the operating room. The weighted measure of fatigue may be based on cumulative cooperative events and contributions. For example, the weighted measure of fatigue may be based on the intensity of stress experienced by a user and the force exerted by the user over time in controlling an actuator such as closure trigger over time.

If the computing system determines that the users have experienced fatigue, the computing system may determine to communicate control features to the surgical instrument to perform fatigue control or accommodation and adjust operation to compensate for fatigue. The control feature to perform fatigue control may indicate to reduce the force required to implement an action. For example, the control feature may indicate to reduce the force needed to be applied to a closure trigger to activate clamping jaws of a surgical instrument. The control feature may indicate to increase the sensitivity of the closure trigger. The control features may indicate to increase delay or wait time responsive to user inputs. The control features may indicate to slow activation and provide additional time before acting.

If the computing system determines the users have experienced fatigue, the computing system may also determine to communicate control features to provide notifications regarding the fatigue. The computing system may determine that notifications regarding fatigue may be provided by the surgical instrument to the user. The computing system may determine that the notifications may provide more steps-for-use to the operator. The computing system may also determine that notifications regarding fatigue levels may be made to persons in the operating room other than the healthcare professional manning the instrument. Such notifications may be displayed on display systems in or near the operating room.

The computing system may communicate an indication of a control features associated with fatigue control. The control features may be communicated to the surgical instrument and may also be communicated to other systems in the operating room such as display which may be employed to provide notifications.

The surgical instrument and display may receive the indication of control features indicating to implement fatigue control and provide notifications. The surgical instrument: may determine to operate consistent with the indication of fatigue control. The instrument may reduce the force required to activate and/or operate closure trigger. The surgical instrument may increase the delay or wait time between requesting an action, e.g., applying force to the closure trigger, and implementing the corresponding action, e.g., closing the jaws. The surgical instrument may slow activation in response to inputs and thereby provide more time for the operator to position the surgical instrument.

If the control features indicate to provide notifications, the surgical instrument may provide physical tactile feedback as well as visual feedback. The display may also provide visual feedback regarding fatigue. The notifications may provide steps-for-use to minimize overlooking of details.

Figure 13:
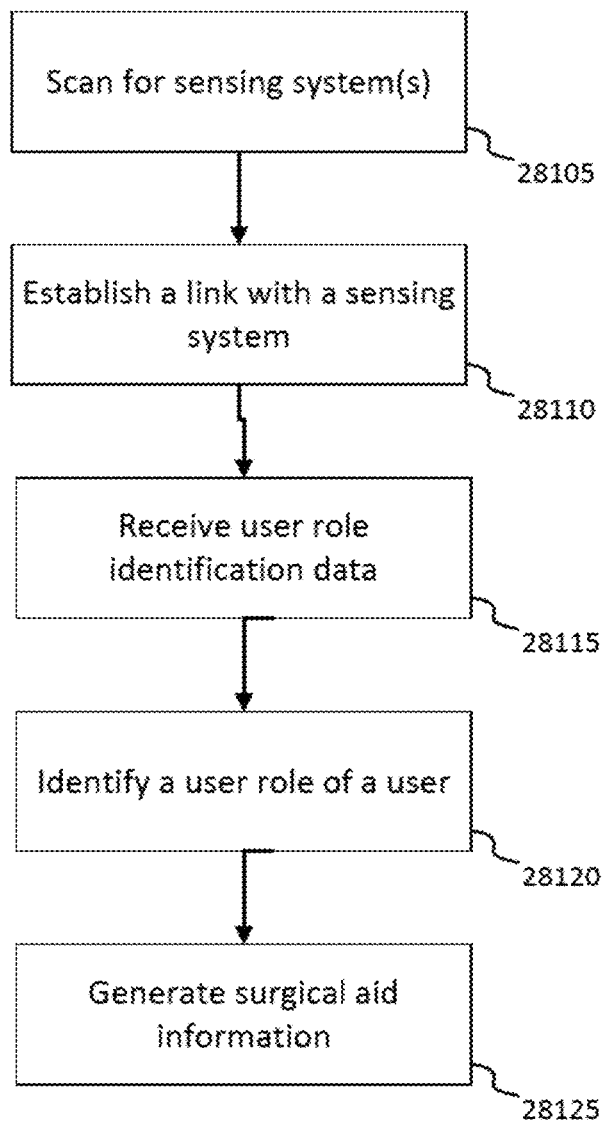
FIG. 13 illustrates an example flow for generating surgical aid information to a user in an operating room.

FIG. 13 illustrates an example flow for generating surgical aid information to a user in an operating room. At 28105, a computing system (e.g., such as a surgical computing system) may scan for a sensing system. The computing system may scan for a sensing system located in an operating room. As described herein, the sensing system may have measurement data associated with a user. For example, a user may be wearing the sensing system. The sensing system may monitor and/or sense measurement data of the user. As described herein, the sensing system may send user role identification data. The sensing system may send the user role identification data to the computing system. The user role identification data may be or may include data associated with identifying a user role of a user in an operating room.

At 28110, the computing system may establish a link with the sensing system. The computing system may communicate with the sensing system using the established link. The sensing system may send data, such as user role identification data and/or measurement data as described herein, using the established link.

At 28115, the computing system may receive user role identification data. The computing system may receive the user role identification data from the sensing system. The computing system may receive the user role identification data from the sensing system using the established link. The user role identification data may be or may include data for identifying a user role associated with a user. The user role associated with a user may be or may include a patient, a surgeon, a nurse, an HCP, a hospital staff, and/or the like. The user role identification data may be or may include a proximity of a user to one or more surgical instruments, location tracking information of the users in the operating room, interactions between the users, one or more surgical procedural activities, or visual data of the users in the operating room.

At 28120, the computing system may identify a user role of a user in the operating room based on the received user role identification data. As described herein, the computing system may identify that a user role associated with a user in the operating room is a surgeon, other user role associated with other user in the operating room is a nurse (e.g., a head nurse), another user role associated with another user in the operating room is a hospital staff and/or an HCP based on the user role identification data.

In examples, the user role identification data may be or may include data associated with proximities of a user to a surgical instrument(s). The computing system may identify a user role of a user in the operating room based on the proximities of the users to one or more surgical instruments. For example, the computing system may identify a user role of a user as a surgeon. The computing system may know that a surgeon will be in proximity to (e.g., next to) one or more surgical instruments. For example, as the surgeon will be using the one or more surgical instruments for a surgical procedure, the surgeon may be in proximity to (e.g., next to) the surgical instruments. The computing system may identify a user role of a user as a nurse (e.g., a head nurse) as the nurse will be assisting the surgeon and/or may be in proximity to (e.g., next to) the one or more surgical instruments. For example, the computing system may know that a nurse may hand the surgical instruments over to a surgeon based on a request from the surgeon, and the nurse may be in proximity to (e.g., next to) the surgical instruments. The computing system may determine a user role of a user as a hospital staff and/or an HCP. A hospital staff and/or an HCP may handle non-surgical related activities and may not be in proximity to the one or more surgical instruments. For example, the hospital staff and/or the HCP may be near an entrance of the operating room, a telephone, a clock, a music player, etc. that are not in proximity to (e.g., not next to) the one or more surgical instruments.

In examples, the user role identification data may be or may include data associated with location tracking information of the users in the operating room. For example, users in the operating room may be located and/or positioned at a particular location of the operating room. A patient may be located at a center of the operating room. The patient may be located under (e.g., directly under) a central lighting of the operating room. The patient may be stationary (e.g., not moving) throughout a surgical procedure. The computing system may identify a user in an operating room as a patient based on the user's position in the operating room (e.g., center, under a central lighting, etc.) and/or tracking information (e.g., lack of movement). A surgeon may be located in proximity to (e.g., next to) the patient. The surgeon may be located in proximity to a surgical table and/or to the patient. The surgeon may be located in pro to (e.g., next to) one or more surgical instruments. The surgeon may be stationary and/or may not be moving (e.g., not walking around the operating room). The computing system may identify a user as a surgeon based on the location of the user being in proximity to at least one of a patient, a surgical table, or one or more surgical instruments and/or tracking information (e.g., lack of or little movement). A nurse assisting the surgeon (e.g., a head nurse) may be in proximity to (e.g., next to) the surgeon. The nurse may be next to a tray table that has one or more surgical instruments. The nurse may be moving from a surgical table to the tray table. The computing system may identify a user as a nurse based on the location information and/or the tracking information. A hospital staff and/or an HCPs may be located farther away from the surgical table, the surgeon, and/or the head nurse. For example, the hospital staff and/or other HCPs may be located closer to a door of the operating room and/or a phone located in the operating room. The computing system may identify a user as a hospital staff and/or an HCPs based on the location information and/or tracking inform anon provided in the user role identification data.

In examples, the user role identification data may be or may include data associated with interactions between users in the operating room. A surgeon may communicate and/or instruct other users in the operating room. The surgeon may request a surgical instrument for a surgical procedure. The surgeon may make a request to increase, to decrease, and/or to change music playing in the operating room. A nurse assisting the surgeon may act in response to the request from the surgeon. For example, the nurse may hand a surgical instrument to the surgeon after the surgeon request the surgical instrument. The hospital staff and/or other HCPs may turn up, turn down, and/or change the music based on the request from the surgeon.

In examples, the user role identification data may be or may include data associated with one or more surgical procedural activities. A sensing system associated with a user may sense and/or monitor the user's activities. In examples, a surgeon may be wearing a sensing system on his/her wrist. The sensing system may detect, measure, and/or sense the surgeon's hand movements. The sensing system may send measurement data of the surgeon's hand movements to the computing system. Based on the measurement data of the surgeon's hand movements, the computing system may identify that the measurement data is associated with a user role for a surgeon. For example, the computing system may determine that the measurement data indicates a user role of a user using one or more surgical instruments and/or performing a surgical procedure. The computing system may identify a user role associated with the user as a surgeon. In examples, a nurse may be wearing a sensing system on his/her wrist. The sensing system may detect, measure, and/or sense the nurse's hand movements of carrying a surgical instrument and/or handing the surgical instrument. The sensing system may send measurement data of the nurses hand movements to the computing system. Based on the measurement data of the nurse's hand movements, the computing system may identify that the measurement data is associated with a user role for a nurse. For example, the computing system may determine that the measurement data involves a user handing one or more, surgical instruments to another user in the operating room. The computing system may identify a user role associated with the as a nurse assisting a surgeon. In examples, a hospital staff and/or an HCP may be wearing a sensing system on his/her wrist. The sensing system may detect, measure, and/or sense the hospital staff's and/or the HCP's hand movements. For example, the sensing system may detect the hospital staff and/or the HCP answering a phone in the operating room, adjusting volume of a music player in the operating room, and/or the like. Based on the measurement data from the sensing system, the computing system may identify that the user role of a user is a hospital staff and/or an HCP.

In examples, the user role identification data may be or may include data associated with visual data of the users in the operating room. An operating room may be equipped with a camera. The computing system may receive camera feed from the camera. Based on the camera feed, the computing system may determine/identify users in the operating room. In examples, the computing system may perform face recognitions of the users. In examples, the computing system may scan user badges and/or identification tags on the users and determine/identify the users in the operating room. The computing system may identify a user role of a user in the operating room based on the camera feed.

At 28125, the computing system may generate surgical aid information to the user based on the identified user role. In examples, if the computing system identifies a user role for a user as a surgeon, the computing system may generate surgical aid information for the surgeon. In examples, if the computing system identifies a user role for a user as a nurse, the computing system may generate surgical aid information for the nurse. In examples, if the computing system identifies a user role for a user as a hospital staff and/or an HCP, the computing system may generate surgical aid information for the hospital staff and/or the HCP. The surgical aid information may be augmented reality (AR) content. The computing system may generate AR content for identified user.

In examples, the computing system may generate AR content for a surgeon. The computing system may display the AR content to a computing system that is associated with the surgeon. The computing system associated with the user (e.g., a display AR device) may display the generated AR content from the surgical computing system. The AR content may aid the surgeon in a surgical procedure. In examples, the AR content may be or may include surgical steps that the surgeon is about to perform. In examples, the AR may include measured data of a patient. The generated AR content may be converted to audio and may be transmitted to an audio AR device that the surgeon is wearing.

In examples, the computing system may receive measurement data from the sensing system. The measurement data may be or may include stress level associated with a user. For example, the measurement data may be or may include stress level associated with a surgeon. The measurement data may be or may include an elevated stress level associated with the surgeon. As described herein, the computing system may determine an elevated stress level associated with a user (e.g., a surgeon). The computing system may obtain surgical contextual data. For example, a surgical instrument may send data associated with usage of the surgical instrument. The computing system determine whether the surgeon is operating a surgical instrument based on the surgical contextual data. The computing system may determine whether the surgeon is operating a surgical instrument based on the surgical contextual data and/or measurement data associated with the surgeon (e.g., measurement data associating with the surgeon's hand movement). If the computing system determines that the surgeon is not operating a surgical instrument and detects an elevated stress level, the computing system may generate and/or send surgical aid information to the surgeon. The surgical aid information may be or may include an operation manual of the surgical instrument. The surgical aid information may be or may include an instruction (e.g., video or audio) on how to use the surgical instrument.

In examples, the computing system may receive measurement data from the sensing system. The measurement data may be or may include stress level associated with a user. For example, the measurement data may be or may include stress level associated with a nurse. The measurement data may be or may include an elevated stress level associated with the nurse. The computing system may obtain surgical contextual data. For example, a surgical instrument may send data associated with usage of the surgical instrument. The computing system may determine whether the nurse is operating the surgical instrument. For example, the computing system may obtain the contextual data that indicates that a surgical staple gun has recently been fired and needs a reload. The computing system may determine whether the nurse is operating the surgical instrument based on the contextual data and/or measurement data associated with the nurse (e.g., measurement data associating with the nurse's hand movement). If the computing system determines that the nurse is not operating a surgical instrument and detects an elevated stress level, the computing system may generate and/or send surgical aid information to the nurse. The surgical aid information may be or may include an operation manual of the surgical instrument (e.g., reloading a staple gun). The surgical aid information may be or may include an instruction (e.g., video or audio) on how to use (e.g., reload) the surgical instrument.

In examples, the computing system may receive measurement data from the sensing system. The measurement data may be or may include fatigue level associated with a user. For example, the measurement data may be or may include fatigue level associated with a surgeon. The measurement data may be or may include an elevated fatigue level associated with the surgeon. As described herein, the computing system may determine an elevated fatigue level associated with a user (e.g., a surgeon). The computing system may obtain surgical contextual data. For example, a surgical instrument may send data associated with usage of the surgical instrument. The computing system may determine whether the surgeon is operating a surgical instrument. The computing system may determine whether the surgeon is operating a surgical instrument based on contextual data and/or measurement data associated with the surgeon (e.g., measurement data associating with the surgeon's hand movement). If the computing system determines that the surgeon is not operating a surgical instrument and detects an elevated fatigue level, the computing system may generate and/or send surgical aid information to the surgeon and/or a computing system associated with the surgeon. The surgical aid information may be or may include an indication of fatigue control for the surgical instrument.

A surgical computing system may identify (e.g., situationally identify) users in an operating room. As described herein, the surgical computing system may identify a user based on a sensing system and/or a computing system associated with a user. Based on the identification of the sensing system and/or the computing system associated with the user, the surgical computing system may determine who the person is, a user role in a surgical procedure (e.g., as a whole), and/or a user role in a current surgical procedure step.

In examples, a user may check in with a surgical computing system. The user may check in with the surgical computing system as the user is entering an operating room. The user may check in with the surgical computing system during a check in procedure.

A user may scan a sensing system and/or a computing system associated with a user as the user enters an operating room. For example, a user may scan and/or tag the sensing system and/or the computing system (e.g., an AR device) to a device, such as a scanning device, associated with the surgical computing system. The surgical computing system may receive the scanned information for the sensing system and/or the computing system associated with the user (e.g., wearing the sensing system and/or the computing system). The surgical computing system may identify and/or recognize the user based on the scanned information. The surgical computing system may determine what the user's role is with a surgical procedure.

In example, a user may be wearing a computing system and/or a sensing system on his/her wrist. As the user enters an operating room, the user may place the computing system and/or the sensing system in front of a scanning device and scan the computing system and/or the sensing system. A surgical computing system may receive the scanned information. The scanned information may be or may include employee identification associated with the user, such as a name, an occupation, a badge number, number of hours worked, and/or other personal data associated with the user. The surgical computing system may determine, based on the scanned information, a user role of the user. For example, the surgical computing system may determine that the user role of the scanned user is a surgeon, a nurse, a hospital staff, and/or an HCP for a surgical operation. If the surgical computing system need additional information, the surgical computing system may ask for additional information to the user. If the surgical computing system identifies a user in the operating room, the surgical computing system may select, identify, and/or assign a user role associated with the identified user. The selected, identified, and/or assigned user role may be associated with a task of the user for the surgical operation.

In example, a user may enter an operating room and go a designated spot (e.g., in front of a monitor, in proximity to and/or next to a surgical table, a surgical tray table, and/or a surgical instrument, etc.). A surgical computing system may detect and/or identify a computing system and/or a sensing system associated with the user based on location information and/or location tracking information of the users and/or proximities of the users to one or more surgical instruments as described herein. The surgical computing system may identify the computing system and/or the sensing system and/or identify a user role associated with the user.

In examples, a user may input (e.g., manually input) user identification information. For example, a user may enter the user identification information to a surgical computing system as the user enters an operating room, prior to a surgical procedure, and/or when prompted by the surgical computing system. The user may enter his/her name, employee ID, a badge number, and/or other user identifier information that identify the user.

In examples, a surgical computing system may have a list of users who will be in an operating room, e.g., from a pre operation plan submitted by a surgeon and/or a surgical plan submitted by an HCP related to a surgical procedure. The surgical computing system may prompt a user to select the user from the list to identify the user. The surgical computing system may identify a user role associated with the identified user for the surgical procedure.

A surgical computing system may identify a user in an operating room based on context information and may identify a user role associated with the user. For example, the context information may be or may include a procedure type, a procedure step, activities of a user, location tracking information of a user in the operating room, proximity of a user to one or more surgical instruments, etc.

In examples, a surgical computing system may identify users for a surgical procedure from an operation plan, e.g., from a pre operation plan and/or a surgical plan that a surgeon submitted prior to the surgery and/or an HCP submitted for a surgical procedure. The surgical computing system may know a type of surgical procedure for the surgical procedure. The surgical computing system may have a list of surgeons who may be able to perform the surgical procedure, e.g., based on expertise of the surgeons and/or shift schedules of the surgeons. The surgical computing system may have a list of nurses and/or HCPs who works with the surgeons, e.g., based on previous surgical plans and/or shift schedules. The surgical computing system retrieve the host from a hospital server. Based on the list, the surgical computing system may identify users for the surgical procedure.

In examples, a surgical computing system may identify a user in an operating room based on a current surgical procedure step. The surgical computing system may identify a user as a surgeon if the current surgical procedure step is performed (e.g., normally performed) by a surgeon. For example, the surgical computing system may identify the user as a surgeon if the current surgical procedure step is making an incision into a patient's chest. The surgical computing system may identify a user as a nurse if the current surgical procedure step needs a surgical instrument, such as a surgical staple gun, to be reloaded.

In examples, a surgical computing system may identify a user in an operating room based on measurement data received from a sensing system. The measurement data may be or may include activities of a user. For example, the measurement data may be or may include hand activities of the user. Based on the hand activities, e.g., performing a surgery, the surgical computing system may identify the user as a surgeon. In examples, the surgical computing system may identify the user as a nurse based on the hand activities involving loading a surgical staple gun and/or moving (e.g., handling) one or more surgical instruments.

In examples, a surgical computing system may identify a user in an operation room based on location tracking information of a user in the operating room, proximity of a user to one or more surgical instruments as described herein.

If a surgical computing system identifies a user in an operating room, the surgical computing system may generate and/or send surgical aid information associated with (e.g., dedicated to) the identified user. The surgical aid information may be or may include an instruction on a surgical procedure, an instruction on how to perform a surgical procedure an instruction on how to use a surgical instrument, etc. The instruction may be audio and/or video. The surgical computing system may send the generated surgical aid information to a computing system associated with the identified user.

In examples, a surgical computing system may generate and/or surgical aid information, including send an audio instruction on a surgical procedure to an audio AR device that a surgeon is wearing. The surgical computing system may send a video instruction on a surgical procedure to a video AR device that a surgeon is wearing. The surgeon may look at and/or listen to the surgical aid information and confirm the surgical procedure.

In examples, a surgical computing system may generate and/or send surgical aid information including an audio and/or a video instruction on how to reload a surgical staple gun to a computing system that a nurse is wearing. The nurse may look at and/or listen to the surgical aid information and properly load the surgical staple gun.

In examples, a surgical computing system may generate and/or send surgical aid information including an audio indication and/or a video indication to a speaker and/or a monitor connected to the operating room. The audio and/or the video indication may be or may include a critical step indication. For example, the surgical computing system may broadcast that a next surgical procedure of a surgical operation is a critical step. The surgical computing system may broadcast the surgical information and the users max stop talking, e.g., to help the surgeon to focus.

The users in the operating room may act in response to the surgical aid information (e.g., the indication) from the surgical computing system. For example, the indication may indicate the next surgical procedure step. A nurse may prepare a surgical instrument for the next surgical procedure step. The hospital staff and/or the HCPs may adjust the lighting in the operating, e.g., to provide a focus and/or highlight to a region for the surgical procedure.

A surgical computing system may provide surgical aid information that is or includes an indication of fatigue control of a surgical instrument based on information about identified users. For example, the surgical computing system may be aware of the user's experience levels, preferences, tendencies, outcomes, etc. Based on the information associated with the user, the surgical computing system may include and/or recommend device settings for a next surgical step using the surgical aid information.

In examples, the information associated with the user (e.g., experience levels, preferences, tendencies, outcomes, etc.) may be retrieved from a hospital database. For example, the surgical computing system may connect to the hospital database and retrieve information about the identified user.

In examples, the information associated with the user may be sent to (e.g., relayed to) the surgical computing system by a computing system associated with the user. For example, the computing system associated with the user may provide the user information to the surgical computing system during a check in procedure and/or after the surgical computing system and the computing system establish a link.

If the surgical computing system determines that a user, e.g., a surgeon, is a first year resident and/or new to a surgical step, the surgical computing system may provide the surgical aid information step-by-step. The surgical aid information may include recommendations based on nominal historical data from the hospital database and/or server. The surgical aid information may include recommendations based on nominal historical data from the hospital database and/or server instead of and/or in addition to the user's historical data.

If the surgical computing system determines that the user, e.g., a surgeon, is experienced and/or an expert on a surgical step, the surgical computing system may provide the surgical aid information less frequently.

As described herein, a surgical computing system may receive measurement data from a sensing system associated with a user. The surgical computing system may use the measurement data to adjust an indication of fatigue control to a surgical instrument.

In examples, the surgical computing system may receive measurement data of a surgeon. The measurement data may be or may include a stress level and/or a fatigue level. As described herein, the surgical computing system may determine whether the stress level and/or the fatigue level has been elevated. Based on a determination that the surgeon has an elevated stress level and/or a fatigue level, the surgical computing system may communicate an indication of fatigue control to a surgical instrument. For example, the surgical computing system may slow functions (e.g., speed of articulation, jaw closure, etc.), increase precision, etc. The surgical computing system may communicate an indication of fatigue control to a surgical instrument if the surgical computing system detects an elevated stress level and/or a fatigue level and if a surgical step is a critical step.

Determination of a stress level and/or a fatigue level is further described in Ser. No. 17/156,296 titled ADAPTABLE SURGICAL INSTRUMENT CONTROL, filed contemporaneously, which is incorporated by reference herein in its entirety.

A surgical computing system may communicate with a computing system and/or a sensing system associated with a user. A surgical computing system may communicate with one or more other surgical computing systems in an operating room. For example, one or more surgical computing systems may exist in an operating room. A surgical computing system (e.g., a master surgical computing system or a primary surgical computing system) may have more processing capabilities (e.g., has the highest processing capability) in comparison to one or more surgical computing systems in the operating room. The primary surgical computing system may be connected a network (e.g., Internet, a hospital server and/or database, and/or a hospital cloud).

In examples, the primary surgical computing system may configure one or more other surgical computing systems (e.g., slave surgical computing systems and/or secondary surgical computing systems). For example, one or more secondary surgical computing systems may be in idle modes and/or may have processing power. If the primary surgical computing system determines that the primary surgical computing system needs additional processing power and/or needs to offload processing power (e.g., to perform additional analysis and/or providing additional steps and/or procedures during the operation), the primary surgical computing system may configure one or more secondary surgical computing systems to perform the processing tasks. For example, the primary surgical computing system may identify one or more secondary surgical computing systems that are in idle mode (e.g., not being used during a current surgical step) and/or have processing power. The primary surgical computing S stem may instruct the one or more idle secondary surgical computing systems to perform offloaded processing tasks.

In examples, the primary surgical computing system may configure one or more secondary surgical computing systems to acquire measurement data from one or more sensing systems associated with users in an operating room. For example, the primary surgical computing system may establish a link with a sensing system and/or a computing system associated with a user. The primary surgical computing system may assign a secondary surgical computing system to receive the measurement data from the linked sensing system and/or data from the linked computing system. The primary surgical computing system may configure other secondary surgical computing system to send an indication of fatigue control to a surgical instrument as described herein.

In examples, the primary surgical computing system may provide measurement data received by the primary surgical computing system to one or more secondary surgical computing systems. The primary surgical computing system may provide access to the received measurement data to the one or more secondary surgical computing systems.

As described herein, a surgical computing system may pair with one or more sensing systems and/or computing systems in an operating room. For example, a surgical computing system may interrogate (e.g., actively interrogate) other sensing systems and/or computing systems in the operating room to establish links and/or to access data. The surgical computing system may seek compatible system to establish a link and obtain access to data (e.g., measurement data and/or used identification data) stored in the sensing systems and/or computing systems.

Based on the established links with one or more compatible sensing systems and/or computing systems, the surgical computing system may index and/or record the locations and/or formats of the data. The surgical computing system (e.g., the primary surgical computing system) may send the information (e.g., the locations and/or formats of the data) to one or more secondary surgical computing systems.

A surgical computing system may store connections (e.g., network connection of other surgical computing systems, computing systems, and/or sensing systems in an operating room). For example, the surgical computing system may reuse stored connections (e.g., past network connections). The surgical computing system may use historic connection data as a setup for a new surgical procedure.

In examples, a surgical computing system may establish a link with a sensing system and/or a computing device associated with a user, such as a surgeon. Based on the link with the sensing system and/or the computing device, the surgical computing, system may remember the past list of sensing systems and/or the computing systems mat the surgical computing system established connection with. The surgical computing system may prompt a user to confirm a list of sensing systems and/or computing systems uploaded from the past list of systems. The user may select and/or deselect one or more sensing systems and/or computing systems from the past list.

The surgical computing system may use the past list to scan for the sensing systems and/or the computing systems that may be used for a current surgical procedure. The surgical computing system may update the list if one or more sensing systems and/or computing systems do not exist. The surgical computing system may update the list if one or more additional sensing systems and/or computing systems are detected.

The surgical computing system may retrieve a known list of systems that a user may frequently use. For example, if a surgeon has a known list of sensing systems (e.g., heart rate monitor, stress sensor, location identification, etc.) and the surgical computing system establishes a link with one of the known list of systems, the surgical computing system may prompt a connection and/or search other sensing systems from the known list. The sensing systems from the list may be or may include one or more previously connected sensing systems to the surgical computing system.

In examples, the surgical computing system may receive a known list of systems if the surgical computing system establishes a link with a sensing system and/or a computing system. For example, a surgical computing system may send a connection request message and/or a connection prompt to a sensing system. The sensing system may send a response to the connection request message and/or the connection prompt of the sensing system. The sensing system may include a list of other sensing systems and/or computing systems that the user used in previous surgical operations and/or established connections with the surgical computing system. The surgical computing system may use the list from the sensing system and scan for and/or establish connections with other systems based on the list.

In examples, if a sensing system and/or a computing system associated with a user, such as a surgeon, has a known list of systems (e.g., sensing systems and/or computing systems), the identification of a system may trigger a surgical computing system to prompt connections and/or search for other sensing systems and/or computing systems (e.g., specific to a patient). For example, a surgeon may prefer a particular array of sensing systems on patients. The surgical computing system may use information about the surgeon's preference and pre-populate a list of sensing systems for the patient. The surgical computing system may scan for and/or prompt connections to the pre-populated list of sensing systems on the patient.

A computing system may seek one or more sensing systems in an operating room. For example, a computing system may actively seek one or more sensing systems that are in proximity to the computing system. The computing system may be located in an operating room. The one or more sensing systems may include measurement data associated with a user. For example, the sensing systems may be surgeon sensing systems that may include measurement data associated with the surgeon. The sensing systems may be patient sensing systems that may include measurement data associated with the patient.

Figure 14:
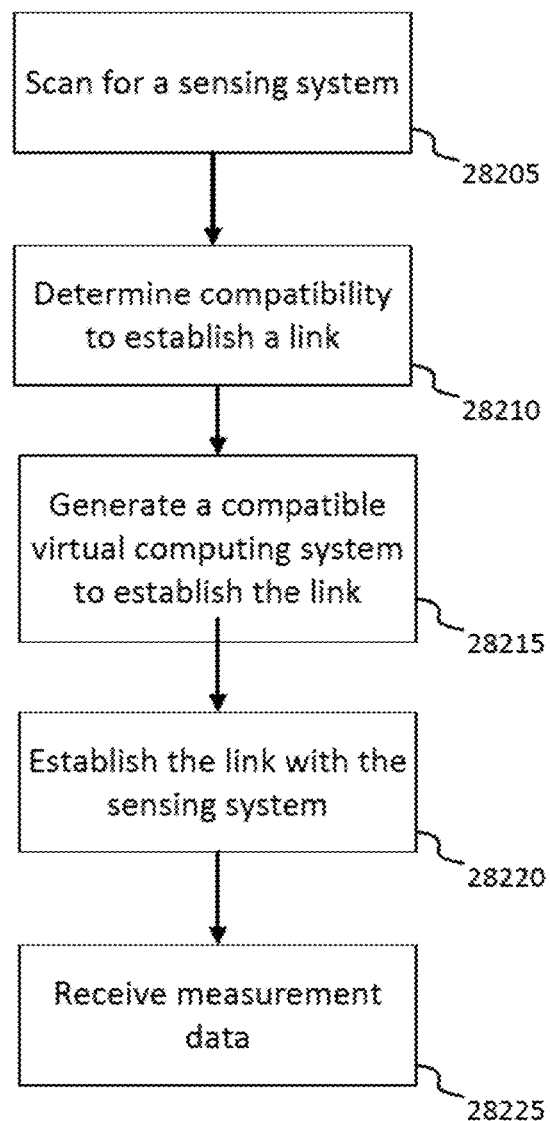
FIG. 14 illustrates an example flow of a computing system establishing a link with compatible and/or incompatible sensing system and/or computing system.

FIG. 14 illustrates an example bola of a computing system establishing a link with compatible and/or incompatible sensing system and/or computing system. At 28205, a computing system may scan an operating room and identify one or more devices that are located in the operating room and are in proximity to the computing system. The computing system may determine whether the detected devices are sensing systems. In examples, the computing system may request device identifications associated with the detected devices. The computing system may look up the device identifications and determine whether the detected devices are sensing systems. In examples, the computing system may receive sensing system indications from the sensing systems. In examples, the computing system may establish links with other computing systems in an operating room. The other computing systems may have a list of one or more sensing systems in the operating room. The computing system may attempt to establish links with one or more sensing systems from the list.

At 28210, a computing system may determine compatibility to establish a link with a detected sensing system. If the computing system detects/identifies one or more sensing systems, the computing system may determine whether the detected/identified sensing systems are compatible to the computing system. For example, the computing system may determine whether the one or more sensing systems are compatible with the computing system to establish connections and/or share data.

At 28215, a computing system may generate a compatible virtual computing system to establish a link with the incompatible sensing system. If the computing system determines that the computing system and the one or more sensing systems are incompatible to establish links (e.g., connections), the computing system may generate a virtual computing system that is compatible to establish links with the one or more sensing systems. In examples, the virtual computing system may be or may include an intermediate computing system (e.g., virtual computing system configured to run by the computing system) that is compatible with one or more sensing system. In examples, the virtual computing system may be configured to act as a bridge or a tunnel to establish a connection between the computing system and one or more incompatible sensing system. The computing system may establish links with the one or more incompatible sensing systems via the virtual computing system and receive measurement data as described herein. If the computing system determines that the computing system and the one or more sensing systems are incompatible to establish links, the computing system may generate a virtual computing system that is compatible to establish links with the one or more sensing systems. The computing system may establish links with the one or more incompatible sensing systems via the virtual computing system and receive measurement data as described herein.

At 28220, the computing system may establish the link with the sensing system. If the computing system determines that the computing system and the one or more sensing systems are compatible to establish links (e.g., using the virtual computing system), the computing system may establish links (e.g., pair) with the one or more sensing system. The computing system may receive measurement data from the one or more linked/paired sensing systems. In examples, the computing system may receive the measurement data from the one or more paired sensing systems. In examples, the computing system may monitor (e.g., passively monitor the measurement data from the one or more paired sensing systems. The computing system may send a list of measurement data and/or monitored measurement data from the one or more paired sensing systems to other computing system(s). For example, the computing system may send the list of measurement data and/or monitored measurement data from the one or more paired sensing systems to a primary computing system (e.g., a central computing system and/or a master computing system). In examples, the computing system may communicate paired information to other computing system(s), e.g., a primary computing system. The computing system may communicate the paired information to other computing system(s) periodically, if the computing system pairs with the other computing system(s) and/or when requested.

At 28225, the computing system may receive measurement data from one or more linked sensing systems. In examples, the computing system may store received measurement data from the one or more paired sensing systems. The computing system may send the stored measurement data to other computing system(s). The computing system may perform analysis of the measurement data, and/or the other computing system(s) may perform analysis of the measurement data.

In examples, the computing system may send an indication to one or more paired sensing systems. The indication may be or may include a request and/or instructions to send (e.g., directly send) the measurement data to other computing systems (e.g., to a primary computing system and/or secondary computing system).

The computing system may determine whether to connect with a new sensing system after establishing the links with one or more sensing systems. For example, the computing system may determine whether a new sensing system has entered an operating room. Based on a determination that a new sensing system has entered the operating room, the computing system may determine whether to pair with the new sensing system.

In examples, the computing system may determine whether to include and pair with the new sensing system or exclude and skip pairing with the new sensing system based on historic set data. For example, based on the historic set data, the computing system may recognize that a user, such as a circulating nurse from the next operating room, may stop by the current operating room at a time interval (e.g., every hour or every few minutes). Based on the historic set data that the user leaves the current operating room after few minutes, the computing system may exclude the new sensing system associated with the user (e.g., the circulating nurse) and skip pairing with the sensing system. For example, the computing system may determine that a sensing system is associated with a user from a different operating room. If the one or more sensing systems associated with the user from different operating rooms are detected by the computing system, the computing system may exclude the one or more sensing systems associated with the user from the different operating rooms (e.g., a circulating nurse) from establishing a link with the computing system. Based on the data, if a circulating nurse enters the current operating room (e.g., at a time interval), the computing system may exclude (e.g., automatically exclude) the one or more sensing systems associated with the circulating nurse from establishing a link with the computing system.

In examples, the computing system may look up a list of sensing systems. For example, the computing system may query a hospital central supply database and/or cloud database to determine whether the new sensing system belongs to (e.g., associated with) users in the current operating room. Based on a determination that the new sensing system does not belong the identified users in the current operating room, the computing system may exclude the new sensing system from the pairing list and skip pairing with the new sensing system.

In examples, the computing system may determine whether the new sensing system is associated with commercial sensing systems. For example, the computing system may recognize that the new sensing system is associated with non-patients and/or non-HCP. The computing system may determine that the new sensing system does not match with a list of sensing systems listed and/or approved by the hospital. The computing system may exclude the new sensing system from the paring list and skip pairing with the new sensing system.

One or more HCPs may enter an operating room for a surgical procedure. The HCPs may check in with a computing system, such as a surgical computing system (e.g., a primary surgical computing system). In examples, the HCPs may check in with the computing system as the HCPs are entering the room. In examples, the HCPs may check in with the computing system after entering the room and prior to the surgical procedure.

In examples, as described herein, the HCPs may enter their names directly to the computing system. In examples, the HCPs may select/click their names displayed in the computing system, in examples, the HCPs may tag badges, identification cards, and/or other identifiers. The computing system may retrieve one or more sensing systems associated with the HCPs based on the check in information provided/performed b the HCPs.

As describe herein, the computing system may identify the HCPs based on a camera teed in the operating room. For example, the computing system may have access to the camera feed in the operating room. Based on the camera feed, the computing system may identify the HCPs in the operating room. In examples, the computing system may identify the HCPs based on their locations in the operation room. In examples, the computing system may identify the HCPs based on their proximities to surgical instruments in the operating room.

In examples, if the computing system detects that a person is lying on an operating table, the computing system may identify the person as a patient. In examples, if the computing system detects a user standing next to and/or moving around near the patient and/or the operating table, the computing system may identify the user as a surgeon. In examples, if the computing system detects a user near a monitor and/or a phone, the computing system may identify the user as a nurse.

The computing system may retrieve one or more sensing systems associated with the identified users/HCPs. For example, the computing system may access database, such as a hospital central database, to retrieve one or more sensing systems that are associated with the identified patient, identified surgeon, and/or identified nurses. The hospital database may have a list of sensing systems and assignment of the sensing systems to one or more HCPs. For example, the hospital database may have a list of sensing systems that is assigned and/or associated with a surgeon. The hospital database may have a list of sensing systems that is assigned to and/or associated with a patient. The computing system may retrieve the list from the hospital database and aware of one or more sensing systems associated with the users in the operating room.

In examples, the computing system may determine the one or more sensing systems in an operating room based on connectivity to a network. The one or more sensing systems may attempt to establish a network connection when the sensing systems enter the operating room. For example, the one or more sensing systems may be connected to a Wifi that is assigned to the operating room. Based on the connection to the Wifi or attempted connection to the Wifi, the computing system may detect one or more sensing systems located in the operating room. As described herein, the computing system may identify and/or associate with the detected one or more sensing systems to corresponding users in the operating room.

In examples, the computing system may scan one or more sensing systems in an operating room. For example, the one or more sensing systems may have Bluetooth and/or Zigbee connection capability. The one or more sensing systems may be discoverable. The computing system may detect one or more sensing systems. As described herein, the computing system may identify and/or associate the discovered one or more sensing systems to corresponding users in the operating room.

The computing system may have information on one or more surgical instruments in an operating room. For example, the computing system may have a list of surgical instruments in an operating room. In examples, the computing system May retrieve a list of instruments in an operating room for a current operation from a pre-operation plan submitted by a surgeon and/or HCPs associated with the surgeon. The pre-operation plan may provide a list of instruments to be used for the surgical operation. The surgeon and/or the HCPs may upload the list to the computing system, to a hospital network, to hospital database. The computing system may retrieve the list.

In examples, an HCP, such as a nurse who is preparing the surgery, may have requested and/or uploaded the list of surgical instruments for an operation. The HCP may upload a surgical plan for the surgical procedure. The computing system may retrieve the list of one or more surgical instruments and/or the surgical plan.

A computing system described herein may handle offline data. A sensing system and/or a network of sensing systems may be connected to a network. For example, one or more sensing systems may be connected to the network through Wifi or the Internet on a mobile device. The Wifi or the Internet on the mobile device may go offline. The Wifi or the Internet may go offline clue to one or more of the following: lack of connection, fault, a dead battery, and/or power fault. The computing system may handle the data (e.g., the reservoir of data or data transfer to process that data) based on the last online interaction with the Wifi or the Internet.

Predicted values may be uploaded to one or more sensing systems and/or a mobile device periodically. For example, predicted values may be uploaded to the one or more sensing systems and/or a mobile device daily. The computing system may operate locally within a closed network of the devices. For example, the computing system may learn pattern associated with a user. The computing system may learn timing of the user, sleep schedule, and/or normal marker values for the user. The measured data and/or values may provide contexts for at certain events. For example, eating may result in a spike of blood sugar within a range. For example, a workout may increase heart rate (HR) by 20-30%.

Figure 15:
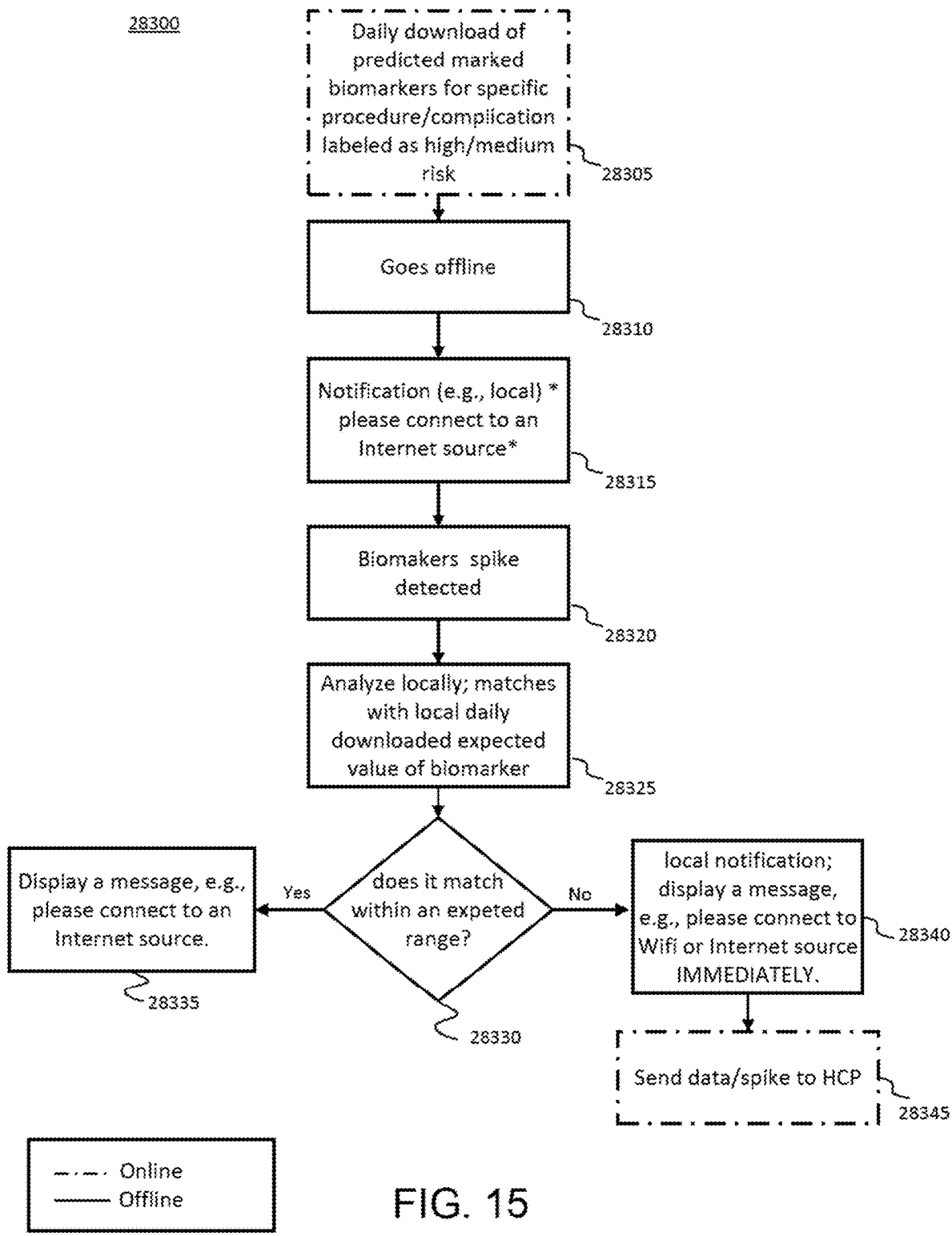
FIG. 15 illustrates an example flow of a computing system operating when online and offline.

FIG. 15 illustrates an example flow of a computing system operating when online and offline. At 28305, the computing system may receive daily download of predicted measurement data (e.g., marked biomarkers) for a specific surgical procedure and/or complication labeled as a high and/or a medium risk. At 28310, the computing system may go offline. The computing system may send a notification (e.g., a local notification). The notification may be or may include "Please connect to an Internet source." At 28315, the computing system may detect an elevated measurement data from a sensing system (e.g., spiked biomarkers). At 28325, the computing system may analyze locally. For example, the computing system may determine whether the elevated measurement data matches with daily downloaded expected value of the measurement data (e.g., local daily downloaded expected value of biomarker). At 28330, the computing system may determine whether the elevated measurement data is within an expected range. At 28335, the computing system may determine that elevated measurement data is within an expected range. The computing system may display a message. The message may be or may include "Please connect to an Internet source." At 28340, the computing system may determine that the elevated measurement data is outside of an expected range. The computing system may send a local notification. For example, the computing system may display a message. A message may be or may include "Please connect to Wifi. and/or Internet source IMMEDIATELY." At 28345, the computing system may go online. The computing system may send data and/or elevated measurement data to an HCP.

The computing system may backlog when the computing system is back online. The computing system may provide a prompt to a user to identify one or more specific flags/concerns. The computing system may ask about what event was occurring at that time (e.g., eating, sleeping, etc.) when back online. The provided information may indicate whether a problem existed or is occurring.

The computing system may have an offline mode. In the offline, mode, the computing system may look for a trigger (e.g., specific spikes) in measurement data (e.g., biomarkers). The computing system may perform analysis on the trigger when coming back online. The computing system may prioritize data storage and/or prioritize analysis at specific tune markers. The analysis may use more power and/or drain the battery faster. The computing system may switch the analysis to the computing device, e.g., from a cloud, etc.

Figure 16:
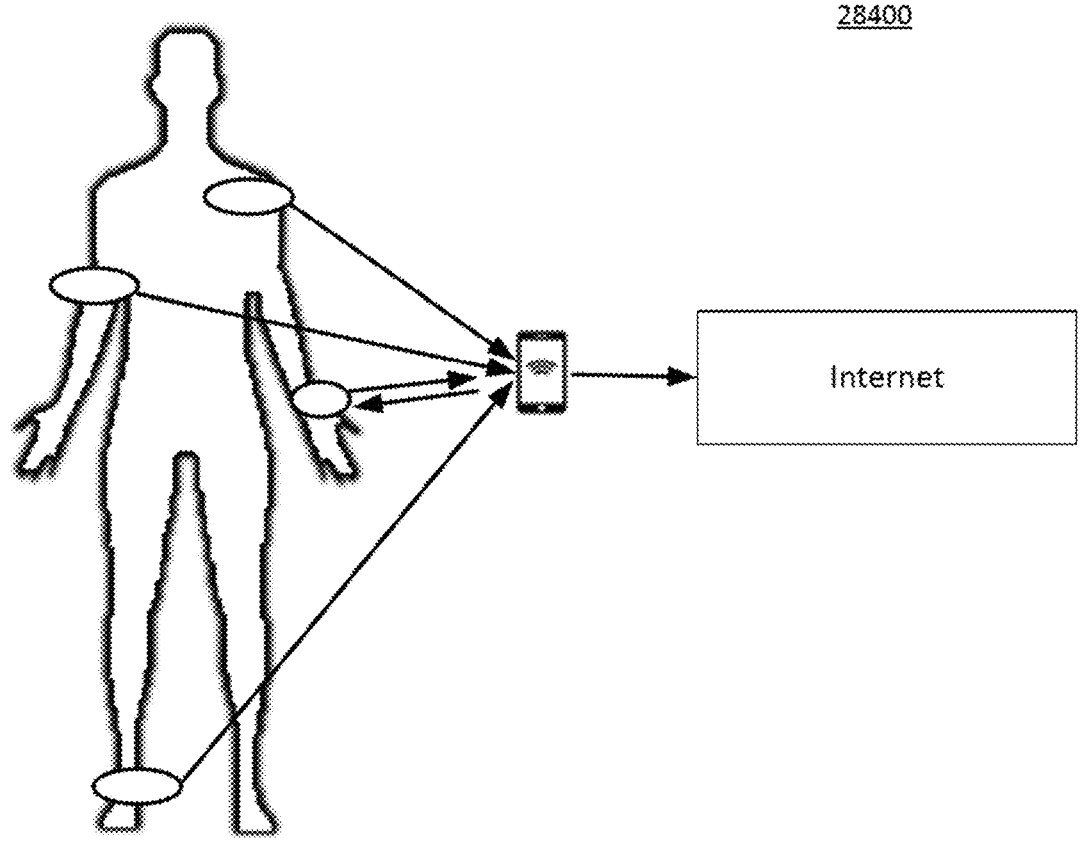
FIG. 16 illustrates an example a secondary computing system transition to a primary computing system to create a local computing system for low level analysis.
Figure 16:
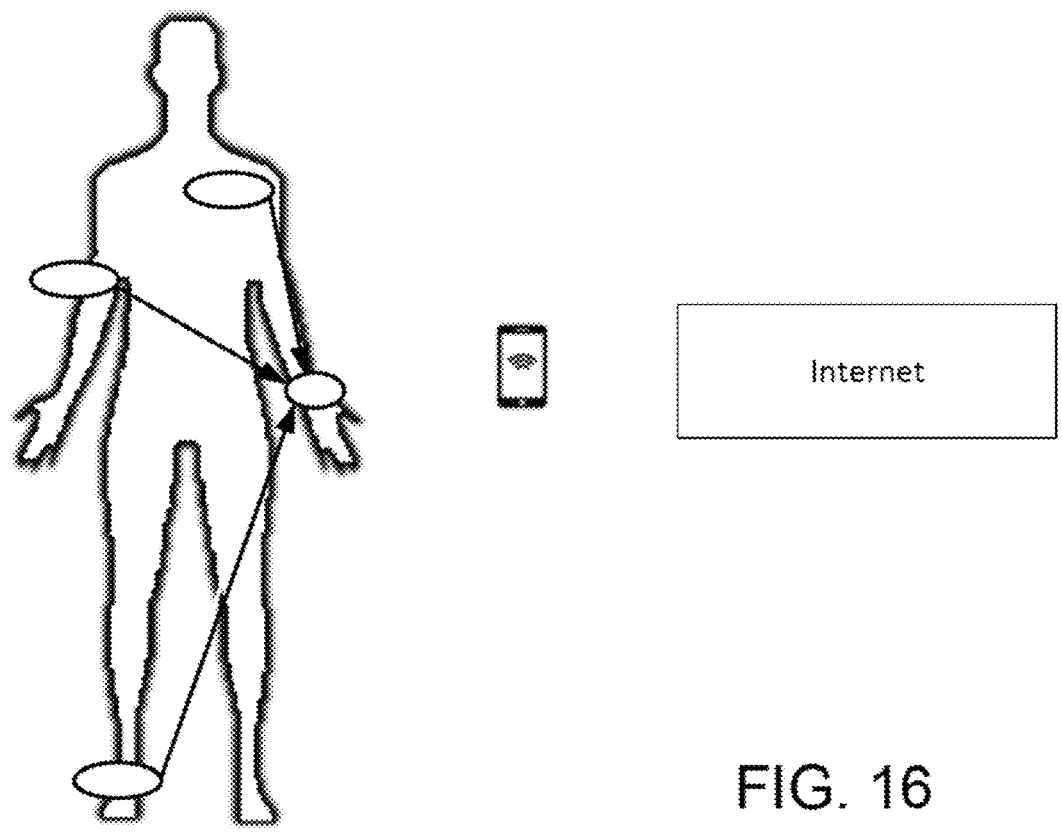

One or more computing systems (e.g., slave computing systems) may transition to one or more master computing systems. The transitioned master computing system may create a hub (e.g., a local hub) for analysis (e.g., low level analysis). FIG. 16 illustrates an example of a secondary computing system transitioning to a primary computing system to create a local computing system for low level analysis. A level 2 computing system (e.g., a primary computing system and/or a master computing system) may receive data and/or may receive 48-bit address of one or more computing systems that have been connected to a mobile device (e.g., from the mobile device). If Internet connection is lost and/or Bluetooth connection with the mobile device is disconnected, the level 2 computing system may page one or more level 1 computing systems (e.g., secondary computing systems and/or slave computing systems) to connect (e.g., automatically connect) to the level 2 computing system. The level 2 computing system may have unique address of other level 1 computing systems. A local network of computing systems may be created and may perform low level analysis and give a local notification via level 2 computing system if an emergency is detected and/or if something is wrong. A level 2 computing system may receive data and/or may receive 48-bit address of one or more computing systems that have been connected to a mobile device (e.g., from the mobile device). If Internet connection is lost and/or Bluetooth connection with the mobile device is disconnected, the level 2 computing system may page one or more level 1 computing systems to connect (e.g., automatically connect) to the level 2 computing system. The level 2 computing system may have unique address of other level 1 computing systems. A local network of computing systems may be created and may perform low level analysis and/or give a local notification via level 2 computing system if an emergency is detected and/or if something is wrong.

One or more sensing systems (e.g., wearable systems) may be dependent on an externally supplied piece of data for an operation on how the sensing systems would respond. For example, the sensing systems may operate, to the absence of that data in a short-term. The reaction of the system to lack of external connection may be time dependent. For example, in the short-term, the sensing system may use the last communicated value. If the sensing system is offline long enough (e.g., longer than pre-configured short-term time interval), the sensing system may start notifying the user. The sensing system may default into a safe mode operation and/or protected state.

If a recording capacity of a sensing system is reaching a maximum capacity and the sensing system cannot connect to an external system to upload measurement data, the sensing system may overwrite older data. The sensing system may keep every other or every tenth old data point and overwrite the other data to keep recording (e.g., and/or create space for further measurement data).

A sensing system may have one or more triggers to increase a criticality of connecting to an external system. The triggers in may include irregularities and/or exceeding critical thresholds. If the sensing system cannot connect to the external system (e.g., the outside world) when the sensing system needs to report back, the sensing system may intensify a notification to a user (e.g., a wearer) and/or may provide an instruction to the user on how to get access and/or seek other ways to gain access to a communication path.

A surgical instrument (e.g., a smart surgical instrument) may include one or more of the following: a stapler, an energy device (e.g., an advanced energy device), a biologic adjunct and/or a computing system.

An energy device may send a notification to an HCP, such as a surgeon. An energy device may send potentially problematic data, upcoming steps, and/or complications to the HCP.

For example, an energy device may detect bleeding and send a notification to the surgeon to adjust instrument operation. An example notification to the surgeon may include hemorrhage (IMA—sigmoid colectomy)—Warning: as the surgeon approaches IMA—the patient has a Low/High pH, Power Level x harmonic is suggested due to the risk of hemorrhage.

Examples of what measures may trigger a notification for an energy device as the energy device approaches a large vessel transection and coagulation may include one or more of the following: blood pH greater than 7.45; alcohol consumption; and/or menstrual cycle.

A biologic adjunct may provide an identification of patient escalation parameters that suggest adjunct or supplementary systems to be used.

A computing system may provide adjustments of operational thresholds. A computing system may highlight one or more surgical instruments (e.g., a combination surgical instruments) and patient irregularities. For example, the computing system may identify one or more surgical devices that may provide superior outcomes, access, and/or function based on the detected patent irregularities. A computing system may provide coordination of data streams. For example, the computing system may link one or more sensing systems to measure parameters (e.g., measurement data) with one or more surgical measurement devices (e.g., OR surgical measurement devices) to provide comparisons and/or baseline data.

The invention claimed is:

1. A surgical computing system comprising:
a processor configured to:
scan for a sensing system located in an operating room;
establish a link with the sensing system;
receive user role identification data from the sensing system using the established link;
identify a user role for a user in the operating room based on the received user role identification data;
receive measurement data from the sensing system;
based on the received measurement data, determine a fatigue level associated with the user; and
based on the identified user role and the determined fatigue level associated with the user, generate surgical aid information for the user in the operating room.

2. The surgical computing system of claim 1, wherein the user is a first user and the sensing system is a first sensing system, and wherein the processor is further configured to:
receive user role identification data from a second sensing system associated with a second user;
identify a user role for the second user in the operating room based on the received user role identification data; and
determine surgical aid information for the second user based on the identified user role for the second user.

3. The surgical computing system of claim 1, wherein the user role identification data comprises interactions between the user and at least one healthcare professional, and the user role for the user in the operating room is identified based on the interactions between the user and the at least one healthcare professional.

4. The surgical computing system of claim 1, wherein the sensing system is worn by the user, and wherein the processor is configured to:
identify the user role for the user as a surgeon based on a proximity of the sensing system to one or more surgical instruments.

5. The surgical computing system of claim 1, wherein the processor is configured to:
generate augmented reality (AR) content for the identified user role; and
send the AR content to an AR device associated with the user.

6. The surgical computing system of claim 1, wherein the processor is configured to:
determine an elevated stress level associated with the user;
obtain surgical contextual data;
identify a surgical instrument associated with the user based on the surgical contextual data and the identified user role; and
obtain an instruction on how to use the surgical instrument for inclusion in the surgical aid information.

7. The surgical computing system of claim 1, wherein the surgical aid information for the user comprises an indication of fatigue control to a surgical instrument, and the processor is configured to:
based on the received measurement data, determine an elevated fatigue level associated with the user;
obtain surgical contextual data;
determine whether the user is operating the surgical instrument based on the surgical contextual data and the identified user role; and
based on a determination that the user is operating the surgical instrument, send the indication of fatigue control to the surgical instrument.

8. The surgical computing system of claim 1, wherein the user role comprises at least one of: a surgeon, a nurse, a patient, a hospital staff, or a health care professional.

9. The surgical computing system of claim 1, wherein the user role identification data comprises visual data of the user in the operating room, and the user role for the user in the operating room is identified based on the visual data of the user in the operating room.

10. The surgical computing system of claim 1, wherein the sensing system is worn by the user, and wherein the processor is configured to:
identify the user role for the user as a surgeon based on location tracking information associated with the sensing system during a surgical procedure.

11. A method comprising:
scanning for a sensing system located in an operating room;
establishing a link with the sensing system;
receiving user role identification data from the sensing system using the established link;
identifying a user role for a user in the operating room based on the received user role identification data;
receiving measurement data from the sensing system;
based on the received measurement data, determining a fatigue level associated with the user; and
based on the identified user role and the determined fatigue level associated with the user, generate surgical aid information for the user in the operating room.

12. The method of claim 11, wherein the user is a first user and the sensing system is a first sensing system, and wherein the method further comprises:

receiving user role identification data from a second sensing system associated with a second user;

identifying a user role for the second user in the operating room based on the received user role identification data; and determining surgical aid information for the second user based on the identified user role for the second user.

13. The method of claim 11, wherein the sensing system is worn by the user, and wherein the method comprises:

identifying the user role for the user as a surgeon based on a proximity of the sensing system to one or more surgical instruments.

14. The method of claim 11, comprising:

generating augmented reality (AR) content for identified user role; and send the AR content to an AR device associated with the user.

15. The method of claim 11, comprising:

determining an elevated stress level associated with the user;

obtaining surgical contextual data;

identifying a surgical instrument associated with the user based on the surgical contextual data and the identified user role; and obtaining an instruction on how to use the surgical instrument for inclusion in the surgical aid information.

16. The method of claim 11, wherein the surgical aid information for the user comprises an indication of fatigue control to a surgical instrument, the method comprising:

based on the received measurement data, determining an elevated fatigue level associated with the user;

obtaining surgical contextual data;

determining whether the user is operating the surgical instrument based on surgical contextual data and the identified user role; and based on a determination that the user is operating the surgical instrument, send the indication of fatigue control to surgical instrument.

17. The method of claim 11, wherein the user role identification data comprises interactions between the user and at least one healthcare professional, and the user role for the user in the operating room is identified based on the interactions between the user and the at least one healthcare professional.

18. The method of claim 11, wherein the user role identification data comprises visual data of the user in the operating room, and the user role for the user in the operating room is identified based on the visual data of the user in the operating room.

19. The method of claim 11, wherein the sensing system is worn by the user, and wherein the method comprises:

identifying the user role for the user as a surgeon based on location tracking information associated with the sensing system during a surgical procedure.

20. A non-transitory computer-readable medium comprising instructions for performing the method of claim 11 when executed by a processor.

* * * * *